(12) United States Patent
Dzierba et al.

(10) Patent No.: US 8,304,577 B2
(45) Date of Patent: Nov. 6, 2012

(54) MODULATORS OF G PROTEIN-COUPLED RECEPTOR 88

(75) Inventors: Carolyn Diane Dzierba, Middletown, CT (US); Richard A. Hartz, Middletown, CT (US); Yingzhi Bi, Plainsboro, NJ (US); Vijay T. Ahuja, Middletown, CT (US); Joanne J. Bronson, Durham, CT (US); Kenneth Carson, Princeton, NJ (US); Giovanni Cianchetta, Lawrenceville, NJ (US); Michael Green, Easton, PA (US); David Kimball, East Windsor, NJ (US); S. Roy Kimura, Stamford, CT (US); Soojin Kwon, Haworth, NJ (US); John E. Macor, Guilford, CT (US); Yulian Zhang, Yardley, PA (US); Greg Zipp, Robbinsville, NJ (US)

(73) Assignees: Bristol-Myers Squibb Company, Princeton, NJ (US); Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 12/898,016

(22) Filed: Oct. 5, 2010

(65) Prior Publication Data
US 2011/0251196 A1  Oct. 13, 2011

Related U.S. Application Data

(60) Provisional application No. 61/250,229, filed on Oct. 9, 2009.

(51) Int. Cl.
*C07C 233/00* (2006.01)
(52) U.S. Cl. ...................................................... 564/123
(58) Field of Classification Search ................... 564/123
See application file for complete search history.

(56) References Cited

U.S. PATENT DOCUMENTS

| 7,332,524 B2 * | 2/2008 | Linders et al. ................. 514/617 |
| 2006/0079506 A1 * | 4/2006 | Linders et al. ........... 514/217.11 |
| 2008/0096869 A1 * | 4/2008 | Linders et al. ................. 514/218 |

FOREIGN PATENT DOCUMENTS

| CN | 1733708 | 2/2006 |
| JP | 2007-217408 | 8/2007 |
| WO | WO 94/12461 | 6/1994 |
| WO | WO 96/21464 | 7/1996 |
| WO | WO 03/086325 | 10/2003 |
| WO | WO03/103666 A2 | 12/2003 |
| WO | WO2004/047738 A2 | 6/2004 |
| WO | WO 2004/056745 | 7/2004 |
| WO | WO 2004/072018 | 8/2004 |
| WO | WO 2005/000309 | 1/2005 |
| WO | WO2005/051890 A1 | 6/2005 |
| WO | WO 2006/012227 | 2/2006 |
| WO | WO2006/027252 A1 | 3/2006 |
| WO | WO 2007/117715 | 10/2007 |
| WO | WO2007/129188 A1 | 11/2007 |
| WO | WO 2008/022154 | 2/2008 |
| WO | WO 2011/044195 | 4/2011 |
| WO | WO 2011/044212 | 4/2011 |

OTHER PUBLICATIONS

U.S. Appl. No. 12/895,916, filed Oct. 1, 2010, Bi et al.
U.S. Appl. No. 12/897,004, filed Oct. 4, 2010, Bi et al.
Garrido, Dulce M., et al, "Synthesis and Activity of Small Molecule GPR40 Agonists," Bioorganic & Medicinal Chemistry Letters, vol. 16, No. 7, pp. 1840-1845, 2006.

* cited by examiner

*Primary Examiner* — Susannah Chung
(74) *Attorney, Agent, or Firm* — Pamela A. Mingo; Gary D. Greenblatt

(57) ABSTRACT

The present disclosure is generally directed to compounds which can modulate G-protein coupled receptor 88, compositions comprising such compounds, and methods for modulating G-protein coupled receptor 88.

4 Claims, No Drawings

MODULATORS OF G PROTEIN-COUPLED RECEPTOR 88

CROSS-REFERENCE TO RELATED APPLICATIONS

This application claims the benefit of U.S. provisional application Ser. No. 61/250,229 filed Oct. 9, 2009.

The present disclosure is generally directed to compounds which can modulate G-protein coupled receptor 88, compositions comprising such compounds, and methods for modulating G-protein coupled receptor 88.

GPR88 is an orphan member of the G protein coupled receptor (GPCR) superfamily. GPR88 demonstrates GPCR activity several assays including GTPgS binding, calcium influx, and cAMP inhibition assays. The receptor exhibits high expression in the CNS, with measurable expression in peripheral tissues including liver. CNS expression is particularly robust in striatum, paralleling that of the dopamine D2 receptor (Mizushima et. al, *Genomics* 69, 314-321 (2000)) suggesting the receptor may play a role in regulating dopaminergic activity. Consistent with this, genetically-modified mice that lack GPR88 expression exhibit enhanced response to dopaminergic agonists, altered performance in models relevant to schizophrenia (prepulse inhibition, conditioned avoidance responding) and depression (forced swim test). These results demonstrate therapeutic potential for GPR88 in treating CNS diseases. Transcriptional profiling studies have also revealed GPR88 expression is altered by treatments or conditions related to bipolar disorder (Ogden et al., *Mol Psychiatry* 2004 November; 9(11):1007-29 and Brandish, et al. Neuron, Vol. 45, 861-872, Mar. 24, 2005, schizophrenia (Matsuoka, et al. *Synapse* 2008 January; 62(1):1-7), and depression (Conti et al., Mol. Psychiatry. 2007 February; 12(2):167-89.), providing additional support for GPR88 as an essential modulator of CNS signaling pathways related to psychiatric disease.

GPR88 is also expressed liver tissue suggesting GPR88 signaling may contribute to regulation of metabolic processes. Initial phenotypic characterization of genetically-modified mice lacking GPR88 expression (Level 1 data) suggests these animals exhibit altered response to glucose, insulin levels and triglycerides. These results suggest compounds that modulate GPR88 activity may have utility in metabolic diseases.

Based on these data, compounds that modulate GPR88 activity (agonists, antagonists, or modulators) are predicted to have therapeutic utility in the treatment of psychosis, cognitive deficits in schizophrenia, affective disorders, attention deficit hyperactivity disorders, bipolar disorder, drug addiction, Parkinson's disease, Alzheimer's disease, obesity and diabetes.

In a first aspect the present disclosure provides a compound of Formula (I)

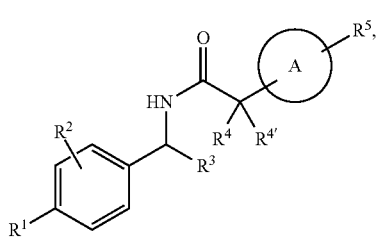

or a pharmaceutically acceptable salt thereof, wherein
A is phenyl;
$R^1$ is $C_4$-$C_6$ alkoxy;
$R^2$ is selected from hydrogen, $C_1$-$C_3$ alkyl; and halo;
$R^3$ is selected from
$C_1$-$C_3$ alkyl;
heterocyclyl;
hydroxy-$C_1$-$C_3$ alkyl; and
$(NR^aR^b)$—$C_1$-$C_3$ alkyl; wherein $R^a$ and $R^b$ are each independently selected from
hydrogen;
$C_2$-$C_6$ alkenyl optionally substituted with an amino group;
$C_1$-$C_6$ alkyl optionally substituted with an amino group;
$C_3$-$C_6$ cycloalkyl-$C_1$-$C_3$ alkyl wherein the cycloalkyl is optionally substituted with an amino group;
heterocyclyl-$C_1$-$C_3$ alkyl;
$R^6$—C(O)—; wherein $R^6$ is selected from
amino-$C_1$-$C_6$ alkyl wherein the alkyl is optionally substituted with a $C_1$-$C_3$ alkoxy or hydroxy group;
aryl substituted with an amino group;
$C_3$-$C_6$ cycloalkyl substituted with an amino group;
$C_3$-$C_6$-cycloalkyl-$C_1$-$C_3$ alkyl wherein the alkyl part is substituted with an amino group;
heterocyclyl; and
heterocyclyl-$C_1$-$C_3$ alkyl, wherein the alkyl part is substituted with an amino group and wherein the heterocyclyl part is optionally substituted with a $C_1$-$C_3$ alkyl group; and
$R^7$—C(O)—$C_1$-$C_3$ alkyl; wherein $R^7$ is $(CH_3)_2N$—$(CH_2)_2$—NH—;
or, $R^a$ and $R^b$, together with the nitrogen atom to which they are attached, form a morpholinyl or piperazinyl ring wherein the piperazinyl ring is optionally substituted with $C_1$-$C_3$ alkyl;
$R^4$ is selected from $C_1$-$C_3$ alkyl and hydroxy-$C_1$-$C_3$ alkyl;
$R^{4'}$ is selected from hydrogen and $C_1$-$C_3$ alkyl; or
$R^4$ and $R^{4'}$, together with the carbon atom to which they are attached, form a $C_3$-$C_6$ cycloalkyl ring; and
$R^5$ is selected from hydrogen, $C_1$-$C_3$ alkyl, and halo.

In a first embodiment of the first aspect the present disclosure provides a compound of Formula (I), or a pharmaceutically acceptable salt thereof, wherein $R^3$ is $C_1$-$C_3$ alkyl.

In a second embodiment of the first aspect the present disclosure provides a compound of Formula (I), or a pharmaceutically acceptable salt thereof, wherein $R^3$ is heterocyclyl.

In a third embodiment of the first aspect the present disclosure provides a compound of Formula (I), or a pharmaceutically acceptable salt thereof, wherein $R^3$ is hydroxy-$C_1$-$C_3$ alkyl.

In a fourth embodiment of the first aspect the present disclosure provides a compound of Formula (I), or a pharmaceutically acceptable salt thereof, wherein $R^3$ is $(NR^aR^b)$—$C_1$-$C_3$ alkyl.

In a second aspect the present disclosure provides a compound of formula (II)

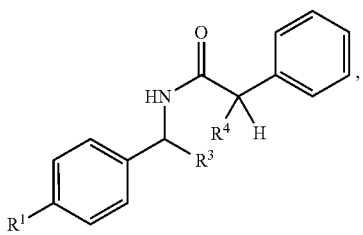

(II)

or a pharmaceutically acceptable salt thereof, wherein
$R^1$ is $C_4$-$C_6$ alkoxy;
$R^3$ is selected from
hydroxy-$C_1$-$C_3$ alkyl; and
($NR^aR^b$)—$C_1$ alkyl; wherein $R^a$ and $R^b$ are each independently selected from
hydrogen;
$C_1$-$C_5$ alkyl;
$C_3$-$C_5$ cycloalkyl-$C_1$ alkyl wherein the cycloalkyl is optionally substituted with an amino group;
heterocyclyl-$C_1$ alkyl;
$R^6$—C(O)—; wherein $R^6$ is selected from
amino-$C_1$-$C_5$ alkyl wherein the alkyl is optionally substituted with a $C_1$ alkoxy group;
$C_3$ cycloalkyl-$C_2$ alkyl wherein the alkyl part is substituted with an amino group;
heterocyclyl; and
heterocyclyl-$C_2$ alkyl, wherein the alkyl part is substituted with an amino group;
or, $R^a$ and $R^b$, together with the nitrogen atom to which they are attached, form a morpholinyl or piperazinyl ring wherein the piperazinyl ring is substituted with $C_1$-$C_3$ alkyl; and
$R^4$ is selected from $C_1$-$C_2$ alkyl and hydroxy-$C_1$ alkyl.

In a third aspect the present disclosure provides a composition comprising a compound of Formula (I), or a pharmaceutically acceptable salt thereof, and a pharmaceutically acceptable carrier.

In a fourth aspect the present disclosure provides a method of treating a disorder selected from a neurological disorder or a metabolic disease in a mammal, comprising administering to the mammal a therapeutically effective amount of a compound of Formula (I), or a pharmaceutically acceptable salt thereof.

In a first embodiment of the fourth aspect the mammal is a human.

In a second embodiment of the fourth aspect the disorder is a neurological disorder is selected from psychosis, cognitive deficits in schizophrenia, affective disorders, attention deficit hyperactivity disorders, drug addiction, Parkinson's disease, and Alzheimer's disease.

In a third embodiment of the fourth aspect the disorder is a metabolic disease selected from obesity and diabetes.

In a fifth aspect the present disclosure provides a method of modulating G protein-coupled receptor 88 in a mammal, comprising administering to the mammal a therapeutically effective amount of a compound of Formula (I), or a pharmaceutically acceptable salt thereof.

In a first embodiment of the fifth aspect the mammal is a human.

In a second embodiment of the fifth aspect the G protein-coupled receptor 88 is modulated in order to treat a neurological disorder or metabolic disease.

In a third embodiment of the fifth aspect the G protein-coupled receptor 88 is modulated in order to treat a neurological disorder wherein the neurological disorder is selected from psychosis, cognitive deficits in schizophrenia, affective disorders, attention deficit hyperactivity disorders, bipolar disorder, drug addiction, Parkinson's disease, and Alzheimer's disease.

In a fourth embodiment of the fifth aspect the G protein-coupled receptor 88 is modulated in order to treat a metabolic disease wherein the metabolic disease is selected from obesity and diabetes.

Other embodiments of the present disclosure may comprise suitable combinations of two or more of embodiments and/or aspects disclosed herein.

Yet other embodiments and aspects of the disclosure will be apparent according to the description provided below.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to six carbon atoms.

The term "amino," as used herein, refers to —$NH_2$.

The term "aminoalkyl," as used herein, refers to an alkyl group substituted with one, two, or three amino groups.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl.

The term "(cycloalkyl)alkyl," as used herein, refers to an alkyl group substituted with one, two, or three cycloalkyl groups.

The terms "halo" and "halogen," as used herein, refer to F, Cl, Br, or I.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "heterocyclylalkyl, as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "($NR^aR^b$)alkyl," as used herein, refers to an alkyl group substituted with one, two, or three —$NR^aR^b$ alkyl groups.

The term "—$NR^aR^b$," as used herein, refers to two groups, $R^a$ and $R^b$, attached to the parent molecular moiety through a nitrogen atom.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to modulate G protein-coupled receptor 88. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: BOC or Boc for tert-butoxy carbonyl; RT or rt or r.t. for room temperature or retention time (context will dictate); $t_R$ for retention time; HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; i-Pr or iPr for isopropyl; THF for tetrahydrofuran; EtOH for ethanol; Ac for acetyl; DMAP for N,N-dimethylaminopyridine; TEA or $Et_3N$ for triethylamine; DIEA or i-$Pr_2NEt$ for diisopropylethylamine; Me for methyl; TFA for trifluoroacetic acid; Ph for phenyl; DMF for N,N-dimethylformamide; MeCN for acetonitrile; TPAP for tetrapropylammonium perruthenate; DIAD for diisopropyl azodicarboxylate; HOBt for 1-hydroxybenzotriazole; Et for ethyl; h or hr or hrs for hours; min or mins for minutes; EtOAc for ethyl acetate; DCM for dichloromethane; MeOH for methanol; AcOH for acetic acid; $(DHQD)_2PHAL$ for hydroquinidine 1,4-phthalazinediyl diether; DCC for dicyclohexyl carbodiimide; and MeOD for $CD_3OD$.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 9 are prepared by the methods outlined in Scheme 1. The amine of a compound of formula 1 is protected with an appropriate protecting group reagent as described in *Protective Groups in Organic Synthesis* (Greene, Wuts; 3$^{rd}$ ed., 1999, John Wiley & Sons, Inc.), preferably t-butylcarbamate. The reaction is carried out in the presence of an appropriate base, such as N,N-diisopropylethylamine to produce the Boc-protected compound (2). Alkylation of the hydroxyl group in 2 is achieved by treatment of 2 with an alcohol ($R^1OH$), triphenylphosphine, an azodicarboxylate ester $R^cO_2CN=NCO_2R^c$ (where $R^c$ is lower alkyl) in an inert solvent, such as tetrahydrofuran or methylene chloride, at temperatures ranging from 0° C. to 100° C. The choices of phosphine, solvent or azodicarboxylate ester are known to those skilled in the art of organic chemistry as described by Mitsunobu (Mitsunobu, O. *Synthesis* 1981, 1). Reduction of the ester in 3 is carried out in the presence of a reducing agent such as lithium borohydride or sodium borohydride in the presence of lithium chloride in a mixture of tetrahydrofuran and ethanol to furnish intermediate 4. The hydroxyl group of intermediate 4 is protected with an appropriate protecting group reagent as described in *Protective Groups in Organic Synthesis* (Greene, Wuts; 3$^{rd}$ ed., 1999, John Wiley & Sons, Inc.), preferably acetate, by treatment of 4 with acetyl chloride in the presence of triethylamine and N,N-dimethylaminopyridine in tetrahydrofuran. Compound 6 is prepared by treatment of 5 with hydrochloric acid in a solvent such as ether or dioxane. Intermediate 6 is then coupled with a carboxylic acid, such as compound 7, using standard peptide coupling reagents such as HATU, BOP, EDC, TBTU, preferably HATU, in the presence of a base, such as N,N-diisopropylethylamine, and a solvent, such as tetrahydrofuran to produce 8. Removal of the acetate protecting group with sodium methoxide affords compounds of formula 9.

Scheme 1

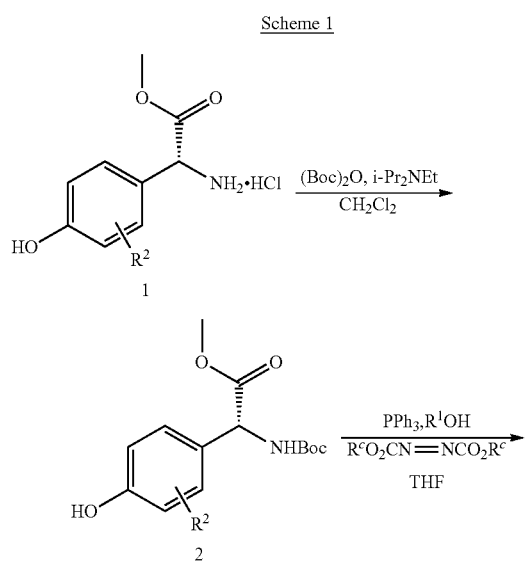

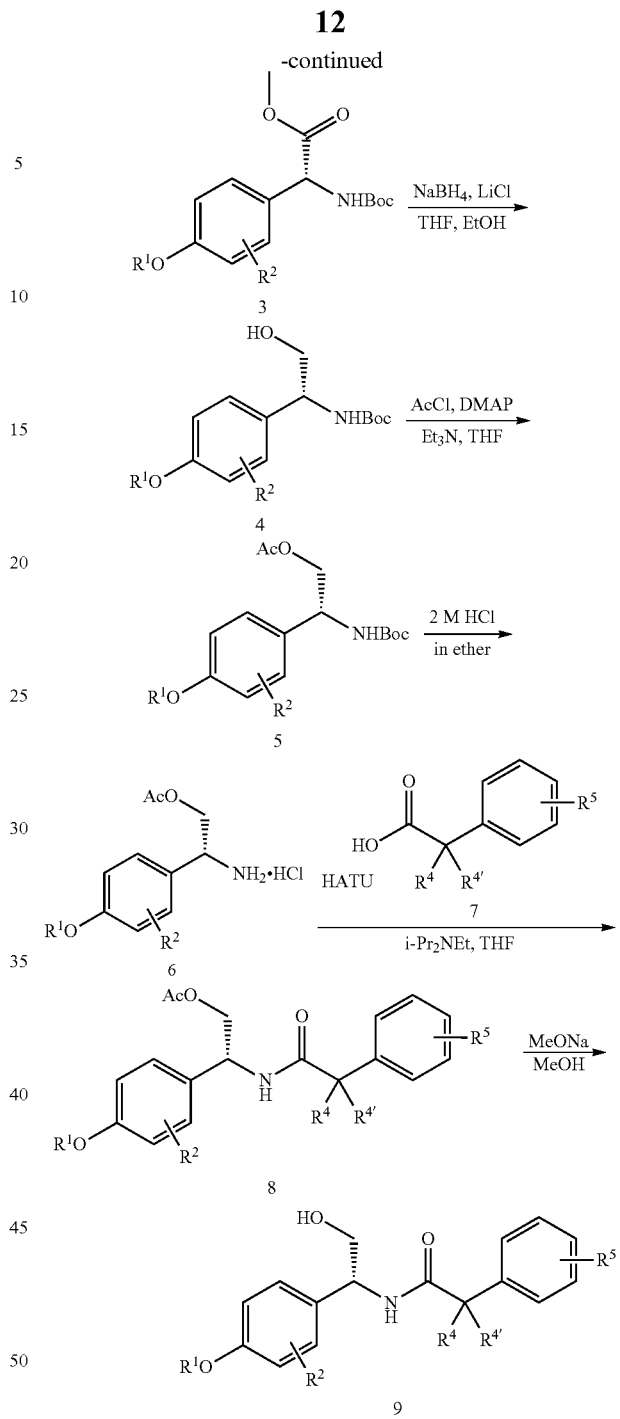

Compounds of formula 12 are prepared by the methods outlined in Scheme 2. Compound 3, prepared by the method outlined in Scheme 1, is treated with a Grignard reagent, such as methylmagnesium bromide, to furnish intermediate 10. Removal of the Boc protecting group in 10 with acid, such as trifluoroacetic acid (TFA) or hydrochloric acid as described in *Protective Groups in Organic Synthesis* (Greene, Wuts; 3$^{rd}$ ed., 1999, John Wiley & Sons, Inc.) provides intermediate 11. Intermediate 11 is then coupled with a carboxylic acid, such as compound 7, using standard peptide coupling reagents such as HATU, BOP, EDC, TBTU, preferably HATU, in the presence of a base, such as N,N-diisopropylethylamine, and a solvent, such as tetrahydrofuran to produce compounds of formula 12.

Scheme 2

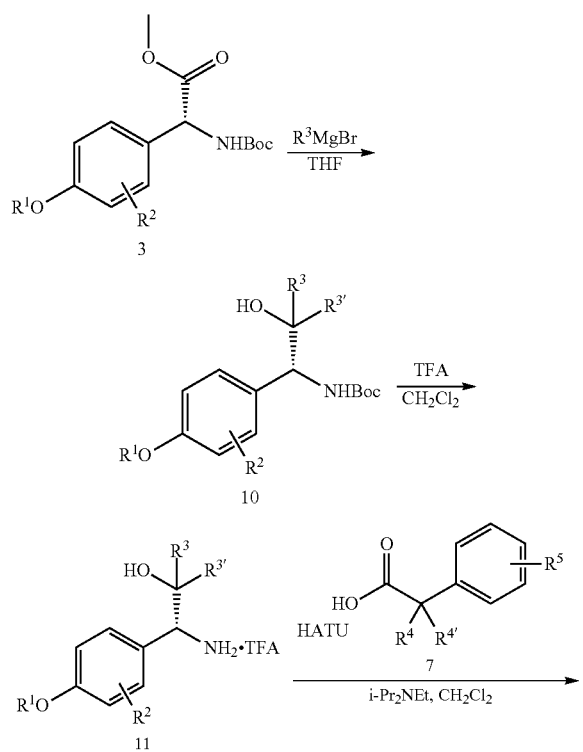

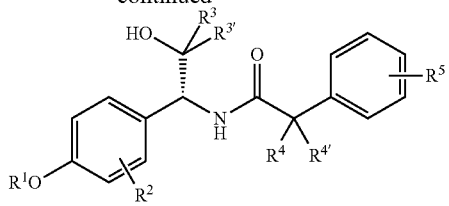

Compounds of formula 18 and 19 are prepared by the methods outlined in Scheme 3. Compound 4, prepared by the method outlined in Scheme 1, is treated with carbon tetrabromide and triphenylphosphine to furnish compound 13. The bromide is converted to azide 14 by treatment with sodium azide. The Boc protecting group is then removed with trifluoroacetic acid and the resultant amine is coupled with a carboxylic acid, such as compound 7, as described previously (vide supra) to provide compound 16. The azide is converted to an amine with a reducing agent, such as palladium on carbon in the presence of hydrogen, to furnish compound 17. Compound 17 is then treated with an aldehyde (1 or more equivalents) in the presence of a reducing agent, such as sodium triacetoxyborohydride or sodium cyanoborohydride, in a polar aprotic solvent to provide compounds of formula 18. Alternatively, compound 17 is coupled with a carboxylic acid, which may or may not contain a protected amine, using conditions described previously. If the carboxylic acid also contains an amine protected with a Boc group, the Boc group is removed with an acid, such as trifluoroacetic acid to afford compounds of formula 19.

Scheme 3

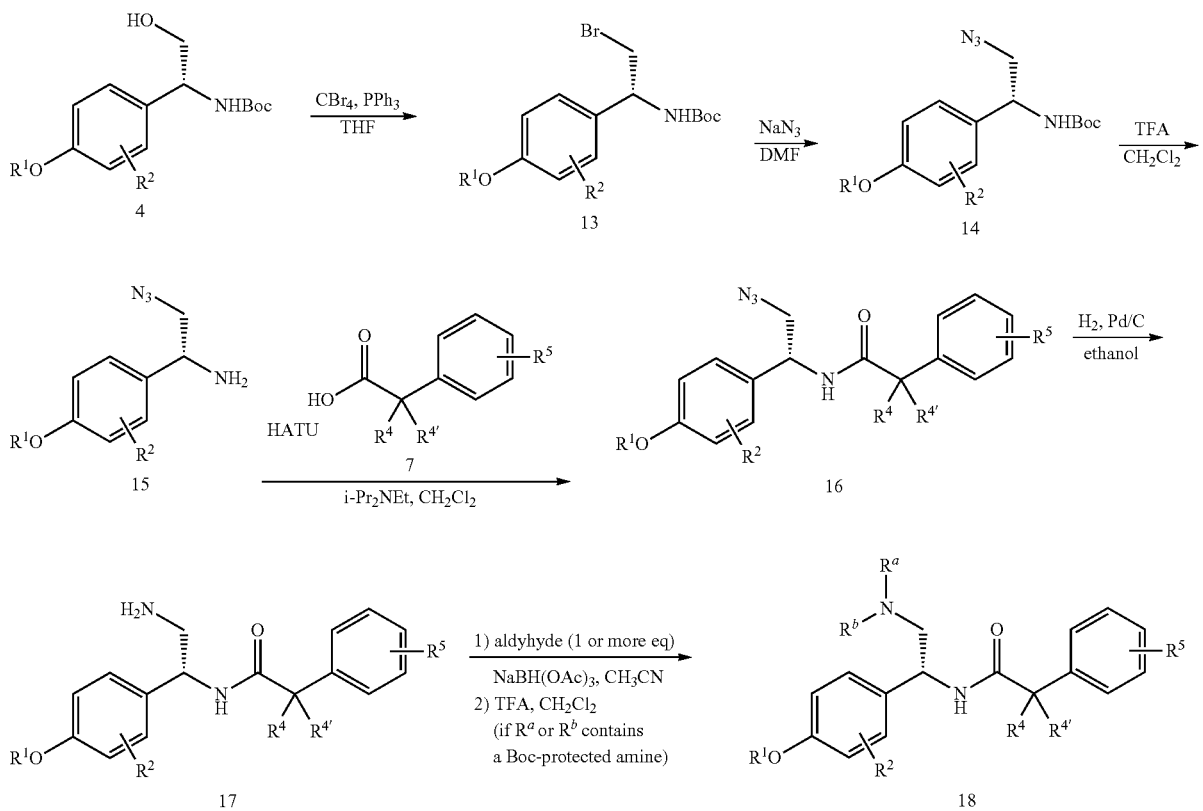

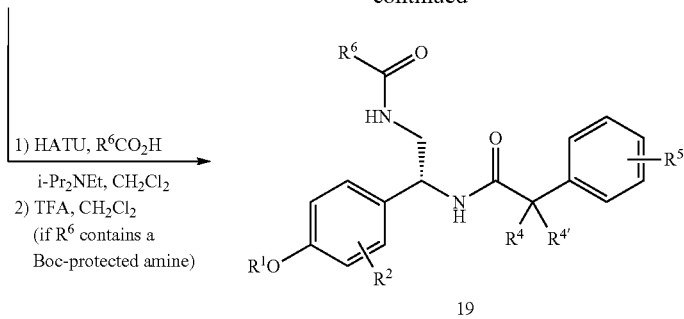

Compounds of formula 20 are prepared from compound 17 by treatment of 17 with 1-bromo-2-(2-bromoethoxy)ethane in the presence of a base, such as potassium carbonate, in a polar aprotic solvent, such as acetonitrile (Scheme 4).

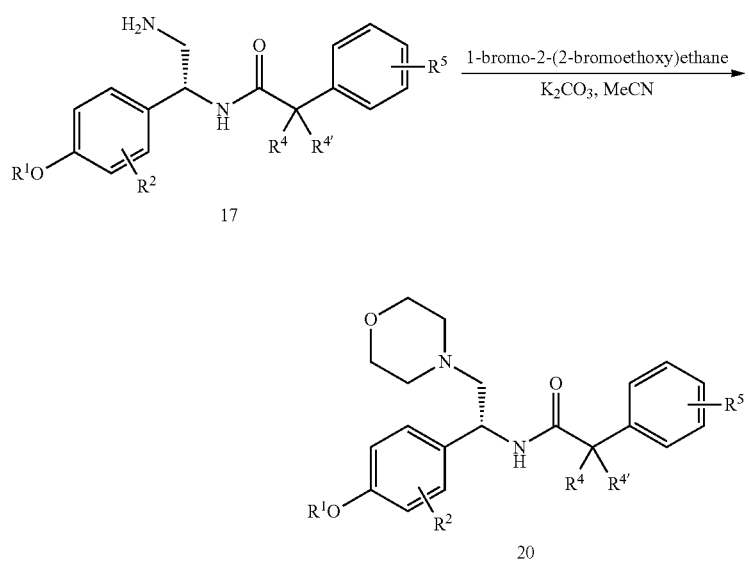

Compounds of formula 24 are prepared by the methods outlined in Scheme 5. Compound 4, prepared by the method outlined in Scheme 1, is treated with an oxidizing agent, such as, but not limited to Dess-Martin periodinane, Swern oxidation conditions or TPAP, preferably Dess-Martin periodinane to give compound 21. Compound 21 is then treated with 1-methylpiperazine in the presence of a reducing agent, such as sodium triacetoxyborohydride or sodium cyanoborohydride, in a polar aprotic solvent to provide intermediate 22. The Boc protecting group in 22 is then removed with trifluoroacetic acid as described previously to give 23. The resultant amine in 23 is coupled with a carboxylic acid, such as compound 7, as described previously (vide supra) to provide compounds of formula 24.

Scheme 5

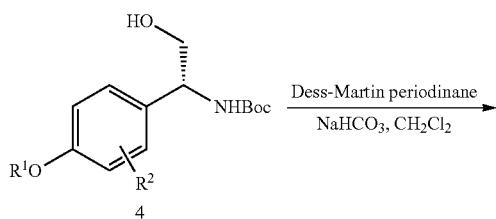

-continued

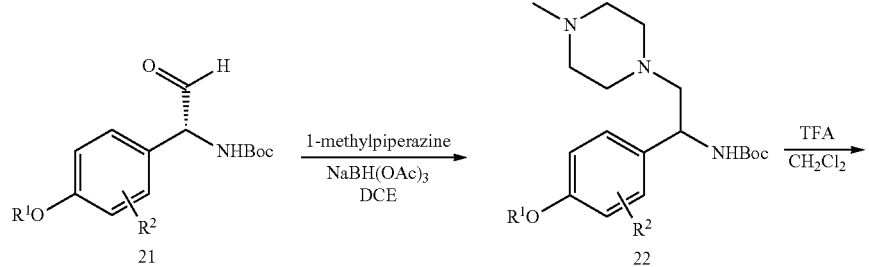

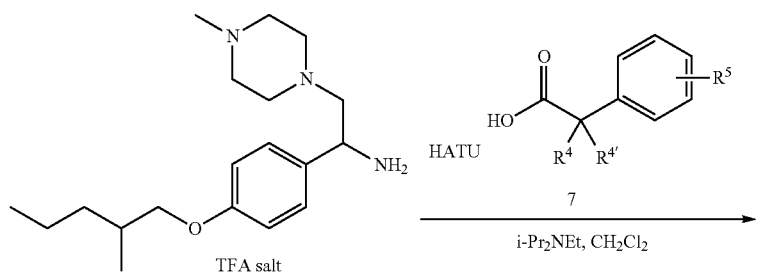

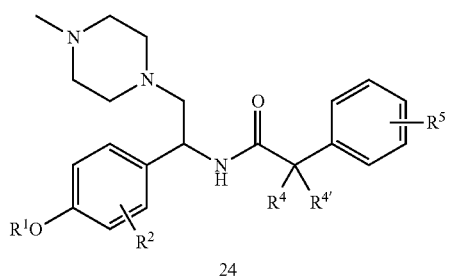

Compounds of formula 29 are prepared by the methods outlined in Scheme 6. Compound 4, prepared as described previously (vide supra) is treated with phthalimide under Mitsunobu conditions to provide compounds of formula 25. The Boc protecting group in 25 is removed with trifluoroacetic acid as described previously followed by acylation with acid chlorides of formula 26, to provide compounds of formula 27. Removal of the phthalate group is achieved with hydrazine in polar solvents to give compounds of formula 28. Compound 29 is then treated with an aldehyde (1 or more equivalents) and acetic acid in the presence of a reducing agent, such as borane-THF, in a polar solvent to provide compounds of formula 30.

Scheme 6

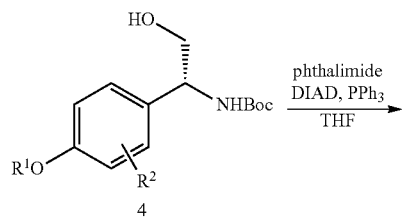

-continued

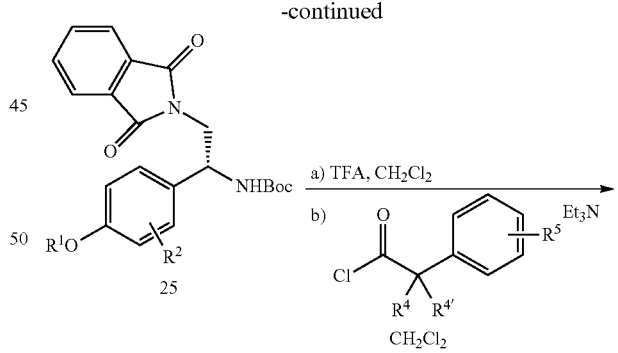

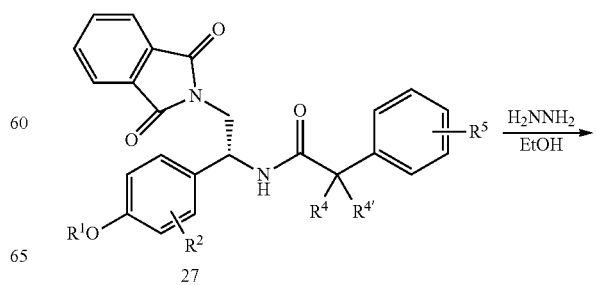

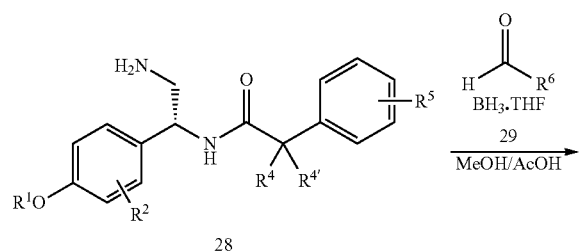

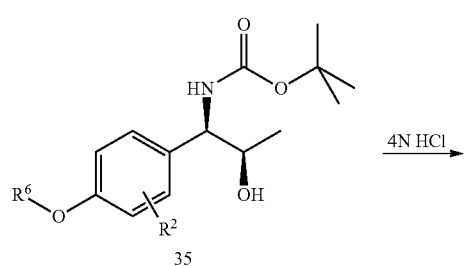

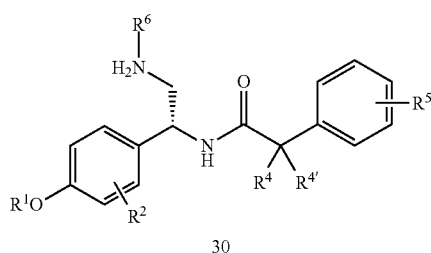

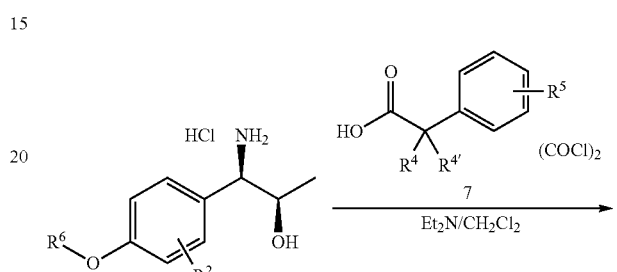

Compounds of formula 36 are prepared by the methods outlined in Scheme 7. Compound 31 is dealkylated with potassium carbonate in methanol to produce compounds of formula 32. Compound 32 is alkylated with alkylbromides of formula 33 and a base such as potassium carbonate in a polar aprotic solvent such as acetonitrile, DMF, or dichloromethane to provide compounds of formula 34. Compound 34 is then treated under Sharpless asymmetric aminohydroxylation conditions (*JACS* 1998, 1207-1217) to provide intermediate 35. The Boc protecting group in 35 is then removed with hydrochloric acid as described previously to give compounds of formula 36. Compound 36 is acylated with acids of formula 7, which are converted to acid chlorides with oxalyl chloride or thionyl chloride to give compounds of formula 37.

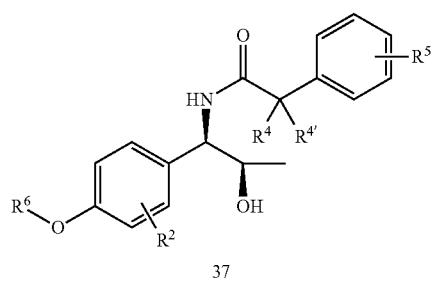

Compounds of formula 46 are prepared by the methods outlined in Scheme 8. Compound 38 is coupled with N,O-dimethylhydroxylamine using standard peptide coupling reagents such as HATU, BOP, EDC, TBTU, preferably EDC, in the presence of a base, such as N,N-diisopropylethylamine, and a solvent, such as dichloromethane to produce compounds of formula 39. Compound 39 is treated with a Grignard reagent, such as 40, to provide compounds of formula 41. Compound 41 is then treated with ammonium acetate in the presence of a reducing agent, such as sodium triacetoxyborohydride or sodium cyanoborohydride, in a polar solvent to provide intermediate 42. The resultant amine in 42 is coupled with a carboxylic acid, such as compound 7, as described previously (vide supra) to provide compounds of formula 43. Diastereomers of 43 could be separated by silica gel chromatography. The benzyl protecting group in 43 is then removed by hydrogenation in the presence of palladium on carbon to give 44. Alkylation of the hydroxyl group in 44 is achieved by treatment with an alcohol ($R^{10}H$), as described previously (vide supra) to provide compounds of formula 45. The Boc protecting group in 45 is then removed with trifluoroacetic acid as described previously to give compounds of formula 46.

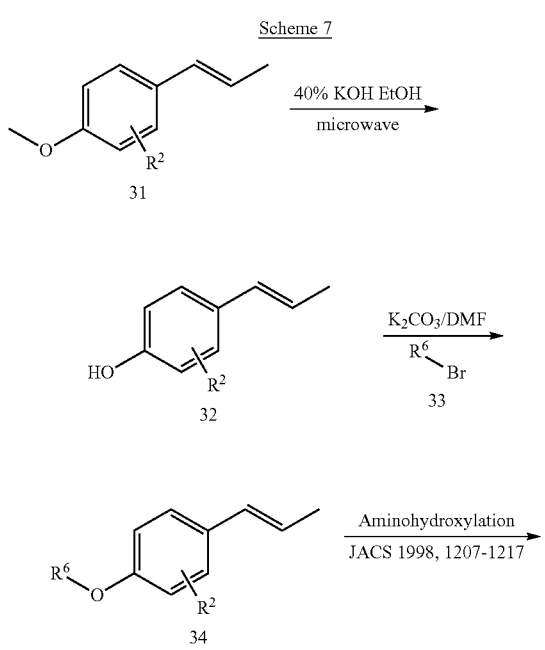

Scheme 8

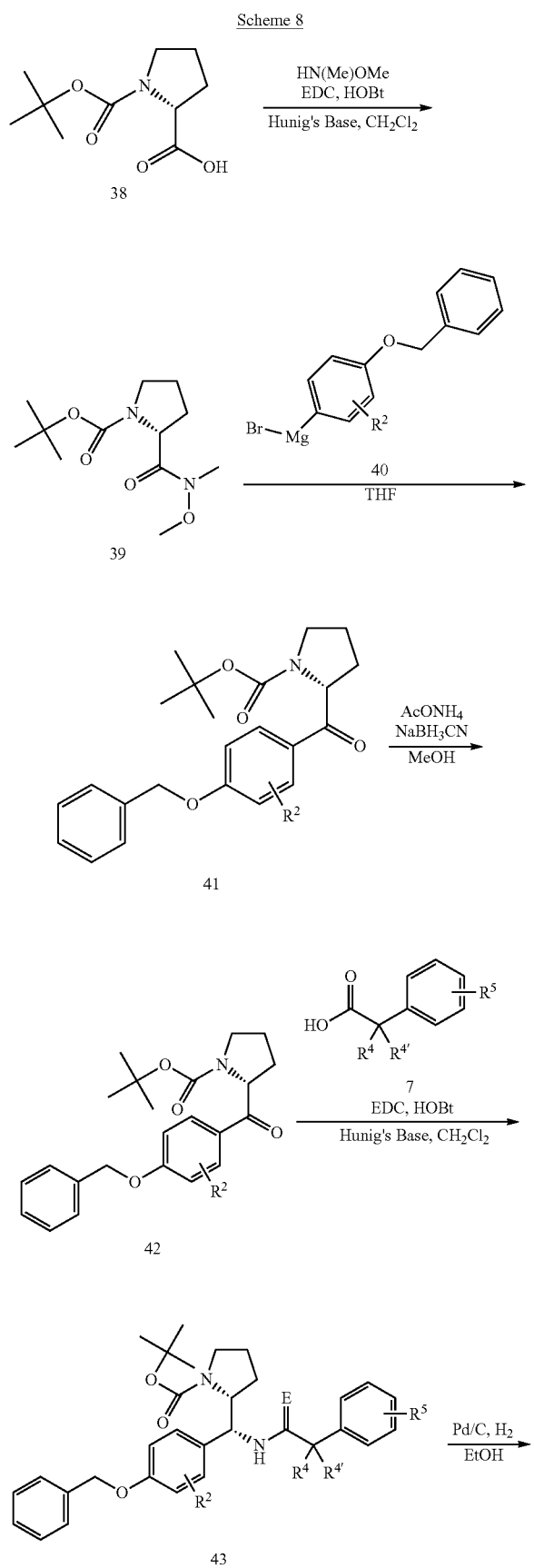
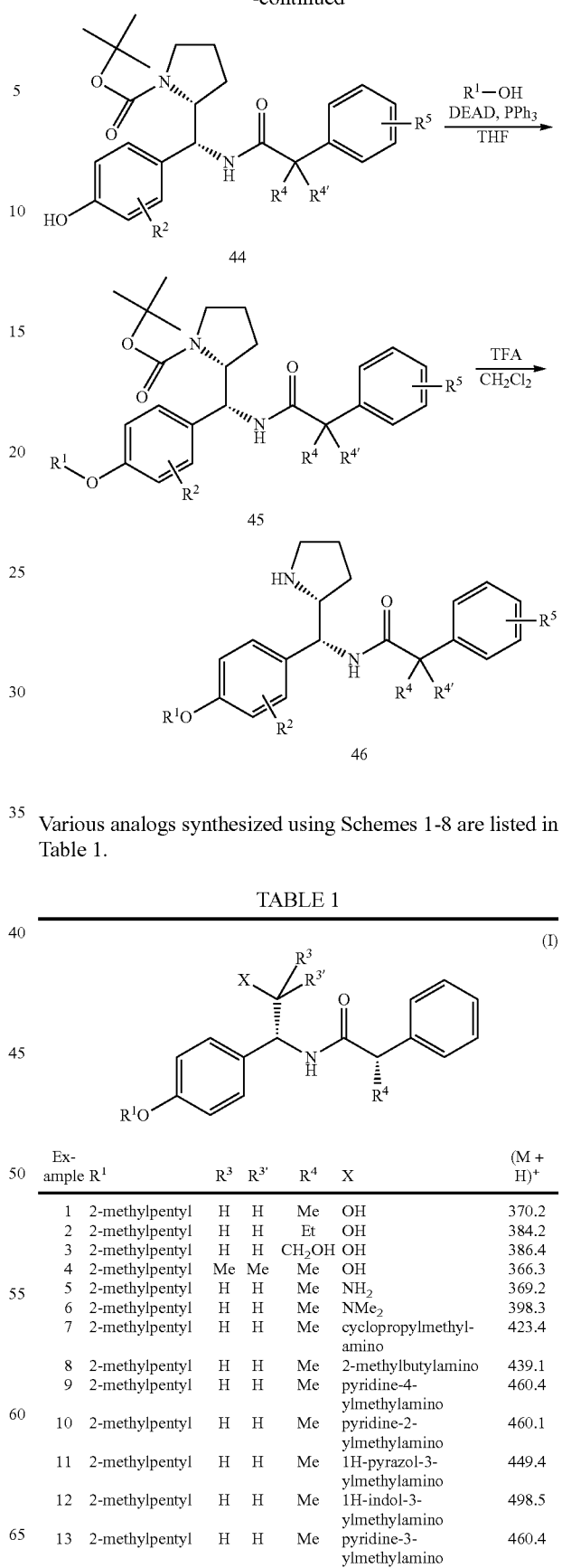

Various analogs synthesized using Schemes 1-8 are listed in Table 1.

TABLE 1

(I)

| Example | R$^1$ | R$^3$ | R$^{3'}$ | R$^4$ | X | (M + H)$^+$ |
|---|---|---|---|---|---|---|
| 1 | 2-methylpentyl | H | H | Me | OH | 370.2 |
| 2 | 2-methylpentyl | H | H | Et | OH | 384.2 |
| 3 | 2-methylpentyl | H | H | CH$_2$OH | OH | 386.4 |
| 4 | 2-methylpentyl | Me | Me | Me | OH | 366.3 |
| 5 | 2-methylpentyl | H | H | Me | NH$_2$ | 369.2 |
| 6 | 2-methylpentyl | H | H | Me | NMe$_2$ | 398.3 |
| 7 | 2-methylpentyl | H | H | Me | cyclopropylmethyl-amino | 423.4 |
| 8 | 2-methylpentyl | H | H | Me | 2-methylbutylamino | 439.1 |
| 9 | 2-methylpentyl | H | H | Me | pyridine-4-ylmethylamino | 460.4 |
| 10 | 2-methylpentyl | H | H | Me | pyridine-2-ylmethylamino | 460.1 |
| 11 | 2-methylpentyl | H | H | Me | 1H-pyrazol-3-ylmethylamino | 449.4 |
| 12 | 2-methylpentyl | H | H | Me | 1H-indol-3-ylmethylamino | 498.5 |
| 13 | 2-methylpentyl | H | H | Me | pyridine-3-ylmethylamino | 460.4 |

TABLE 1-continued (I)

[Structure: Formula (I) showing R¹O-phenyl-CH(X-C(R³)(R³'))-NH-C(=O)-CH(R⁴)-phenyl]

| Example | R¹ | R³ | R³' | R⁴ | X | (M+H)⁺ |
|---|---|---|---|---|---|---|
| 14 | 2-methylpentyl | H | H | Me | tetrahydrofuran-3-ylmethylamino | 453.4 |
| 15 | 2-methylpentyl | H | H | Me | 1-aminocyclo-pentylmethylamino | 466.5 |
| 16 | 2-methylpentyl | H | H | Me | S-pyrrolidin-2-ylmethylamino | 452.5 |
| 17 | 2-methylpentyl | H | H | Me | S-2-aminopropylamino | 426.4 |
| 18 | 2-methylpentyl | H | H | Me | R-pyrrolidin-2-ylmethylamino | 452.5 |
| 19 | 2-methylpentyl | H | H | Me | (2S,3S)-2-amino-3-methylpentanamide | 482.5 |
| 20 | 2-methylpentyl | H | H | Me | (2R)-2-amino-4-methylpentanamide | 482.6 |
| 21 | 2-methylpentyl | H | H | Me | (2S)-pyrrolidine-2-carboxamide | 466.5 |
| 22 | 2-methylpentyl | H | H | Me | (2R,3R)-2-amino-3-methyl-pentanamide | 482.6 |
| 23 | 2-methylpentyl | H | H | Me | (2S)-2-amino-propanamide | 440.5 |
| 24 | 2-methylpentyl | H | H | Me | (2S)-2-amino-3-methylbutanamide | 468.3 |
| 25 | 2-methylpentyl | H | H | Me | (2S)-2-amino-butanamide | 454.6 |
| 26 | 2-methylpentyl | H | — | Me | with R³': (S)-2-pyrrolidine | 468.3 |
| 27 | 2-methylpentyl | H | H | Me | (2S,3R)-2-amino-3-methyl-pentanamide | 482.6 |
| 28 | 2-methylpentyl | H | H | Me | (2S)-2-amino-3-cyclopropyl-propanamide | 480.3 |
| 29 | 2-methylpentyl | H | H | Me | (2R)-2-amino-propanamide | 440.5 |
| 30 | 2-methylpentyl | H | H | Me | (2S)-2-amino-2-cyclopropyl-acetamide | 466.5 |
| 31 | 2-methylpentyl | H | H | Me | (2R)-2-aminopentanamide | 468.3 |
| 32 | 2-methylpentyl | H | H | Me | (2S,3R)-2-amino-3-methoxybutanamide | 484.5 |
| 33 | 2-methylpentyl | H | H | Me | (2R,3S)-2-amino-3-methylpentanamide | 482.6 |
| 34 | 2-methylpentyl | H | H | Me | (2R)-2-amino-3-(thiazol-4-yl)propanamide | 523.5 |
| 35 | 2-methylpentyl | H | H | Me | morpholino | 439.3 |
| 36 | 2-methylpentyl | H | H | Me | 4-methylpiperazin-1-yl | 452.3 |
| 37 | (S)-2-methylbutyl | H | H | Me | NH₂ | 355.1 |
| 38 | (S)-2-methylbutyl | H | H | Me | 1-propylamino | 397.3 |
| 39 | (S)-2-methylbutyl | H | Me | Me | OH | 370.4 |
| 40 | 2-methylpropyl | — | H | Me | with R³ (R)-pyrrolidin-2-yl | 381.30 |

DESCRIPTION OF THE SPECIFIC EMBODIMENTS

In the following examples, all temperatures are given in degrees Centigrade. Melting points were recorded on a Melt-emp 3.0 Laboratory Devices, Inc. capillary melting point apparatus and are uncorrected. Proton NMR spectra were recorded on either a Bruker 400 or 500 MHz NMR spectrometer. Chemical shifts are reported in δ values relative to tetramethylsilane. Atmosphere pressure chemical ionization (APCI) low-resolution mass spectra were obtained on a Finnigan Navigator LC/MS single quadruple mass spectrometer. Low resolution mass spectra (MS) and the apparent molecular (M+H)⁺ or (M−H)⁻ was determined on a Finnegan SSQ7000. Electrospray ionization (ESI) high-resolution mass spectra were obtained on a Finnigan MAT95S reverse geometry sector instrument. Liquid chromatography (LC)/mass spectra were run on a Shimadzu LC coupled to a Waters Micromass ZQ. HPLC retention times were using one of the following four methods:

Method A: Waters Xterra C18 column, 2.1 mm×50 mm, 5 μm; λ=220 nM; Mobile Phase: A=5:95 acetonitrile:water; B=95:5 acetonitrile:water; modifier=10 mM NH₄OAc; 0% B→100% B, 4 min;

Method B: Phenomenex Gemini C18 column, 4.6 mm×150 mm 3.5 μm; λ=220 nM, Mobile Phase: A=5:95 acetonitrile:water; B=95:5 acetonitrile:water; modifier=10 mM NH₄OAc; 30% B→95% B, 12 min;

Method C: Phenomenex Gemini C18 column, 4.6 mm×500 mm, 3.0 μm; λ=220 nM, Mobile Phase: A=water; B=acetonitrile; modifier=0.1% TFA; 10% B→95% B, 10 min;

Method D: Waters Sunfire C18 column, 4.6 mm×150 mm 3.0 μm; λ=220 nM, Mobile Phase: A=water; B=acetonitrile; modifier=0.1% TFA; 40% B→95% B, 12 min.

The following abbreviations are used: THF (tetrahydrofuran), TFA (trifluoroacetic acid), Boc (t-butoxycarbonyl), HPLC (high pressure liquid chromatography).

EXAMPLE 1

(2S)-N-((1R)-2-Hydroxy-1-(4-(2-methylpentyloxy)phenyl)ethyl)-2-phenylpropanamide

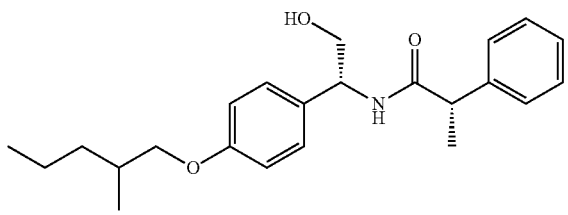

Part A. (R)-Methyl 2-(tert-butoxycarbonylamino)-2-(4-hydroxyphenyl)acetate

To a suspension of (R)-methyl 2-amino-2-(4-hydroxyphenyl)acetate.HCl (20.0 g, 92 mmol) in dichloromethane (700 mL) at 0° C. was added N,N-diisopropylethylamine (48.1 mL, 276 mmol) followed by di-t-butyldicarbonate (21.34 mL, 92 mmol) via syringe. The cooling bath was removed and the reaction mixture was stirred at room temperature overnight under nitrogen. The reaction mixture was transferred to a separatory funnel containing saturated aqueous NH₄Cl solution (200 mL). The layers were separated and the aqueous layer was extracted with ethyl acetate (3×200 mL). The combined organic layers were washed with brine (200 mL), dried over MgSO₄, filtered and concentrated. The residue was purified by column chromatography on silica gel (20%→40% ethyl acetate in hexanes) to afford (R)-methyl 2-(tert-butoxycarbonylamino)-2-(4-hydroxyphenyl)acetate (23.22 g, 86% yield) as a colorless solid: mp 140.5-141.7° C.; $^1$H NMR (400 MHz, DMSO-d$_6$) δ 9.48 (s, 1H), 7.61 (d, J=7.8 Hz, 1H), 7.16 (d, J=8.6 Hz, 2H), 6.70 (d, J=8.6 Hz, 2H), 5.05 (d, J=8.1 Hz, 1H), 3.59 (s, 3H), 1.38 (s, 9H); LRMS (ESI) m/e 282.3 [(M+H)$^+$, calcd for C$_{14}$H$_{20}$NO$_5$ 282.1].

Part B. (2R)-Methyl 2-(tert-butoxycarbonylamino)-2-(4-(2-methylpentyloxy)phenyl)acetate (R)-methyl 2-(tert-butoxycarbonylamino)-2-(4-hydroxyphenyl)acetate (23.00 g, 82 mmol), 2-methylpentan-1-ol (16.70 g, 163 mmol), and triphenylphosphine (36.46 g, 139 mmol) were combined in tetrahydrofuran (600 mL). After stirring 10 min, diethylazodicarboxylate (21.9 mL, 138 mmol) was added via syringe at room temperature. The reaction was mildly exothermic resulting in the temperature rising to the mid thirties ° C. during the addition. Intermittent cooling with a tap water bath was used to prevent the reaction mixture temperature from rising higher than this, but it was not cooled down to room temperature during the addition. After the addition was complete, the mixture was stirred at room temperature for 18 h. The reaction mixture was transferred to a separatory funnel containing water (400 mL). The aqueous layer was extracted with ether (3×400 mL). The combined organic layers were washed with brine (250 mL), dried over MgSO$_4$, filtered and concentrated. The crude product was taken up in ether (ca. 800 mL) and was stirred for 30 min. The mixture was filtered through a pad of diatomaceous earth (Celite®) to remove most of the triphenylphosphine oxide and the filtrate was concentrated. The residue was purified by column chromatography on silica gel (20% ethyl acetate in hexanes) to afford (2R)-methyl 2-(tert-butoxycarbonylamino)-2-(4-(2-methylpentyloxy)phenyl)acetate (29.43 g, 98% yield) as a colorless oil: $^1$H NMR (400 MHz, CDCl$_3$) δ 7.20-7.29 (m, 2H), 6.84 (d, J=8.6 Hz, 2H), 5.45 (d, J=6.5 Hz, 1H), 5.22 (d, J=7.3 Hz, 1H), 3.77 (dd, J=9.1, 5.8 Hz, 1H), 3.69 (s, 3H), 3.65-3.70 (m, 1H), 1.85-1.96 (m, 1H), 1.41 (s, 9H), 1.14-1.50 (m, 4H), 0.98 (d, J=6.8 Hz, 3H), 0.90 (t, J=7.1 Hz, 3H); LRMS (ESI) m/e 366.4 [(M+H)$^+$, calcd for C$_{20}$H$_{32}$NO$_5$ 366.2].

Part C. t-Butyl (1R)-2-hydroxy-1-(4-(2-methylpentyloxy)phenyl)ethylcarbamate To a suspension of sodium borohydride (1.346 g, 35.6 mmol) in ethanol (50 mL) at 0° C. was added lithium chloride (1.508 g, 35.6 mmol). The mixture was stirred at 0° C. for 10 min. A solution of (2R)-methyl 2-(tert-butoxycarbonylamino)-2-(4-(2-methylpentyloxy)phenyl)acetate (5.00 g, 13.68 mmol) in tetrahydrofuran (50.0 mL) was then added via cannula. The reaction mixture was warmed up to room temperature and was stirred at room temperature for 3 h. The reaction mixture was cooled to 0° C. and was quenched by the slow addition of saturated aqueous NH$_4$Cl solution (30 mL). The reaction mixture was transferred to a separatory funnel containing water (50 mL). The aqueous layer was extracted with ethyl acetate (3×150 mL). The combined organic layers were washed with brine (50 mL), dried over MgSO$_4$, filtered and concentrated. The residue was purified by column chromatography on silica gel (30%→45% ethyl acetate in hexanes) to afford t-butyl (1R)-2-hydroxy-1-(4-(2-methylpentyloxy)phenyl)ethylcarbamate (4.24 g, 92% yield) as a colorless solid: $^1$H NMR (400 MHz, DMSO-d$_6$) δ 7.17 (d, J=8.6 Hz, 2H), 7.12 (d, J=8.3 Hz, 1H), 6.84 (d, J=8.6 Hz, 2H), 4.72 (t, J=5.8 Hz, 1H), 4.44 (q, J=6.8 Hz, 1H), 3.79 (dd, J=9.3, 5.8 Hz, 1H), 3.70 (dd, J=9.3, 6.5 Hz, 1H), 3.37-3.49 (m, 2H), 1.80-1.92 (m, 1H), 1.36 (s, 9H), 1.23-1.47 (m, 3H), 1.13-1.21 (m, 1 H), 0.95 (d, J=6.5 Hz, 3H), 0.88 (t, J=7.1 Hz, 3H); LRMS (ESI) m/e 338.2 [(M+H)$^+$, calcd for C$_{19}$H$_{32}$NO$_4$ 338.2].

Part D. (2R)-2-(tert-Butoxycarbonylamino)-2-(4-(2-methylpentyloxy)phenyl)ethyl acetate To a solution of (1R)-2-hydroxy-1-(4-(2-methylpentyloxy)phenyl)ethylcarbamate (5.00 g, 14.82 mmol) and triethylamine (10.33 mL, 74.1 mmol) in tetrahydrofuran (50 mL) at 0° C. was added DMAP (1.99 g, 16.30 mmol). Acetyl chloride (4.21 mL, 59.3 mmol) was then added slowly via syringe. After the addition was complete, the cooling bath was removed and the mixture was stirred at room temperature under N$_2$ for 2 h. The reaction mixture was transferred to a separatory funnel containing saturated aqueous NaHCO$_3$ solution (50 mL). The aqueous layer was extracted with ethyl acetate (3×100 mL). The combined organic layers were washed with brine (50 mL), dried over MgSO$_4$, filtered and concentrated. The residue was purified by column chromatography on silica gel (15%→25% ethyl acetate in hexanes) to afford (2R)-2-(tert-butoxycarbonylamino)-2-(4-(2-methylpentyloxy)phenyl)ethyl acetate (5.50 g, 98% yield) as a colorless amorphous solid: $^1$H NMR (400 MHz, DMSO-d$_6$) δ 7.44 (d, J=9.1 Hz, 1H), 7.23 (d, J=8.8 Hz, 2H), 6.88 (d, J=8.6 Hz, 2H), 4.67-4.78 (m, 1H), 4.10 (dd, J=10.8, 5.3 Hz, 1H), 3.98 (dd, J=10.6, 9.1 Hz, 1H), 3.80 (dd, J=9.6, 6.0 Hz, 1H), 3.71 (dd, J=9.3, 6.8 Hz, 1H), 1.97 (s, 3H), 1.86 (dq, J=12.8, 6.5 Hz, 1H), 1.37 (s, 9 H), 1.22-1.47 (m, 3H), 1.11-1.22 (m, 1H), 0.96 (d, J=6.8 Hz, 3H), 0.88 (t, J=7.2 Hz, 3H); LRMS (ESI) m/e 380.3 [(M+H)$^+$, calcd for C$_{21}$H$_{34}$NO$_5$ 380.3].

Part E. (2R)-2-Amino-2-(4-(2-methylpentyloxy)phenyl)ethyl acetate

A solution of (2R)-2-(t-butoxycarbonylamino)-2-(4-(2-methylpentyloxy)phenyl)ethyl acetate (5.50 g, 14.49 mmol) in 2 M HCl in ether (72.5 mL, 144.9 mmol) was stirred at room temperature for 12 h. The precipitate formed was collected on a Buchner funnel, washed with ether, and dried under vacuum to afford (2R)-2-amino-2-(4-(2-methylpentyloxy)phenyl)ethyl acetate.HCl (3.70 g, 81% yield) as a tan solid: $^1$H NMR (400 MHz, DMSO-d$_6$) δ 8.80 (br. s., 3 H), 7.46 (d, J=8.8 Hz, 2H), 6.98 (d, J=8.8 Hz, 2H), 4.43-4.55 (m, 1H), 4.25-4.37 (m, 2H), 3.84 (dd, J=9.6, 6.0 Hz, 1H), 3.74 (dd, J=9.6, 6.8 Hz, 1H), 2.05 (s, 3H), 1.81-1.93 (m, 1H), 1.25-1.49 (m, 3H), 1.10-1.23 (m, 1H), 0.96 (d, J=6.5 Hz, 3H), 0.88 (t, J=7.1 Hz, 3H); LRMS (ESI) m/e 280.4 [(M+H)$^+$, calcd for C$_{16}$H$_{26}$NO$_3$ 280.2].

Part F. (2R)-2-(4-(2-Methylpentyloxy)phenyl)-2-((S)-2-phenylpropanamido)ethyl acetate To a solution of (2R)-2-amino-2-(4-(2-methylpentyloxy)phenyl)ethyl acetate.HCl (400 mg, 1.432 mmol) and (S)-2-phenylpropanoic acid (323 mg, 2.15 mmol) in tetrahydrofuran (8 mL) at 0° C. was added N,N-diisopropylethylamine (0.875 mL, 5.01 mmol) followed by HATU (817 mg, 2.15 mmol). The cooling bath was removed and the mixture was stirred at room temperature under N$_2$ overnight. The reaction mixture was transferred to a separatory funnel containing saturated aqueous NaHCO$_3$ solution (25 mL). The aqueous layer was extracted with ethyl acetate (3×25 mL). The combined organic layers were washed with brine (25 mL), dried over MgSO$_4$, filtered and concentrated. The residue was purified by column chromatography on silica gel (30%→45% ethyl acetate in hexanes; 40 g column) and dried under vacuum to afford (2R)-2-(4-(2-methylpentyloxy)phenyl)-2-((S)-2-phenylpropanamido)ethyl acetate (430 mg, 73.0% yield) as a colorless solid: $^1$H NMR (400 MHz, CDCl$_3$) δ 7.22-7.37 (m, 5H), 6.95 (d, J=8.6 Hz, 2H), 6.76 (d, J=8.8 Hz, 2H), 5.87 (d, J=8.1 Hz, 1H), 5.16 (td, J=7.7, 4.5 Hz, 1H), 4.25 (dd, J=11.5, 7.4 Hz, 1H), 4.14 (dd, J=11.3, 4.5 Hz, 1H), 3.74 (dd, J=8.8, 5.8 Hz, 1H), 3.65 (dd, J=8.8, 6.8 Hz, 1H), 3.59 (q, J=7.1 Hz, 1H), 1.95 (s, 3H), 1.85-1.95 (m, 1H), 1.49 (d, J=7.3 Hz, 3H), 1.24-1.47 (m, 3H), 1.13-1.23 (m, 1H), 0.97 (d, J=6.8 Hz, 3H), 0.90 (t, J=7.3 Hz, 3H); LRMS (ESI) m/e 412.2 [(M+H)$^+$, calcd for C$_{25}$H$_{34}$NO$_4$ 412.3].

Part G. (2S)-N-((1R)-2-Hydroxy-1-(4-(2-methylpentyloxy)phenyl)ethyl)-2-phenylpropanamide To a solution of (2R)-2-(4-(2-methylpentyloxy)phenyl)-2-((S)-2-phenylpropanamido)ethyl acetate (358 mg, 0.870 mmol) in methanol (5 mL) at 0° C. was added sodium methoxide (14.0 mL, 7.00 mmol). The cooling bath was removed and the mixture was stirred at room temperature for 20 min. Saturated aqueous NH$_4$Cl (5 mL) was added and the methanol was removed on the rotovapor. The mixture was transferred to a separatory funnel containing saturated aqueous NH$_4$Cl solution (20 mL). The aqueous layer was extracted with ethyl acetate (4×20 mL). The combined organic layers were washed with brine (20 mL), dried over MgSO$_4$, filtered and concentrated. The residue was purified by column chromatography on silica gel (40%→75% ethyl acetate in hexanes; 25 g column) to afford (2S)-N-((1R)-2-hydroxy-1-(4-(2-methylpentyloxy)phenyl)ethyl)-2-phenylpropanamide (269 mg, 84% yield) as a colorless solid: $^1$H NMR (400 MHz, CDCl$_3$) δ 7.29-7.36 (m, 2H), 7.22-7.29 (m, 3H), 6.94 (d, J=8.6 Hz, 2H), 6.76 (d, J=8.6 Hz, 2H), 6.01 (d, J=6.8 Hz, 1H), 4.89-4.97 (m, 1H), 3.76 (d, J=4.8 Hz, 2H), 3.71-3.75 (m, 1H), 3.59-3.68 (m, 2H), 2.46 (br. s., 1H), 1.84-1.95 (m, 1H), 1.50 (d, J=7.1 Hz, 3H), 1.25-1.48 (m, 3H), 1.13-1.22 (m, 1H), 0.97 (d, J=6.8 Hz, 3H), 0.90 (t, J=7.3 Hz, 3H); LRMS (ESI) m/e 370.2 [(M+H)$^+$, calcd for C$_{23}$H$_{32}$NO$_3$ 370.2].

EXAMPLE 2

(2S)-N-((1R)-2-Hydroxy-1-(4-(2-methylpentyloxy)phenyl)ethyl)-2-phenylbutanamide

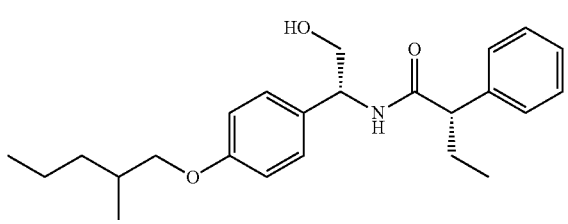

Prepared by the method described in example 1 using the appropriate starting materials to give (2S)-N-((1R)-2-hydroxy-1-(4-(2-methylpentyloxy)phenyl)ethyl)-2-phenylbutanamide as a colorless solid: $^1$H NMR (400 MHz, DMSO-d$_6$) δ 8.30 (d, J=8.3 Hz, 1H), 7.21-7.34 (m, 4H), 7.14-7.21 (m, 1H), 7.03 (d, J=8.6 Hz, 2H), 6.74 (d, J=8.6 Hz, 2H), 4.83 (br. s., 1H), 4.74-4.81 (m, 1H), 3.74 (dd, J=9.3, 5.8 Hz, 1H), 3.65 (dd, J=9.1, 6.8 Hz, 1H), 3.41-3.55 (m, 3H), 1.90-2.04 (m, 1H), 1.83 (dq, J=12.4, 6.3 Hz, 1H), 1.62 (dt, J=13.6, 6.8 Hz, 1H), 1.21-1.46 (m, 3H), 1.05-1.20 (m, 1H), 0.93 (d, J=6.8 Hz, 3H), 0.87 (t, J=7.3 Hz, 3H), 0.85 (t, J=7.3 Hz, 3H); LRMS (ESI) m/e 384.2 [(M+H)$^+$, calcd for C$_{24}$H$_{34}$NO$_3$ 384.3].

EXAMPLE 3

(2R)-3-Hydroxy-N-((1R)-2-hydroxy-1-(4-(2-methylpentyloxy)phenyl)ethyl)-2-phenylpropanamide

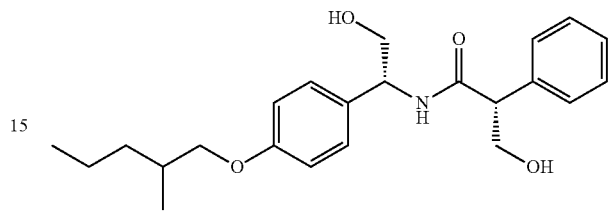

Prepared by the method described in example 1 using the appropriate starting materials to give (2R)-3-hydroxy-N-((1R)-2-hydroxy-1-(4-(2-methylpentyloxy)phenyl)ethyl)-2-phenylpropanamide: HPLC t$_R$=7.53 min (Method D), LRMS (ESI) m/e 386.4 [(M+H)$^+$, calcd for C$_{23}$H$_{32}$NO$_4$ 386.3].

EXAMPLE 4

(2S)-N-((1R)-2-Hydroxy-2-methyl-1-(4-(2-methylpentyloxy)phenyl)propyl)-2-phenylpropanamide

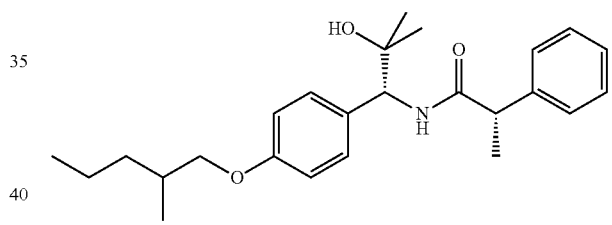

Part A. t-Butyl (1R)-2-hydroxy-2-methyl-1-(4-(2-methylpentyloxy)phenyl)propylcarbamate (2R)-methyl 2-(tert-butoxycarbonylamino)-2-(4-(2-methylpentyloxy)phenyl)acetate (500 mg, 1.368 mmol), prepared according to the procedure described in example 1, was dissolved in anhydrous tetrahydrofuran (10 mL) and the solution was cooled to 0° C. A 3 molar solution of methylmagnesium bromide in ether (1.459 mL, 4.38 mmol) was added dropwise. The mixture was then warmed to room temperature and was stirred for 5 h. The reaction was quenched with saturated aqueous NH$_4$Cl (10 mL) and the mixture was filtered through a pad of diatomaceous earth (Celite®). The filtrate was concentrated and the residue was purified by column chromatography (30→40% ethyl acetate in hexanes, 40 g column) to afford t-butyl (1R)-2-hydroxy-2-methyl-1-(4-(2-methylpentyloxy)phenyl)propylcarbamate (340 mg, 68% yield) as a yellow oil: $^1$H NMR (400 MHz, CDCl$_3$) δ 7.16 (d, 2H), 6.83 (d, J=8.8 Hz, 2H), 5.42 (d, J=6.5 Hz, 1H), 4.45 (d, J=7.8 Hz, 1H), 3.78 (dd, J=9.1, 5.8 Hz, 1H), 3.68 (dd, J=8.9, 6.7 Hz, 1H), 1.86-1.97 (m, 1H), 1.64 (br. s., 1H), 1.39 (br. s., 9H), 1.29 (s, 3H), 1.27-1.50 (m, 3H), 1.14-1.24 (m, 1H), 1.04 (s, 3H), 0.99 (d, J=6.5 Hz, 3H), 0.90 (t, J=7.2 Hz, 3H); LRMS (ESI) m/e 366.3 [(M+H)$^+$, calcd for C$_{21}$H$_{36}$NO$_4$ 366.3].

Part B. (1R)-1-Amino-2-methyl-1-(4-(2-methylpentyloxy)phenyl)propan-2-ol

To a solution of t-butyl (1R)-2-hydroxy-2-methyl-1-(4-(2-methylpentyloxy)phenyl)-propylcarbamate (340 mg, 0.930 mmol) in dichloromethane (1 mL) was added TFA (2 mL, 26.0 mmol). The reaction mixture was stirred at room temperature for 1 h. The solvent was evaporated and the residue was transferred to a separatory funnel containing saturated aqueous $K_2CO_3$ solution. The aqueous layer was extracted with ethyl acetate (2×10 mL). The combined organic layers were concentrated to afford (1R)-1-amino-2-methyl-1-(4-(2-methylpentyloxy)phenyl)propan-2-ol.TFA (350 mg, 99% yield) as a colorless oil which was used directly in the next step: $^1$H NMR (400 MHz, $CDCl_3$) δ 7.20 (d, J=8.6 Hz, 2H), 6.82 (d, J=8.8 Hz, 2H), 3.78 (dd, J=9.1, 5.8 Hz, 1H), 3.73 (s, 1H), 3.68 (dd, J=8.9, 6.7 Hz, 1H), 1.86-1.97 (m, 1H), 1.27-1.51 (m, 4H), 1.17 (s, 3H), 1.01 (s, 3H), 0.99 (d, J=6.8 Hz, 3H), 0.90 (t, J=7.3 Hz, 3H).

Part C. (2S)-N-((1R)-2-Hydroxy-2-methyl-1-(4-(2-methyl-pentyloxy)phenyl)propyl)-2-phenylpropanamide A solution of (1R)-1-amino-2-methyl-1-(4-(2-methylpentyloxy)phenyl)propan-2-ol.TFA (100 mg, 0.264 mmol) in dichloromethane (4 mL) was cooled to 0° C. To this solution (S)-2-phenylpropanoic acid (0.043 mL, 0.316 mmol), N,N-diisopropylethylamine (0.276 mL, 1.581 mmol) and HATU (120 mg, 0.316 mmol) were added. The ice-water bath was removed and reaction mixture was stirred at room temperature for 3 h. The reaction mixture was transferred to a separatory funnel containing saturated aqueous $NaHCO_3$ solution (60 mL). The aqueous layer was extracted with ethyl acetate (3×50 mL). The combined organic layers were washed with brine (20 mL), dried over $MgSO_4$, filtered and concentrated. The residue was purified by column chromatography on silica gel (30%→40% ethyl acetate in hexanes) to afford (2S)-N-((1R)-2-hydroxy-2-methyl-1-(4-(2-methylpentyloxy)phenyl)propyl)-2-phenylpropanamide (73 mg, 70% yield) as a colorless solid: $^1$H NMR (400 MHz, $CDCl_3$) δ 7.17-7.34 (m, 5H), 6.92 (d, J=8.8 Hz, 2H), 6.74 (d, J=8.8 Hz, 2H), 6.29 (d, J=8.6 Hz, 1H), 4.68 (d, J=8.6 Hz, 1H), 3.75 (dd, J=8.8, 5.8 Hz, 1H), 3.59-3.68 (m, 2H), 1.90 (dq, J=12.9, 6.4 Hz, 1H), 1.74 (s, 1H), 1.47 (d, J=7.1 Hz, 3H), 1.26-1.51 (m, 3H), 1.18 (s, 3H), 1.14-1.26 (m, 1 H), 0.98 (d, J=6.5 Hz, 3H), 0.96 (s, 3H), 0.90 (t, J=7.3 Hz, 3H); LRMS (ESI) m/e 398.2 [(M+H)$^+$, calcd for $C_{25}H_{36}NO_3$ 398.3].

EXAMPLE 5

(2S)-N-((1R)-2-Amino-1-(4-(2-methylpentyloxy)phenyl)ethyl)-2-phenylpropanamide

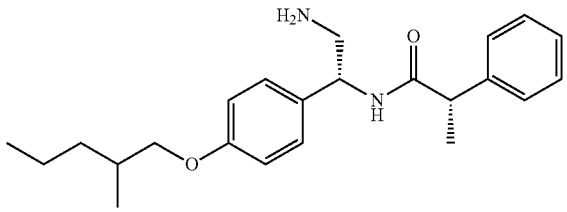

Part A. t-Butyl (1R)-2-bromo-1-(4-(2-methylpentyloxy)phenyl)ethylcarbamate

To a solution of t-butyl (1R)-2-hydroxy-1-(4-(2-methylpentyloxy)phenyl)ethylcarbamate (15 g, 44.5 mmol), prepared according to the procedure described in example 1, in anhydrous tetrahydrofuran (200 mL) was added triphenylphosphine (17.49 g, 66.7 mmol) and carbon tetrabromide (22.11 g, 66.7 mmol). The reaction mixture was stirred at room temperature for 2 h. The mixture was filtered through a pad of diatomaceous earth (Celite®) and the filtrate was concentrated to afford yellow residue which was purified by column chromatography on silica gel (20→30% ethyl acetate in hexanes) to afford t-butyl (1R)-2-bromo-1-(4-(2-methylpentyloxy)phenyl)ethylcarbamate (17.8 g, 100% yield) as a colorless solid: $^1$H NMR (400 MHz, $CDCl_3$) δ 7.18 (d, J=8.8 Hz, 2H), 6.86 (d, J=8.6 Hz, 2H), 5.05 (br. s., 1H), 4.91 (br. s., 1H), 3.78 (dd, J=8.8, 5.8 Hz, 1H), 3.68 (dd, J=9.1, 6.8 Hz, 1H), 3.65 (d, J=5.0 Hz, 1H), 1.86-1.97 (m, 1H), 1.60 (d, J=7.3 Hz, 1H), 1.42 (s, 9H), 1.14-1.51 (m, 4H), 0.99 (d, J=6.5 Hz, 3H), 0.90 (t, J=7.3 Hz, 3H); LRMS (ESI) m/e 400.2 [(M+H)$^+$, calcd for $C_{19}H_{31}NO_3Br$ 400.1].

Part B. t-Butyl (1R)-2-azido-1-(4-(2-methylpentyloxy)phenyl)ethylcarbamate

To a solution of t-butyl (1R)-2-bromo-1-(4-(2-methylpentyloxy)phenyl)ethylcarbamate (17.8 g, 44.5 mmol) in dimethylformamide was added sodium azide (11.56 g, 178 mmol) and the reaction mixture was stirred at room temperature for 1 h. The reaction was quenched by addition of water (25 mL) and the mixture was transferred to a separatory funnel and the aqueous layer was extracted with dichloromethane (3×40 mL). The combined organic layers were washed with brine (25 mL), dried over $MgSO_4$, filtered and concentrated. The residue was purified by column chromatography on silica gel (30→40% ethyl acetate in hexanes) to afford t-butyl (1R)-2-azido-1-(4-(2-methylpentyloxy)phenyl)ethylcarbamate (14.2 g, 88% yield) as a yellow solid: $^1$H NMR (400 MHz, $CDCl_3$) δ 7.19 (d, J=8.6 Hz, 2H), 6.86 (d, J=8.8 Hz, 2H), 5.01 (d, J=7.8 Hz, 1H), 4.78 (br. s., 1H), 3.78 (dd, J=9.1, 5.8 Hz, 1H), 3.68 (dd, J=8.8, 6.5 Hz, 1H), 3.57 (d, J=4.8 Hz, 2H), 1.86-1.97 (m, 1H), 1.42 (s, 9H), 1.26-1.51 (m, 3H), 1.14-1.24 (m, 1H), 0.99 (d, J=6.5 Hz, 3H), 0.90 (t, J=7.2 Hz, 3 H); LRMS (ESI) m/e 363.3 [(M+H)$^+$, calcd for $C_{19}H_{31}N_4O_3Br$ 363.2].

Part C. (1R)-2-Azido-1-(4-(2-methylpentyloxy)phenyl)ethanamine

To a solution of t-butyl (1R)-2-azido-1-(4-(2-methylpentyloxy)phenyl)ethylcarbamate (14.2 g, 39.2 mmol) in dichloromethane (2 mL) was added trifluoroacetic acid (18.1 mL, 235 mmol). The reaction mixture was stirred at room temperature for 1 h. The mixture was concentrated and the residue was transferred to a separatory funnel containing saturated aqueous $K_2CO_3$ solution. The aqueous layer was extracted with ethyl acetate (3×50 mL). The combined organic layers were dried over $MgSO_4$, filtered and concentrated to afford (1R)-2-azido-1-(4-(2-methylpentyloxy)phenyl)ethanamine (9 g, 88% yield) as a yellow oil: $^1$H NMR (400 MHz, DMSO-d$_6$) δ 7.29 (d, J=8.8 Hz, 2H), 6.88 (d, J=8.6 Hz, 2H), 3.96 (t, J=6.4 Hz, 1H), 3.80 (dd, J=9.1, 5.5 Hz, 1H), 3.71 (dd, J=9.2, 6.7 Hz, 1H), 3.29-3.39 (m, 2H), 2.59-2.75 (m, 2H), 1.86 (dq, J=12.8, 6.5 Hz, 1H), 1.25-1.48 (m, 3H), 1.12-1.22 (m, 1H), 0.95 (d, J=6.8 Hz, 3H), 0.88 (t, J=7.1 Hz, 3H); HRMS (ESI) m/e 263.1860 [(M+H)$^+$, calcd for $C_{14}H_{23}N_4O$ 263.1872].

Part D. (2S)-N-((1R)-2-Azido-1-(4-(2-methylpentyloxy)phenyl)ethyl)-2-phenylpropanamide A solution of (1R)-2-azido-1-(4-(2-methylpentyloxy)phenyl)ethanamine (9.0 g, 34.3 mmol) in dichloromethane (100 mL) was cooled to 0° C. To this solution, (S)-2-phenylpropanoic acid (7.0 mL, 51.5 mmol), N,N-diisopropylethylamine (35.9 mL, 206 mmol) and HATU (19.57 g, 51.5 mmol) were added. The ice bath was removed and reaction mixture was stirred at room temperature for 3 h. The reaction mixture was transferred to a separatory funnel containing saturated aqueous NaHCO$_3$ solution (60 mL). The aqueous layer was extracted with ethyl acetate (3×50 mL). The combined organic layers were washed with brine (25 mL), dried over MgSO$_4$, filtered and concentrated. The residue was purified by column chromatography on silica gel (30→40% ethyl acetate in hexanes) to afford (2S)-N-((1R)-2-azido-1-(4-(2-methylpentyloxy)phenyl)ethyl)-2-phenylpropanamide (12.5 g, 92% yield) as a colorless solid: $^1$H NMR (400 MHz, CDCl$_3$) δ 7.21-7.34 (m, 5H), 6.98 (d, J=8.6 Hz, 2H), 6.78 (d, J=8.8 Hz, 2H), 6.37 (d, J=8.1 Hz, 1H), 5.10 (ddd, J=7.9, 5.8, 5.7 Hz, 1H), 3.76 (dd, J=9.1, 5.8 Hz, 1H), 3.61-3.70 (m, 2H), 3.46-3.56 (m, 2H), 1.87-1.98 (m, 1H), 1.52 (d, J=7.3 Hz, 3H), 1.26-1.51 (m, 3H), 1.21 (dddd, J=12.3, 7.6, 5.3, 5.0 Hz, 1H), 1.01 (d, J=6.5 Hz, 3H), 0.93 (t, J=7.1 Hz, 3H); LRMS (ESI) m/e 395.3 [(M+H)$^+$, calcd for C$_{23}$H$_{31}$N$_4$O$_2$ 395.3].

Part E. (2S)-N-((1R)-2-Amino-1-(4-(2-methylpentyloxy)phenyl)ethyl)-2-phenylpropanamide To a solution of (2S)-N-((1R)-2-azido-1-(4-(2-methylpentyloxy)phenyl)ethyl)-2-phenylpropanamide (12.0 g, 30.4 mmol) in ethanol (40 mL) in a Parr shaker bottle was added 10% Pd/C (3.0 g, 2.82 mmol, Degussa type). The reaction mixture was placed under an H$_2$ atmosphere at 40 psi for 1 h. The mixture was then filtered through a pad of diatomaceous earth (Celite®) and the filtrate was concentrated. The residue was purified by column chromatography on silica gel (10% methanol in dichloromethane) to afford (2S)-N-((1R)-2-amino-1-(4-(2-methylpentyloxy)phenyl)ethyl)-2-phenylpropanamide (7.0 g, 63% yield) as an off-white solid: $^1$H NMR (400 MHz, DMSO-d$_6$) δ 8.22 (d, J=8.1 Hz, 1H), 7.22-7.31 (m, 4H), 7.13-7.22 (m, 1H), 6.99 (d, 2H), 6.74 (d, 2H), 4.56-4.70 (m, 1H), 3.69-3.79 (m, 2H), 3.65 (dd, J=9.3, 6.5 Hz, 1H), 3.34 (br. s., 2H), 2.61-2.75 (m, 2H), 1.83 (dddd, J=12.5, 6.5, 6.4, 6.3 Hz, 1H), 1.33-1.36 (m, 3H), 1.24-1.48 (m, 3H), 1.10-1.20 (m, 1H), 0.93 (d, J=6.8 Hz, 3H), 0.87 (t, J=7.1 Hz, 3H); LRMS (ESI) m/e 369.2 [(M+H)$^+$, calcd for C$_{23}$H$_{33}$N$_2$O$_2$ 369.3].

EXAMPLE 6

(2S)-N-((1R)-2-(Dimethylamino)-1-(4-(2-methylpentyloxy)phenyl)ethyl)-2-phenylpropanamide

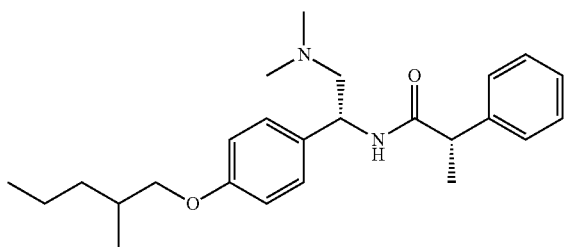

To a stirred solution of (2S)-N-((1R)-2-amino-1-(4-(2-methylpentyloxy)phenyl)ethyl)-2-phenylpropanamide (100 mg, 0.271 mmol), prepared according to the procedure described in example 5, in acetonitrile (2 mL) was added formaldehyde (0.04 mL, 0.543 mmol, 37% aqueous solution). After stirring for 15 min, sodium triacetoxyborohydride (230 mg, 1.085 mmol) was added and the reaction mixture was stirred at room temperature for 1 h. The reaction mixture was transferred to a separatory funnel containing saturated aqueous NaHCO$_3$ (10 mL). The aqueous layer was extracted with ethyl acetate (2×20 mL). The combined organic layers were washed with brine, dried over MgSO$_4$, filtered and concentrated. The residue was purified by HPLC (acetonitrile/water with 0.1% TFA) to afford (2S)-N-((1R)-2-(dimethylamino)-1-(4-(2-methylpentyloxy)phenyl)ethyl)-2-phenylpropanamide.TFA (70 mg, 51% yield) as a colorless oil: $^1$H NMR (400 MHz, CDCl$_3$) δ 7.28-7.34 (m, 2H), 7.22-7.27 (m, 3H), 6.93 (d, J=8.6 Hz, 2H), 6.73 (d, J=8.8 Hz, 2H), 6.29 (d, J=4.8 Hz, 1H), 4.79 (ddd, J=10.3, 5.4, 5.2 Hz, 1H), 3.73 (dd, J=8.8, 5.8 Hz, 1H), 3.58-3.66 (m, 2H), 2.46 (dd, J=12.6, 10.3 Hz, 1H), 2.32 (dd, J=12.6, 5.3 Hz, 1H), 2.18 (s, 6H), 1.83-1.93 (m, 1H), 1.47 (d, J=7.1 Hz, 3H), 1.26-1.49 (m, 3H), 1.12-1.22 (m, 1H), 0.97 (d, J=6.8 Hz, 3H), 0.90 (t, J=7.3 Hz, 3H); LRMS (ESI) m/e 398.3 [(M+H)$^+$, calcd for C$_{25}$H$_{37}$N$_2$O$_2$ 398.3].

EXAMPLE 7

(2S)-N-((1R)-2-(Cyclopropylmethylamino)-1-(4-(2-methylpentyloxy)phenyl)ethyl)-2-phenylpropanamide

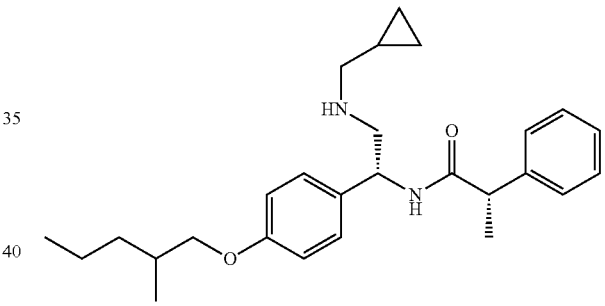

To a stirred solution of (2S)-N-((1R)-2-amino-1-(4-(2-methylpentyloxy)phenyl)ethyl)-2-phenylpropanamide (50 mg, 0.136 mmol), prepared according to the procedure described in example 5, in acetonitrile (3 mL), was added cyclopropanecarboxaldehyde (10.23 µL, 0.136 mmol) and stirring was continued for 15 min. To this mixture, sodium triacetoxyborohydride (57.5 mg, 0.271 mmol) was added and the reaction mixture was stirred at room temperature for 1 h. The reaction mixture was transferred to a separatory funnel containing saturated aqueous NaHCO$_3$ solution (10 mL). The aqueous layer was extracted with ethyl acetate (2×20 mL). The combined organic layers washed with brine, dried over MgSO$_4$, filtered and concentrated. The residue was purified by reverse phase HPLC (acetonitrile/water with 0.1% TFA). The organic solvent was removed on the rotovapor and the aqueous mixture was frozen and placed on the lyophilizer. The product was transferred to a separatory funnel containing saturated aqueous NaHCO$_3$ solution (10 mL). The aqueous layer was extracted with ethyl acetate (2×20 mL). The combined organic layers were dried over MgSO$_4$, filtered and concentrated to afford (2S)-N-((1R)-2-(cyclopropylmethylamino)-1-(4-(2-methylpentyloxy)phenyl)ethyl)-2-phenylpropanamide (25 mg, 43.6% yield) as a colorless oil: $^1$H NMR (400 MHz, CDCl$_3$) δ 7.20-7.36 (m, 5H), 6.92 (d, J=8.6

Hz, 2H), 6.73 (d, J=8.6 Hz, 2H), 6.50 (d, J=6.8 Hz, 1H), 4.99 (q, J=6.3 Hz, 1H), 3.74 (dd, J=8.8, 5.8 Hz, 1H), 3.59-3.68 (m, 2H), 2.95 (dd, J=12.2, 6.4 Hz, 1H), 2.82 (dd, J=12.2, 4.9 Hz, 1H), 2.33-2.47 (m, 2H), 2.08-2.31 (m, 1H), 1.83-1.95 (m, 1H), 1.49 (d, J=7.1 Hz, 3H), 1.26-1.48 (m, 3H), 1.13-1.25 (m, 1H), 0.97 (d, J=6.8 Hz, 3H), 0.90 (t, J=7.1 Hz, 3H), 0.75-0.84 (m, 1H), 0.37-0.46 (m, 2H), −0.02-0.08 (m, 2H); LRMS (ESI) m/e 423.4 [(M+H)$^+$, calcd for $C_{27}H_{39}N_2O_2$ 423.3].

EXAMPLE 8

(2S)-N-((1R)-2-(2-Methylbutylamino)-1-(4-(2-methylpentyloxy)phenyl)ethyl)-2-phenylpropanamide

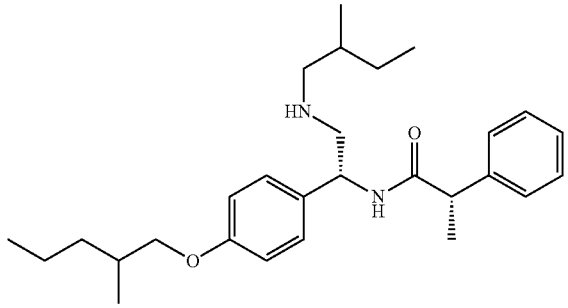

Prepared by the method described in example 7 using the appropriate starting materials to give (2S)-N-((1R)-2-(2-methylbutylamino)-1-(4-(2-methylpentyloxy)phenyl)ethyl)-2-phenylpropanamide: $t_R$=3.09 min (Method A), LRMS (ESI) m/e 439.1 [(M+H)$^+$, calcd for $C_{28}H_{43}N_2O_2$ 439.3].

EXAMPLE 9

(2S)-N-((1R)-1-(4-(2-Methylpentyloxy)phenyl)-2-(pyridin-4-ylmethylamino)ethyl)-2-phenylpropanamide

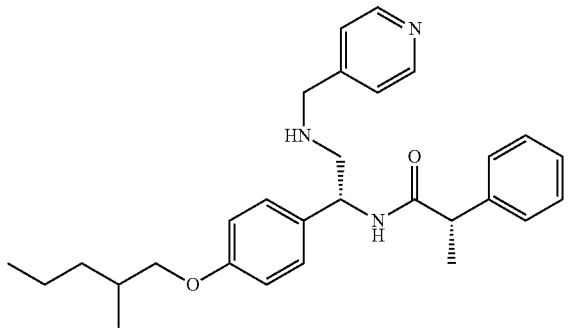

Prepared by the method described in example 7 using the appropriate starting materials to give (2S)-N-((1R)-1-(4-(2-methylpentyloxy)phenyl)-2-(pyridin-4-ylmethylamino)ethyl)-2-phenylpropanamide: $t_R$=2.87 min (Method A), LRMS (ESI) m/e 460.4 [(M+H)$^+$, calcd for $C_{29}H_{38}N_3O_2$ 460.3].

EXAMPLE 10

(2S)-N-((1R)-1-(4-(2-Methylpentyloxy)phenyl)-2-(pyridin-2-ylmethylamino)ethyl)-2-phenylpropanamide

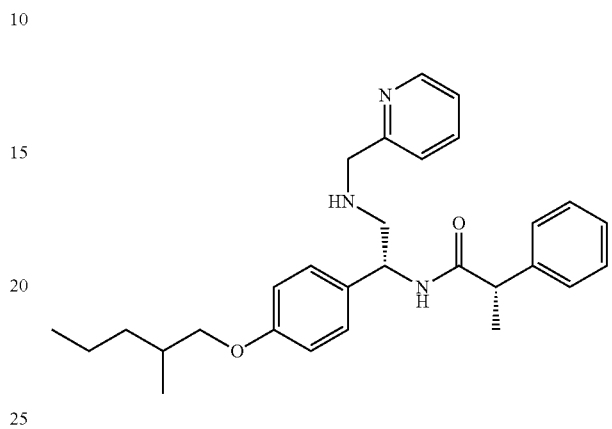

Prepared by the method described in example 7 using the appropriate starting materials to give (2S)-N-((1R)-1-(4-(2-methylpentyloxy)phenyl)-2-(pyridin-2-ylmethylamino)ethyl)-2-phenylpropanamide: $t_R$=2.90 min (Method A), LRMS (ESI) m/e 460.1 [(M+H)$^+$, calcd for $C_{29}H_{38}N_3O_2$ 460.3].

EXAMPLE 11

(2S)-N-((1R)-2-((1H-Pyrazol-3-yl)methylamino)-1-(4-(2-methylpentyloxy)phenyl)ethyl)-2-phenylpropanamide

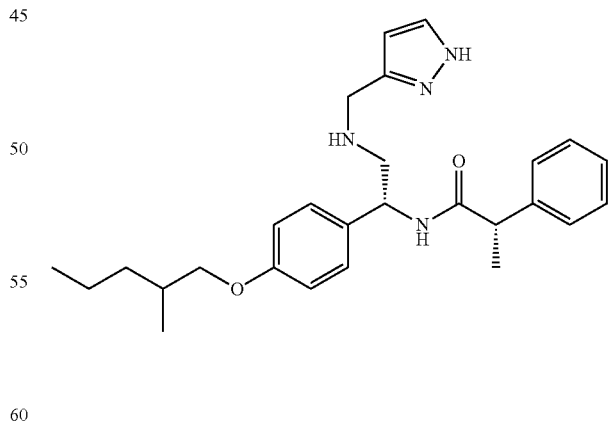

Prepared by the method described in example 7 using the appropriate starting materials to give (2S)-N-((1R)-2-((1H-pyrazol-3-yl)methylamino)-1-(4-(2-methylpentyloxy)phenyl)-ethyl)-2-phenylpropanamide: $t_R$=2.65 min (Method A), LRMS (ESI) m/e 449.4 [(M+H)$^+$, calcd for $C_{27}H_{37}N_4O_2$ 449.3].

EXAMPLE 12

(2S)-N-((1R)-2-((1H-Indol-3-yl)methylamino)-1-(4-(2-methylpentyloxy)phenyl)ethyl)-2-phenylpropanamide

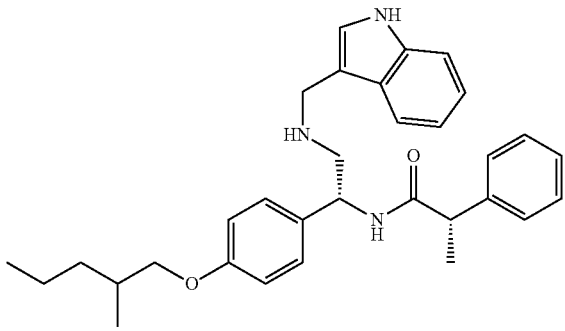

Prepared by the method described in example 7 using the appropriate starting materials to give (2S)-N-((1R)-2-((1H-indol-3-yl)methylamino)-1-(4-(2-methylpentyloxy)phenyl)-ethyl)-2-phenylpropanamide: $t_R$=2.95 min (Method A), LRMS (ESI) m/e 498.5 [(M+H)$^+$, calcd for $C_{32}H_{40}N_3O_2$ 498.3].

EXAMPLE 13

(2S)-N-((1R)-1-(4-(2-Methylpentyloxy)phenyl)-2-(pyridin-3-ylmethylamino)ethyl)-2-phenylpropanamide

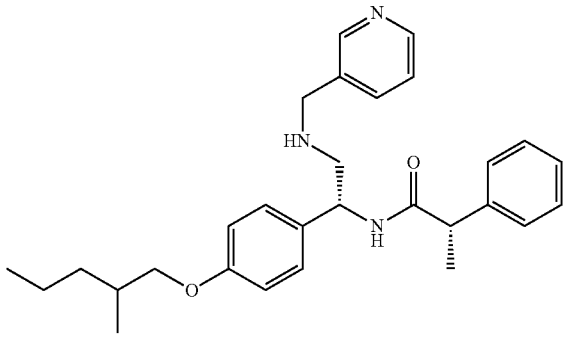

Prepared by the method described in example 7 using the appropriate starting materials to give (2S)-N-((1R)-1-(4-(2-methylpentyloxy)phenyl)-2-(pyridin-3-ylmethylamino)ethyl)-2-phenylpropanamide: $t_R$=2.93 min (Method A), LRMS (ESI) m/e 460.4 [(M+H)$^+$, calcd for $C_{29}H_{38}N_3O_2$ 460.3].

EXAMPLE 14

(2S)-N-((1R)-1-(4-(2-Methylpentyloxy)phenyl)-2-((tetrahydrofuran-3-yl)methylamino)ethyl)-2-phenyl-propanamide

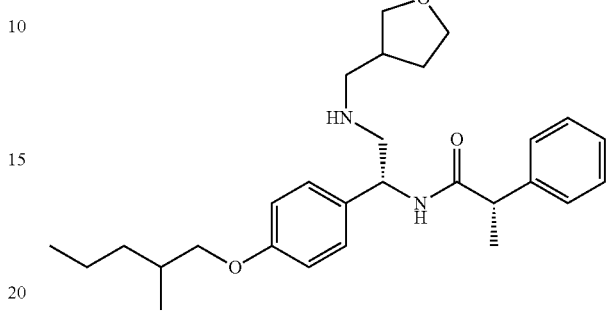

Prepared by the method described in example 7 using the appropriate starting materials to give (2S)-N-((1R)-1-(4-(2-methylpentyloxy)phenyl)-2-((tetrahydrofuran-3-yl)methylamino)ethyl)-2-phenylpropanamide: $t_R$=2.75 min (Method A), LRMS (ESI) m/e 453.4 [(M+H)$^+$, calcd for $C_{28}H_{41}N_2O_3$ 453.3].

EXAMPLE 15

(2S)-N-((1R)-2-((1-Aminocyclopentyl)methylamino)-1-(4-(2-methylpentyloxy)phenyl)ethyl)-2-phenylpropanamide

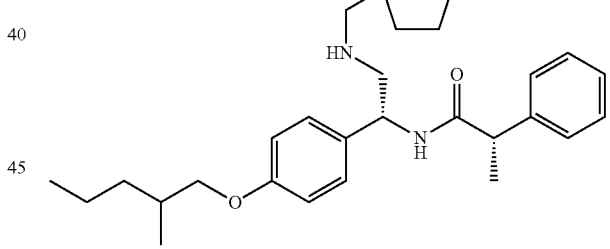

Part A. t-butyl 1-(((2R)-2-(4-(2-methylpentyloxy)phenyl)-2-((S)-2-phenylpropanamido)ethylamino)methyl)-cyclopentylcarbamate To a stirred solution of (2S)-N-((1R)-2-amino-1-(4-(2-methylpentyloxy)phenyl)ethyl)-2-phenylpropanamide (200 mg, 0.543 mmol) in acetonitrile (5 mL) at 0° C., was added N-t-Boc-cycloleucinal (116 mg, 0.543 mmol). Stirring was continued for 15 min. To this mixture, sodium triacetoxyborohydride (230 mg, 1.085 mmol) was added and the reaction mixture was stirred at room temperature for 1 h. The reaction mixture was transferred to a separatory funnel containing saturated aqueous NaHCO$_3$ solution (10 mL). The aqueous layer was extracted with ethyl acetate (2×20 mL). The combined organic layers were washed with brine, dried over MgSO$_4$, filtered and concentrated to give t-butyl 1-(((2R)-2-(4-(2-methylpentyloxy)phenyl)-2-((S)-2-phenylpropanamido)ethylamino)methyl)cyclopentylcarbamate (305 mg). The crude product was used directly in the next step: LRMS (ESI) m/e 566.5 [(M+H)+, calcd for $C_{34}H_{52}N_3O_4$ 566.4].

Part B. (2S)-N-((1R)-2-((1-aminocyclopentyl)methylamino)-1-(4-(2-methylpentyloxy)phenyl)ethyl)-2-phenylpropanamide To a solution of crude t-butyl 1-(((2R)-2-(4-(2-methylpentyloxy)phenyl)-2-((S)-2-phenylpropanamido)ethylamino)methyl)cyclopentylcarbamate from Part A (195 mg, 0.345 mmol) in dichloromethane (2 mL) at 0° C. was added TFA (1 mL, 12.98 mmol). The reaction mixture was stirred for 1.5 h while being allowed to warm to room temperature. The mixture was concentrated and the product was purified by reverse phase HPLC (acetonitrile/water with 0.1% TFA). The organic solvent was removed on the rotovapor and the aqueous mixture was frozen and placed on the lyophilizer to afford (2S)-N-((1R)-2-((1-aminocyclopentyl)methylamino)-1-(4-(2-methylpentyloxy)phenyl)ethyl)-2-phenylpropanamide (154 mg, 63% yield, 2 steps) as a colorless amorphous solid: $^1$H NMR (300 MHz, 100° C., DMSO-$d_6$) δ 7.95 (d, J=8.1 Hz, 1H), 7.16-7.34 (m, 5H), 7.11 (d, J=8.4 Hz, 2H), 6.81 (d, J=8.8 Hz, 2H), 6.87 (br. s., 5H), 4.94-5.06 (m, 1H), 3.68-3.88 (m, 3H), 2.96-3.13 (m, 2H), 2.93 (s, 2H), 1.59-1.95 (m, 9H), 1.40 (d, J=7.0 Hz, 3H), 1.17-1.49 (m, 4H), 0.97 (d, J=7.0 Hz, 3H), 0.90 (t, J=7.0 Hz, 3H); HPLC $t_R$=2.68 min (Method A); LRMS (ESI) m/e 466.5 [(M+H)+, calcd for $C_{29}H_{44}N_3O_2$ 466.4].

EXAMPLE 16

(2S)-N-((1R)-1-(4-(2-Methylpentyloxy)phenyl)-2-((S)-pyrrolidin-2-ylmethylamino)ethyl)-2-phenylpropanamide

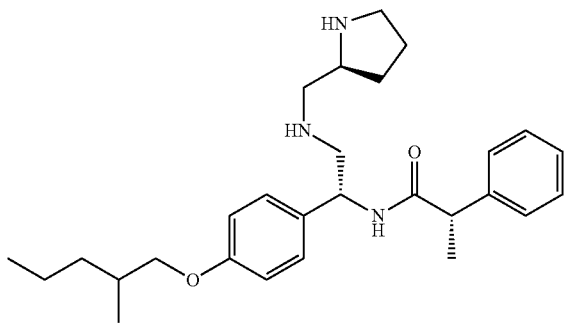

Prepared by the method described in example 15 using the appropriate starting materials to give (2S)-N-((1R)-1-(4-(2-methylpentyloxy)phenyl)-2-((S)-pyrrolidin-2-ylmethylamino)ethyl)-2-phenylpropanamide: $t_R$=2.67 min (Method A), LRMS (ESI) m/e 452.5 [(M+H)+, calcd for $C_{28}H_{42}N_3O_2$ 452.3].

EXAMPLE 17

(2S)-N-((1R)-2-((S)-2-Aminopropylamino)-1-(4-(2-methylpentyloxy)phenyl)ethyl)-2-phenylpropanamide

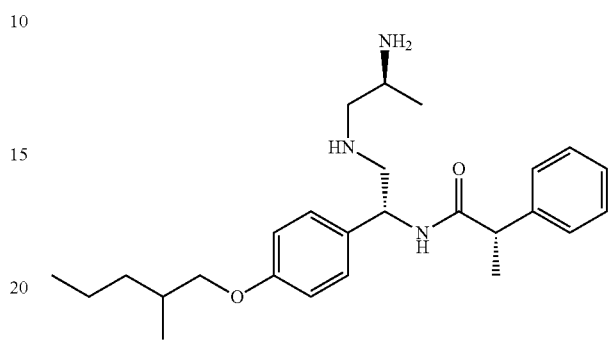

Prepared by the method described in example 15 using the appropriate starting materials to give (2S)-N-((1R)-2-((S)-2-aminopropylamino)-1-(4-(2-methylpentyloxy)phenyl)-ethyl)-2-phenylpropanamide: $t_R$=2.55 min (Method A), LRMS (ESI) m/e 426.4 [(M+H)+, calcd for $C_{26}H_{40}N_3O_2$ 426.3].

EXAMPLE 18

(2S)-N-((1R)-1-(4-(2-Methylpentyloxy)phenyl)-2-((R)-pyrrolidin-2-ylmethylamino)ethyl)-2-phenylpropanamide

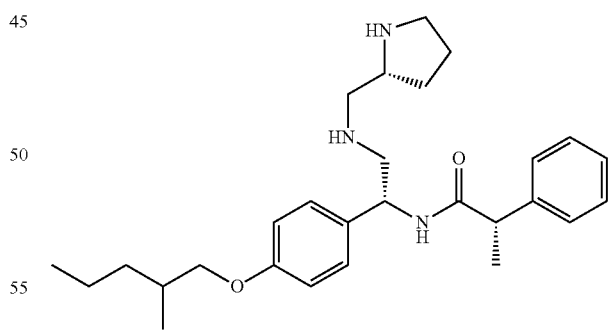

Prepared by the method described in example 15 using the appropriate starting materials to give (2S)-N-((1R)-1-(4-(2-methylpentyloxy)phenyl)-2-((R)-pyrrolidin-2-ylmethylamino)ethyl)-2-phenylpropanamide: $t_R$=2.68 min (Method A), LRMS (ESI) m/e 452.5 [(M+H)+, calcd for $C_{28}H_{42}N_3O_2$ 452.3].

EXAMPLE 19

(2S,3S)-2-Amino-3-methyl-N-((2R)-2-(4-(2-methyl-pentyloxy)phenyl)-2-((S)-2-phenylpropanamido)ethyl)pentanamide

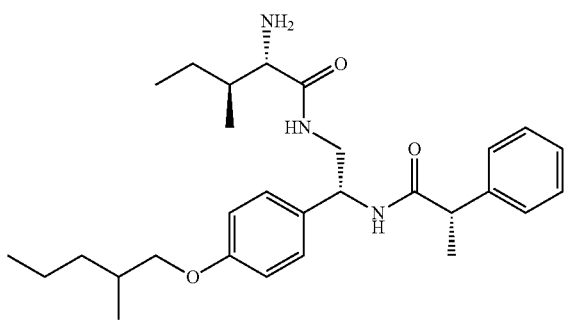

Part A. t-Butyl (2S,3S)-3-methyl-1-((2R)-2-(4-(2-methylpentyloxy)phenyl)-2-((S)-2-phenylpropanamido)ethylamino)-1-oxopentan-2-ylcarbamate A stirred solution of (2S)-N-((1R)-2-amino-1-(4-(2-methylpentyloxy)phenyl)ethyl)-2-phenylpropanamide (200 mg, 0.543 mmol), prepared according to the procedure described in example 5, in dichloromethane (4 mL) was cooled to 0° C. To this solution, Boc-L-isoleucine (188 mg, 0.814 mmol), N,N-diisopropylethylamine (0.569 mL, 3.26 mmol) and HATU (310 mg, 0.814 mmol) were added. The ice-water bath was removed and reaction mixture was stirred at room temperature for 3 h. The mixture was transferred to a separatory funnel containing saturated aqueous NaHCO$_3$ solution (60 mL). The aqueous layer was extracted with ethyl acetate (3×50 mL). The combined organic layers were washed with brine, dried over MgSO$_4$, filtered and concentrated. The residue was purified by column chromatography on silica gel (30→40% ethyl acetate in hexanes) to afford t-butyl (2S,3S)-3-methyl-1-((2R)-2-(4-(2-methylpentyloxy)phenyl)-2-((S)-2-phenylpropanamido)ethylamino)-1-oxopentan-2-ylcarbamate (190 mg, 60% yield) as a colorless solid: LRMS (ESI) m/e 582.4 [(M+H)$^+$, calcd for C$_{34}$H$_{52}$N$_3$O$_5$ 582.4].

Part B. (2S,3S)-2-amino-3-methyl-N-((2R)-2-(4-(2-methylpentyloxy)phenyl)-2-((S)-2-phenylpropanamido)ethyl)pentanamide To a solution of t-butyl (2S,3S)-3-methyl-1-((2R)-2-(4-(2-methylpentyloxy)phenyl)-2-((S)-2-phenylpropanamido)ethylamino)-1-oxopentan-2-ylcarbamate (80 mg, 0.138 mmol) in dichloromethane (2 mL) was added TFA (1 mL, 12.98 mmol). The reaction mixture was stirred at room temperature for 1 h. The mixture was concentrated and the residue was transferred to a separatory funnel containing saturated aqueous K$_2$CO$_3$ solution. The aqueous layer was extracted with ethyl acetate (2×10 mL). The combined organic layers were dried over MgSO$_4$, filtered and concentrated. $^1$H NMR indicated that the product was still a TFA salt. The product was dissolved in methanol and passed through a cation exchange resin (washed with methanol and water to remove the acid followed by 2M ammonia in methanol to elute the product) to afford (2S,3S)-2-amino-3-methyl-N-((2R)-2-(4-(2-methylpentyloxy)phenyl)-2-((S)-2-phenylpropanamido)ethyl)pentanamide (51 mg, 77% yield) as a colorless solid as the free base: $^1$H NMR (400 MHz, CDCl$_3$) δ 7.70 (t, J=6.2 Hz, 1H), 7.26-7.33 (m, 2H), 7.19-7.26 (m, 3H), 6.93 (d, J=6.5 Hz, 1H), 6.87 (d, 2H), 6.70 (d, J=8.6 Hz, 2H), 4.89 (ddd, J=9.5, 6.4, 3.5 Hz, 1H), 3.72 (dd, J=8.8, 5.8 Hz, 1H), 3.62 (dd, J=8.8, 6.8 Hz, 1H), 3.45-3.57 (m, 2H), 3.35 (ddd, J=14.0, 5.7, 3.9 Hz, 1H), 3.23 (d, J=3.5 Hz, 1H), 1.93-2.04 (m, 1H), 1.83-1.93 (m, 1H), 1.42 (d, J=7.1 Hz, 3H), 1.23-1.54 (m, 6H), 1.01-1.21 (m, 2H), 0.96 (d, J=6.8 Hz, 3H), 0.94 (d, J=7.3 Hz, 3H), 0.90 (t, J=7.3 Hz, 3H), 0.89 (t, J=7.1 Hz, 3H); LRMS (ESI) m/e 482.5 [(M+H)$^+$, calcd for C$_{29}$H$_{44}$N$_3$O$_3$ 482.3].

EXAMPLE 20

(2R)-2-Amino-4-methyl-N-((2R)-2-(4-(2-methylpentyloxy)phenyl)-2-((S)-2-phenylpropanamido)ethyl)pentanamide

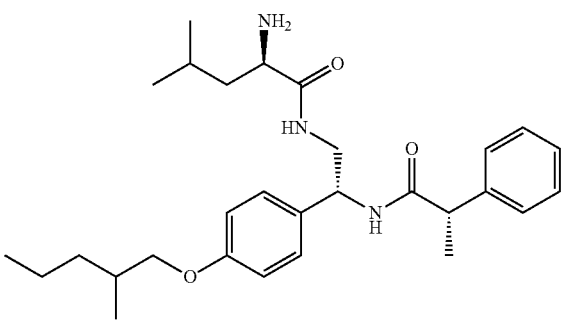

Prepared by the method described in example 19 using the appropriate starting materials to give (2R)-2-amino-4-methyl-N-((2R)-2-(4-(2-methylpentyloxy)phenyl)-2-((S)-2-phenylpropanamido)ethyl)pentanamide: t$_R$=10.08 min (Method B), LRMS (ESI) m/e 482.6 [(M+H)$^+$, calcd for C$_{29}$H$_{44}$N$_3$O$_3$ 482.3].

EXAMPLE 21

(2S)-N-((2R)-2-(4-(2-Methylpentyloxy)phenyl)-2-((S)-2-phenylpropanamido)ethyl)pyrrolidine-2-carboxamide

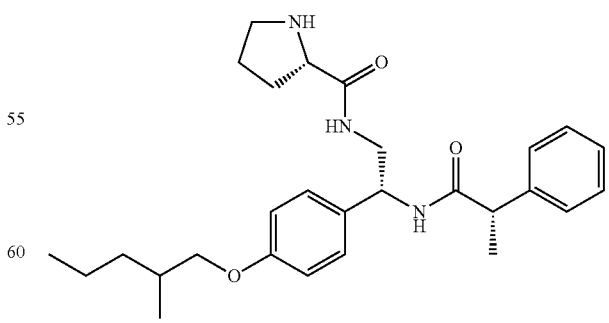

Prepared by the method described in example 19 using the appropriate starting materials to give (2S)-N-((2R)-2-(4-(2-methylpentyloxy)phenyl)-2-((S)-2-phenylpropanamido)- ethyl)pyrrolidine-2-carboxamide: $t_R$=8.19 min (Method B), LRMS (ESI) m/e 466.5 [(M+H)$^+$, calcd for $C_{28}H_{40}N_3O_3$ 466.3].

EXAMPLE 22

(2R,3R)-2-Amino-3-methyl-N-((2R)-2-(4-(2-methylpentyloxy)phenyl)-2-((S)-2-phenylpropanamido)ethyl)pentanamide

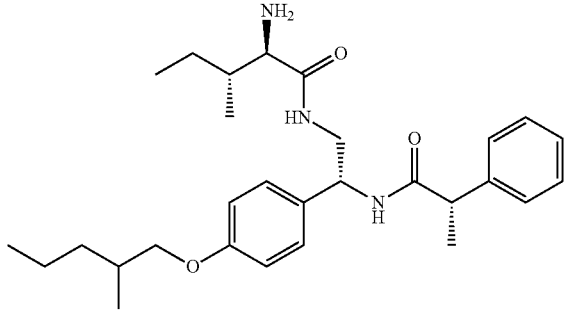

Prepared by the method described in example 19 using the appropriate starting materials to give (2R,3R)-2-amino-3-methyl-N-((2R)-2-(4-(2-methylpentyloxy)phenyl)-2-((S)-2-phenylpropanamido)ethyl)pentanamide: $t_R$=10.00 min (Method B), LRMS (ESI) m/e 482.6 [(M+H)$^+$, calcd for $C_{29}H_{44}N_3O_3$ 482.3].

EXAMPLE 23

(2S)-2-Amino-N-((2R)-2-(4-(2-methylpentyloxy)phenyl)-2-((S)-2-phenylpropanamido)ethyl)propanamide

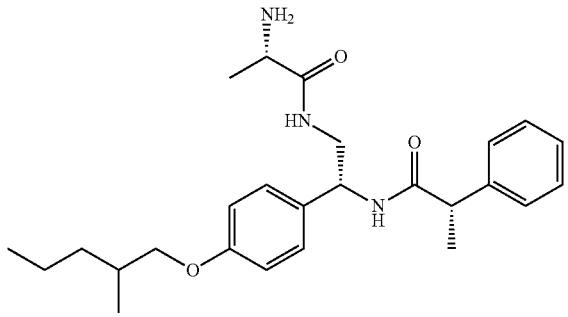

Prepared by the method described in example 19 using the appropriate starting materials to give (2S)-2-amino-N-((2R)-2-(4-(2-methylpentyloxy)phenyl)-2-((S)-2-phenylpropanamido)ethyl)propanamide: $t_R$=7.94 min (Method B), LRMS (ESI) m/e 440.5 [(M+H)$^+$, calcd for $C_{26}H_{38}N_3O_3$ 440.3].

EXAMPLE 24

(2S)-2-Amino-3-methyl-N-((2R)-2-(4-(2-methylpentyloxy)phenyl)-2-((S)-2-phenylpropanamido)ethyl)butanamide

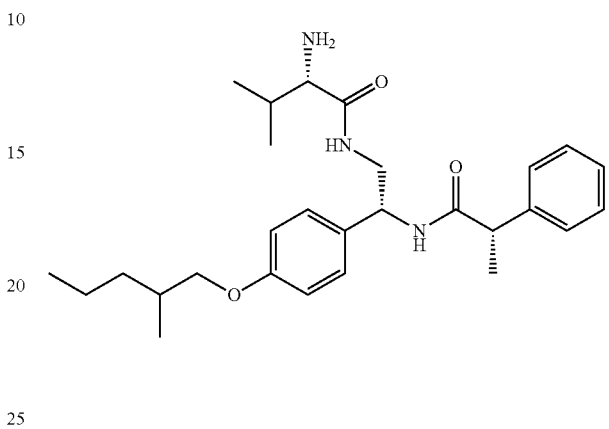

Prepared by the method described in example 19 using the appropriate starting materials to give (2S)-2-amino-3-methyl-N-((2R)-2-(4-(2-methylpentyloxy)phenyl)-2-((S)-2-phenylpropanamido)ethyl)butanamide: $t_R$=5.48 min (Method C), LRMS (ESI) m/e 468.3 [(M+H)$^+$, calcd for $C_{28}H_{42}N_3O_3$ 468.3].

EXAMPLE 25

(2S)-2-Amino-N-((2R)-2-(4-(2-methylpentyloxy)phenyl)-2-((S)-2-phenylpropanamido)ethyl)butanamide

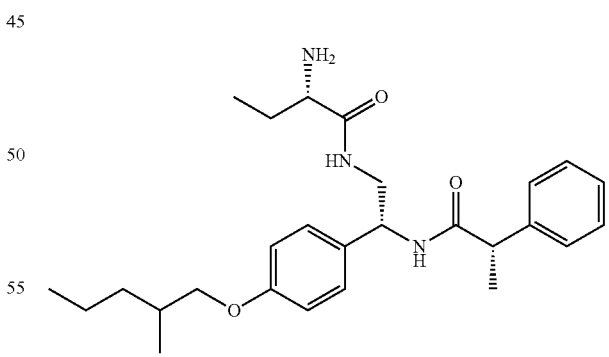

Prepared by the method described in example 19 using the appropriate starting materials to give (2S)-2-amino-N-((2R)-2-(4-(2-methylpentyloxy)phenyl)-2-((S)-2-phenylpropanamido)ethyl)butanamide: $t_R$=8.40 min (Method B), LRMS (ESI) m/e 454.6 [(M+H)$^+$, calcd for $C_{27}H_{40}N_3O_3$ 454.3].

EXAMPLE 26

(2S)-2-Amino-N-((2R)-2-(4-(2-methylpentyloxy)phenyl)-2-((S)-2-phenylpropanamido)ethyl)pentanamide

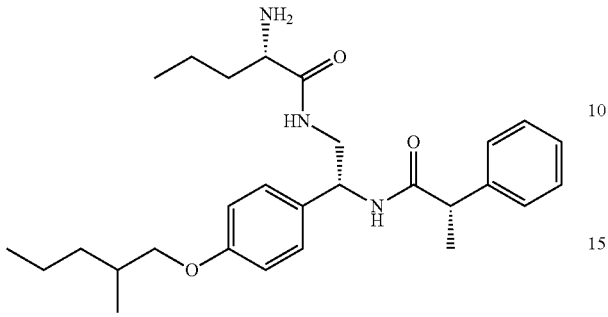

Prepared by the method described in example 19 using the appropriate starting materials to give (2S)-2-amino-N-((2R)-2-(4-(2-methylpentyloxy)phenyl)-2-((S)-2-phenylpropanamido)ethyl)pentanamide: $t_R$=5.58 min (Method C), LRMS (ESI) m/e 468.3 [(M+H)$^+$, calcd for $C_{28}H_{42}N_3O_3$ 468.3].

EXAMPLE 27

(2S,3R)-2-Amino-3-methyl-N-((2R)-2-(4-(2-methylpentyloxy)phenyl)-2-((S)-2-phenylpropanamido)ethyl)pentanamide

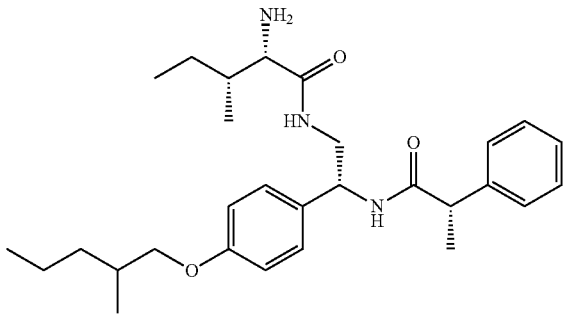

Prepared by the method described in example 19 using the appropriate starting materials to give (2S,3R)-2-amino-3-methyl-N-((2R)-2-(4-(2-methylpentyloxy)phenyl)-2-((S)-2-phenylpropanamido)ethyl)pentanamide: $t_R$=10.19 min (Method B), LRMS (ESI) m/e 482.6 [(M+H)$^+$, calcd for $C_{29}H_{44}N_3O_3$ 482.3].

EXAMPLE 28

(2S)-2-Amino-3-cyclopropyl-N-((2R)-2-(4-(2-methylpentyloxy)phenyl)-2-((S)-2-phenylpropanamido)ethyl)propanamide

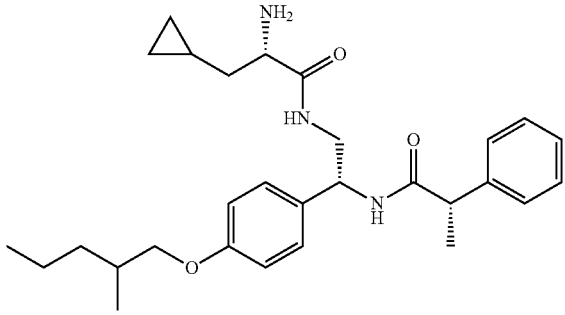

Prepared by the method described in example 19 using the appropriate starting materials to give (2S)-2-amino-3-cyclopropyl-N-((2R)-2-(4-(2-methylpentyloxy)phenyl)-2-((S)-2-phenylpropanamido)ethyl)propanamide: $t_R$=5.63 min (Method C), LRMS (ESI) m/e 480.3 [(M+H)$^+$, calcd for $C_{29}H_{42}N_3O_3$ 480.3].

EXAMPLE 29

(2R)-2-Amino-N-((2R)-2-(4-(2-methylpentyloxy)phenyl)-2-((S)-2-phenylpropanamido)ethyl)propanamide

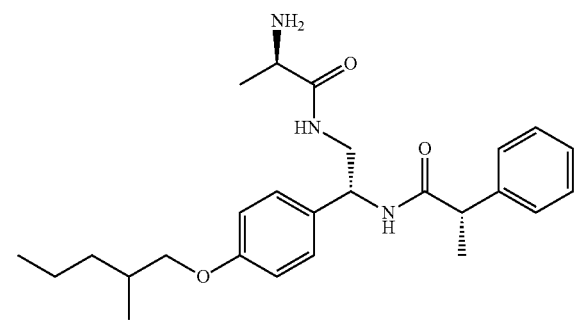

Prepared by the method described in example 19 using the appropriate starting materials to give (2R)-2-amino-N-((2R)-2-(4-(2-methylpentyloxy)phenyl)-2-((S)-2-phenylpropanamido)ethyl)propanamide: $t_R$=7.95 min (Method B), LRMS (ESI) m/e 440.5 [(M+H)$^+$, calcd for $C_{26}H_{38}N_3O_3$ 440.3].

EXAMPLE 30

(2S)-N-((1R)-2-((R)-2-Amino-2-cyclopropylacetamido)-1-(4-(2-methylpentyloxy)phenyl)ethyl)-2-phenylpropanamide

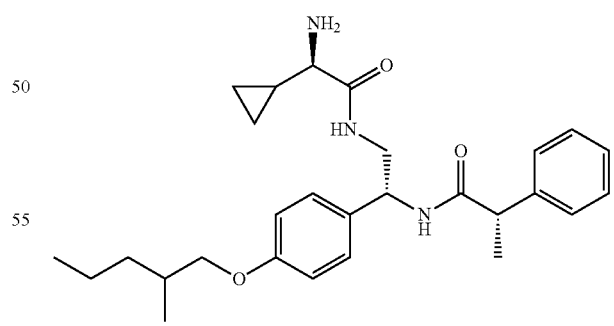

Prepared by the method described in example 19 using the appropriate starting materials to give (2S)-N-((1R)-2-((R)-2-amino-2-cyclopropylacetamido)-1-(4-(2-methylpentyloxy)phenyl)ethyl)-2-phenylpropanamide: $t_R$=8.56 min (Method B), LRMS (ESI) m/e 466.5 [(M+H)$^+$, calcd for $C_{28}H_{40}N_3O_3$ 466.3].

EXAMPLE 31

(2R)-2-Amino-N-((2R)-2-(4-(2-methylpentyloxy)phenyl)-2-((S)-2-phenylpropanamido)ethyl)pentanamide

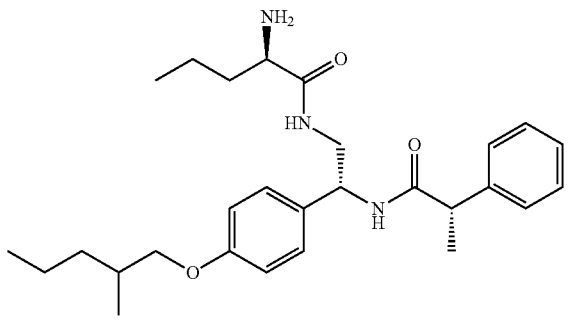

Prepared by the method described in example 19 using the appropriate starting materials to give (2R)-2-amino-N-((2R)-2-(4-(2-methylpentyloxy)phenyl)-2-((S)-2-phenylpropanamido)ethyl)pentanamide: $t_R$=5.72 min (Method C), LRMS (ESI) m/e 468.3 [(M+H)$^+$, calcd for $C_{28}H_{42}N_3O_3$ 468.3].

EXAMPLE 32

(2S,3R)-2-Amino-3-methoxy-N-((2R)-2-(4-(2-methylpentyloxy)phenyl)-2-((S)-2-phenylpropanamido)ethyl)butanamide

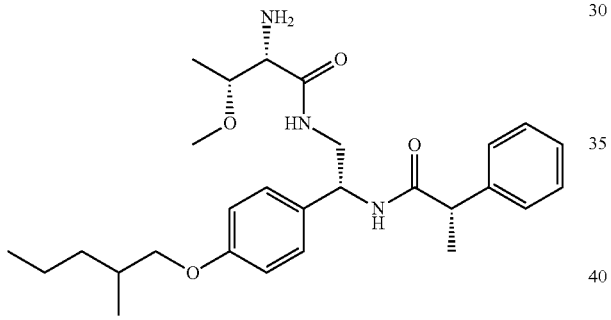

Prepared by the method described in example 19 using the appropriate starting materials to give (2S,3R)-2-amino-3-methoxy-N-((2R)-2-(4-(2-methylpentyloxy)phenyl)-2-((S)-2-phenylpropanamido)ethyl)butanamide: $t_R$=9.85 min (Method B), LRMS (ESI) m/e 484.5 [(M+H)$^+$, calcd for $C_{28}H_{42}N_3O_4$ 484.3].

EXAMPLE 33

(2R,3S)-2-Amino-3-methyl-N-((2R)-2-(4-(2-methylpentyloxy)phenyl)-2-((S)-2-phenylpropanamido)ethyl)pentanamide

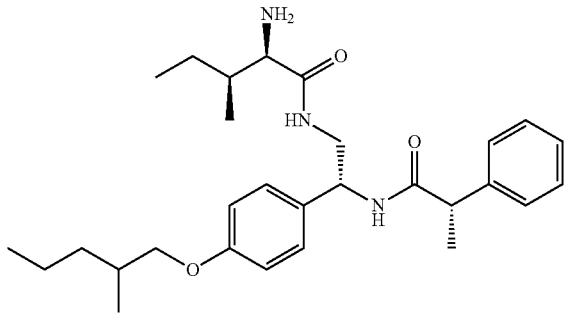

Prepared by the method described in example 19 using the appropriate starting materials to give (2R,3S)-2-amino-3-methyl-N-((2R)-2-(4-(2-methylpentyloxy)phenyl)-2-((S)-2-phenylpropanamido)ethyl)pentanamide: $t_R$=10.43 min (Method B), LRMS (ESI) m/e 482.6 [(M+H)$^+$, calcd for $C_{29}H_{44}N_3O_3$ 482.3].

EXAMPLE 34

(2R)-2-Amino-N-((2R)-2-(4-(2-methylpentyloxy)phenyl)-2-((S)-2-phenylpropanamido)ethyl)-3-(thiazol-4-yl)propanamide

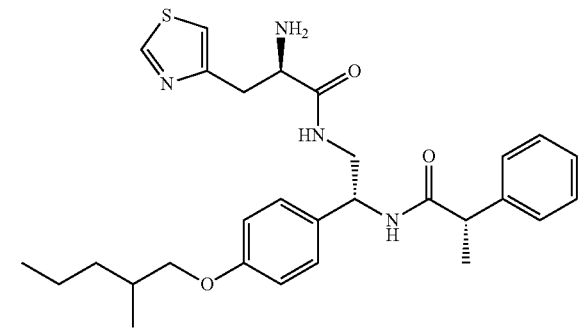

Prepared by the method described in example 19 using the appropriate starting materials to give (2R)-2-amino-N-((2R)-2-(4-(2-methylpentyloxy)phenyl)-2-((S)-2-phenylpropanamido)ethyl)-3-(thiazol-4-yl)propanamide: $t_R$=9.60 min (Method B), LRMS (ESI) m/e 523.5 [(M+H)$^+$, calcd for $C_{29}H_{39}N_4O_3S$ 523.3].

EXAMPLE 35

(2S)-N-((1R)-1-(4-(2-Methylpentyloxy)phenyl)-2-morpholinoethyl)-2-phenylpropanamide

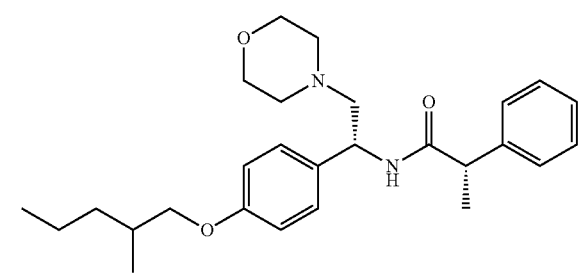

To a mixture of (2S)-N-((1R)-2-amino-1-(4-(2-methylpentyloxy)phenyl)ethyl)-2-phenylpropanamide (100 mg, 0.271 mmol), prepared according to the procedure described in example 5, and potassium carbonate (75 mg, 0.543 mmol) in acetonitrile (4 mL) was added 2-bromoethyl ether (0.038 mL, 0.271 mmol). The reaction mixture was then heated at reflux for 18 h. The mixture was cooled to room temperature, filtered and the filtrate was concentrated. The residue was then transferred to a separatory funnel containing water (20 mL) and the aqueous layer was extracted with ethyl acetate (2×20 mL). The combined organic layers were washed with brine (10 mL), dried over MgSO$_4$, filtered and concentrated. The residue was purified by HPLC (acetonitrile/water with 0.1% TFA) to afford (2S)-N-((1R)-1-(4-(2-methylpentyloxy)phenyl)-2-morpholinoethyl)-2-phenylpropanamide.TFA (55 mg, 37% yield) as a yellow oil: $^1$H NMR (400 MHz, CDCl$_3$)

δ 7.25-7.39 (m, 5H), 6.97 (d, J=8.6 Hz, 2H), 6.76 (d, J=8.8 Hz, 2H), 6.36 (br. s., 1H), 4.83 (d, J=5.0 Hz, 1H), 3.74 (dd, J=8.8, 5.8 Hz, 1H), 3.61-3.69 (m, 2H), 3.49-3.61 (m, 4H), 2.34-2.56 (m, 4H), 2.23-2.30 (m, 2H), 1.83-1.95 (m, 1H), 1.52 (d, J=7.3 Hz, 3H), 1.26-1.50 (m, 3H), 1.12-1.22 (m, 1H), 0.97 (d, J=6.8 Hz, 3H), 0.90 (t, J=7.3 Hz, 3H); LRMS (ESI) m/e 439.3 [(M+H)$^+$, calcd for C$_{27}$H$_{39}$N$_2$O$_3$ 439.3].

EXAMPLE 36

(2S)-N-(1-(4-(2-Methylpentyloxy)phenyl)-2-(4-methylpiperazin-1-yl)ethyl)-2-phenylpropanamide

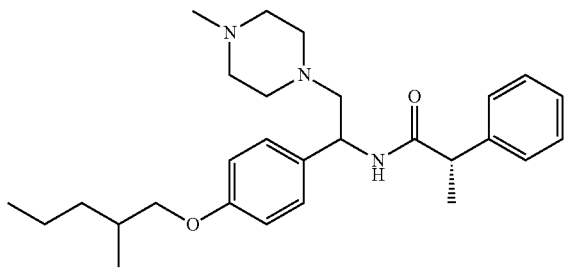

Part A. t-Butyl (1R)-1-(4-(2-methylpentyloxy)phenyl)-2-oxoethylcarbamate

A solution of t-butyl (1R)-2-hydroxy-1-(4-(2-methylpentyloxy)phenyl)ethylcarbamate (500 mg, 1.48 mmol) prepared according to the procedure described in example 1, in dichloromethane (10 mL) was treated with sodium bicarbonate (622 mg, 7.41 mmol) and Dess-Martin Periodinane (1.26 g, 2.96 mmol) at room temperature. The mixture was stirred at room temperature under N$_2$ for 1.5 h. The reaction mixture was placed in an ice-water bath and a 1:1 mixture of saturated aqueous NaHCO$_3$ solution and saturated NaHSO$_3$ solution (4 mL) was added and the cooling bath was removed and the mixture was stirred for 5 min at room temperature. The reaction mixture was transferred to a separatory funnel containing saturated aqueous NaHCO$_3$ solution (20 mL). The aqueous layer was extracted with ethyl acetate (3×25 mL). The combined organic layers were washed with brine (20 mL), dried over MgSO$_4$, filtered and concentrated. The residue was purified by column chromatography on silica gel (10%→15% ethyl acetate in hexanes, 25 g column) to afford t-butyl (1R)-1-(4-(2-methylpentyloxy)phenyl)-2-oxoethylcarbamate (318 mg, 64% yield) as a colorless oil which was stored in the freezer until used in the next step: $^1$H NMR (400 MHz, DMSO-d$_6$) δ 9.48 (s, 1H), 7.76 (d, J=7.6 Hz, 1H), 7.23 (d, J=8.6 Hz, 2H), 6.93 (d, J=8.6 Hz, 2H), 5.11 (d, J=7.6 Hz, 1H), 3.82 (dd, J=9.6, 6.0 Hz, 1H), 3.73 (dd, J=9.3, 6.5 Hz, 1H), 1.82-1.92 (m, 1H), 1.40 (s, 9H), 1.25-1.49 (m, 3H), 1.11-1.22 (m, 1H), 0.96 (d, J=6.8 Hz, 3H), 0.88 (t, J=7.1 Hz, 3H); LRMS (ESI) m/e 279.2 [(M-t-Bu)$^+$, calcd for C$_{15}$H$_{21}$NO$_4$ 279.1].

Part B. t-Butyl (1R)-1-(4-(2-methylpentyloxy)phenyl)-2-(4-methylpiperazin-1-yl)ethylcarbamate To a solution of t-butyl (1R)-1-(4-(2-methylpentyloxy)phenyl)-2-oxoethylcarbamate (80 mg, 0.238 mmol) in dichloroethane (1 mL) was added 1-methylpiperazine (0.032 mL, 0.286 mmol) followed by sodium triacetoxyborohydride (70.8 mg, 0.334 mmol). The mixture was stirred at room temperature for 3 h. Additional 1-methylpiperazine (0.064 mL, 0.572 mmol) and sodium triacetoxyborohydride (71 mg, 0.334 mmol) were added and the mixture was stirred at room temperature for 1 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (5 mL), dried over MgSO$_4$, filtered and concentrated. The product, t-butyl 1-(4-(2-methylpentyloxy)phenyl)-2-(4-methylpiperazin-1-yl)ethylcarbamate, was used directly in the next step: LRMS (ESI) m/e 420.3 [(M+H)$^+$, calcd for C$_{24}$H$_{42}$N$_3$O$_3$ 420.3].

Part C. (1R)-1-(4-(2-Methylpentyloxy)phenyl)-2-(4-methylpiperazin-1-yl)ethanamine To a solution of t-butyl (1R)-1-(4-(2-methylpentyloxy)phenyl)-2-(4-methylpiperazin-1-yl)ethylcarbamate (87 mg, 0.207 mmol) in dichloromethane (1 mL) at 0° C. was added trifluoroacetic acid (0.25 mL, 3.24 mmol). The cooling bath was removed and the mixture was stirred at room temperature for 2 h. The reaction mixture was concentrated and the product was purified by reverse phase HPLC (acetonitrile/water with 0.1% TFA). The organic solvent was removed on the rotovapor and the aqueous mixture was frozen and placed on the lyophilizer to afford 1-(4-(2-methylpentyloxy)phenyl)-2-(4-methylpiperazin-1-yl)ethanamine.3TFA (85.9 mg, 63% yield, 2 steps) as a colorless amorphous semi-solid: $^1$H NMR (400 MHz, DMSO-d$_6$) δ 9.84 (br. s., 1H), 8.21 (br. s., 3H), 7.38 (d, J=8.6 Hz, 2H), 6.99 (d, J=8.6 Hz, 2H), 4.41 (dt, J=9.5, 4.7 Hz, 1H), 3.83 (dd, J=9.3, 5.8 Hz, 1H), 3.75 (dd, J=9.3, 6.5 Hz, 1H), 3.41 (d, J=11.8 Hz, 2H), 3.13 (d, J=12.6 Hz, 1H), 2.94-3.07 (m, 3H), 2.92 (d, J=13.3 Hz, 1H), 2.72-2.84 (m, 4H), 2.58 (dd, J=13.5, 4.7 Hz, 1H), 2.35 (t, J=11.1 Hz, 1H), 1.87 (dq, J=12.5, 6.3 Hz, 1H), 1.23-1.48 (m, 3H), 1.13-1.22 (m, 1H), 0.96 (d, J=6.8 Hz, 3H), 0.88 (t, J=7.1 Hz, 3 H); LRMS (ESI) m/e 320.3 [(M+H)$^+$, calcd for C$_{19}$H$_{34}$N$_3$O 320.3].

Part D. (2S)-N-(1-(4-(2-methylpentyloxy)phenyl)-2-(4-methylpiperazin-1-yl)ethyl)-2-phenylpropanamide To a solution of (1R)-1-(4-(2-methylpentyloxy)phenyl)-2-(4-methylpiperazin-1-yl)ethanamine.3TFA (79 mg, 0.119 mmol) in dichloromethane (2 mL) at room temperature was added N,N-diisopropylethylamine (0.125 mL, 0.717 mmol) followed by HATU (68.1 mg, 0.179 mmol). The mixture was stirred at room temperature under N$_2$ overnight. The reaction mixture was transferred to a separatory funnel containing saturated aqueous NaHCO$_3$ solution (50 mL). The aqueous layer was extracted with ethyl acetate (3×50 mL). The combined organic layers were washed with brine (50 mL), dried over MgSO$_4$, filtered and concentrated. The product was purified by reverse phase HPLC (acetonitrile/water with 0.1% TFA). The organic solvent was removed on the rotovapor and the aqueous mixture was frozen and placed on the lyophilizer to afford (2S)-N-(1-(4-(2-methylpentyloxy)phenyl)-2-(4-methylpiperazin-1-yl)ethyl)-2-phenylpropanamide (41 mg, 61% yield) as a colorless amorphous solid. LC/MS and HPLC showed that the product is a 1:1 mixture of diastereomers. The total number of protons in the $^1$H NMR is doubled to account for presence of both diastereomers: $^1$H NMR (400 MHz, DMSO-d$_6$) δ 8.29 (t, J=8.4 Hz, 2H), 7.31-7.41 (m, 4H), 7.22-7.29 (m, 7H), 7.16-7.21 (m, 1H), 7.11 (d, 2H), 6.89 (d, J=8.6 Hz, 2H), 6.78 (d, 2H), 4.88-4.99 (m, 2H), 3.62-3.85 (m, 6H), 3.37 (br. s., 4H), 3.20 (br. s., 4H), 2.98 (br. s., 8H), 2.77 (s, 3H), 2.66 (s, 3H), 2.17-2.44 (m, 4H), 1.85 (td, J=13.0, 6.5 Hz, 2H), 1.36 (d, J=7.1 Hz, 3H), 1.29 (d, J=6.8 Hz, 3H), 1.23-1.46 (m, 6H), 1.11-1.22 (m, 2H), 0.96 (d, J=6.8 Hz, 3H), 0.93 (d, J=6.8 Hz, 3H), 0.89 (t, J=6.8 Hz, 3H), 0.87 (t, J=6.5 Hz, 3H); LRMS (ESI) m/e 452.3 [(M+H)$^+$, calcd for $C_{28}H_{42}N_3O_2$ 452.3].

EXAMPLE 37

(2S)-N-((1R)-2-Amino-1-[4-((S)-2-methylbutoxy)phenyl]-ethyl)-2-phenylpropionamide

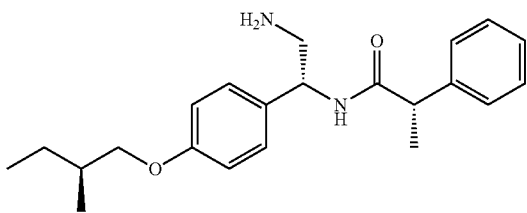

Part A. (R)-Methyl 2-(tert-butoxycarbonylamino)-2-(4-hydroxyphenyl)acetate

A room temperature mixture of (R)-methyl 2-amino-2-(4-hydroxyphenyl)acetate HCl (32 g, 180 mmol), dioxane (360 mL) and water (360 mL) was treated sequentially with triethylamine (100 mL, 720 mmol) and di-t-butyldicarbonate (47 g, 220 mmol). The reaction was maintained at room temperature for 3 h, then quenched with the addition of an aqueous solution of sodium hydroxide (1 N, 40 mL). The resulting mixture was concentrated to remove dioxane, and the aqueous layer was extracted with Et$_2$O (3×200 mL). The combined organic layers were washed with water (1×200 mL) and brine (1×200 mL), then dried over Na$_2$SO$_4$, filtered and concentrated to afford a semisolid that was recrystallized from a minimum amount of hot ethyl acetate to afford (R)-Methyl 2-(tert-butoxycarbonylamino)-2-(4-hydroxyphenyl) acetate (40 g, 78% yield) as a white solid: $^1$H NMR (400 MHz, CDCl$_3$) δ 7.23 (d, J=7.8 Hz, 2H), 6.80 (d, J=7.8 Hz, 2 H), 5.52 (br s, 1H), 5.26 (br d, 1H), 5.05 (s, 1H), 3.73 (s, 3H), 1.45 (s, 9H); LRMS (ESI) m/e 280.0 [(M–H)$^-$, calcd for $C_{14}H_{18}NO_5$ 280.3].

Part B. (2R)-Methyl 2-(tert-butoxycarbonylamino)-(4-((S)-2-methyl-butoxy)phenyl)acetate A 0° C. solution of (R)-Methyl 2-(tert-butoxycarbonylamino)-2-(4-hydroxyphenyl)acetate (2.8 g, 10 mmol), (S)-2-methyl-1-butanol (1.1 mL, 10 mmol), triphenylphosphine (2.6 g, 10 mmol), and tetrahydrofuran (100 mL) was treated dropwise with diisopropylazodicarboxylate (1.9 mL, 10 mmol) via syringe. The resulting reaction mixture was allowed to warm to room temperature and maintained overnight. The reaction was concentrated and the residue was purified by column chromatography on silica gel (5%→10% ethyl acetate in hexanes) to afford (2R)-methyl 2-(tert-butoxycarbonylamino)-(4-((S)-2-methyl-butoxy)-phenyl)acetate (2.8 g, 80% yield) as a clear, colorless oil: $^1$H NMR (400 MHz, CDCl$_3$) δ 7.27 (d, J=7.3 Hz, 2H), 6.88 (d, J=8.6 Hz, 2H), 5.49 (d, J=6.6 Hz, 1H), 5.26 (d, J=7.3 Hz, 1H), 3.81 (dd, J=9.1, 6.1 Hz, 1H), 3.73 (s, 3H), 3.69-3.76 (m, 1H), 1.86 (dq, J=13.1, 6.5 Hz, 1H), 1.52-1.61 (m, 1H), 1.45 (s, 9H), 1.22- 1.33 (m, 2H), 1.02 (d, J=6.8 Hz, 3H), 0.95 (t, J=7.5 Hz, 3H); LRMS (ESI) m/e 352.2 [(M+H)$^+$, calcd for $C_{19}H_{30}NO_5$ 352.5].

Part C. t-Butyl (R)-2-Hydroxy-1-(4-((S)-2-methylbutoxy)phenyl)ethylcarbamate

A room temperature suspension of lithium aluminum hydride (320 mg, 8.5 mmol) and tetrahydrofuran (50 mL) was treated slowly with a solution of (2R)-methyl 2-(tert-butoxycarbonylamino)-(4-((S)-2-methyl-butoxy)-phenyl)acetate and tetrahydrofuran (40 mL). The resulting reaction mixture was maintained 30 min, then treated with ethyl acetate (12 mL) and an aqueous solution of potassium hydroxide (10% wt/wt, 24 mL). The mixture was allowed to stir for 1 h, then dried with MgSO$_4$, filtered and concentrated to afford t-butyl (R)-2-hydroxy-1-(4-((S)-2-methylbutoxy)phenyl)ethylcarbamate (2.2 g, 88% yield) as a yellow solid: $^1$H NMR (400 MHz, CDCl$_3$) δ 7.22 (d, J=8.6 Hz, 2H), 6.90 (d, J=8.8 Hz, 2H), 5.12 (d, J=6.3 Hz, 1H), 4.74 (br. s., 1H), 3.80-3.87 (m, 3H), 3.74 (dd, J=9.1, 6.6 Hz, 1H), 1.87 (dq, J=13.0, 6.5 Hz, 1H), 1.53-1.64 (m, 2H), 1.45 (s, 9H), 1.22-1.34 (m, 1H), 1.03 (d, J=6.6 Hz, 3H), 0.97 (t, J=7.5 Hz, 3H); LRMS (ESI) m/e 324.1 [(M+H)$^+$, calcd for $C_{18}H_{30}NO_4$ 324.4].

Part D. t-Butyl (R)-2-(1,3-dioxo-1,3-dihydroisoindol-2-yl)-1-(4-((S)-2-methylbutoxy)phenyl)ethylcarbamate A precooled (0° C.) solution of tert-butyl (R)-2-hydroxy-1-(4-((S)-2-methylbutoxy)phenyl)ethyl carbamate (1.3 g, 4.0 mmol), phthalimide (600 mg, 4.1 mmol), triphenylphosphine (1.1 g, 4.1 mmol) and tetrahydrofuran (40 mL) was treated dropwise via syringe with diisopropylazodicarboxylate (0.80 mL, 4.1 mmol). The resulting reaction mixture was maintained at room temperature overnight, then concentrated and the resulting oil was purified by column chromatography on silica gel (5%→20% ethyl acetate in hexanes) to afford tert-butyl (R)-2-(1,3-dioxo-1,3-dihydroisoindol-2-yl)-1-(4-((S)-2-methylbutoxy)phenyl)ethylcarbamate (800 mg, 45% yield) as a white solid: $^1$H NMR (400 MHz, CDCl$_3$) δ 7.86-7.89 (m, 2H), 7.70-7.75 (m, 2H), 7.26-7.31 (m, 2H), 6.90 (d, J=8.6 Hz, 2H), 5.16-5.24 (m, 1H), 5.04-5.08 (m, 1H), 3.90-3.95 (m, 1H), 3.83 (dd, J=8.6, 5.8 Hz, 1H), 3.74 (dd, J=8.8, 6.6 Hz, 1H), 1.83-1.89 (m, 1H), 1.51-1.61 (m, 2H), 1.26 (s, 9H), 1.25-1.30 (m, 1H), 1.03 (d, J=6.8 Hz, 3H), 0.97 (t, J=7.5 Hz, 3H); LRMS (ESI) m/e 453.2 [(M+H)$^+$, calcd for $C_{26}H_{33}N_2O_5$ 453.6].

Part E. (S)-N-((R)-2-(1,3-Dioxo-1,3-dihydroisoindol-2-yl)-1-(4-((S)-2-methylbutoxy)-phenyl)-ethyl)-2-phenyl-propionamide A precooled (0° C.) solution of t-butyl (R)-2-(1,3-dioxo-1,3-dihydroisoindol-2-yl)-1-(4-((S)-2-methylbutoxy)phenyl)ethylcarbamate (250 mg, 0.55 mmol) and dichloromethane (10 mL) was treated dropwise with trifluoroacetic acid (2 mL). The resulting solution was maintained at room temperature for 16 h, then concentrated to afford a yellow oil that was dissolved in dichloromethane (5 mL) and added to a room temperature solution of 2-thiophen-2-yl-cyclopropane carbonylchloride (100 mg, 0.60 mmol), triethylamine (0.20 mL, 1.4 mmol) and dichloromethane (4 mL). The resulting reaction was maintained overnight, then transferred to a separatory funnel and partitioned between ethyl acetate (15 mL) and saturated aqueous sodium bicarbonate (15 mL). The layers were separated, and the aqueous layer was extracted with ethyl acetate (15 mL). The combined organic layers were washed with water (15 mL) and brine (15 mL), then dried (MgSO$_4$), filtered and concentrated to afford a residue that was purified by column chromatography on silica gel (10%→50% ethyl acetate in hexanes) to afford (S)-N-((R)-2-(1,3-dioxo-1,3-dihydroisoindol-2-yl)-1-(4-((S)-2-methyl-butoxy)-phenyl)-ethyl)-2-phenyl-propionamide (220 mg, 81% yield) as a white powder: $^1$H NMR (400 MHz, CDCl$_3$) δ 7.87 (dd, J=5.6, 3.0 Hz, 2H), 7.76 (dd, J=5.4, 3.2 Hz, 2H), 7.22-7.34 (m, 5H), 7.05 (d, J=8.6 Hz, 2H), 6.80 (d, J=8.8 Hz, 2H), 6.27 (d, J=8.1 Hz, 1H), 5.26 (td, J=8.3, 5.3 Hz, 1H), 3.86-3.90 (m, 2H), 3.79 (dd, J=9.1, 6.1 Hz, 1H), 3.70 (dd, J=8.8, 6.6 Hz, 1H), 3.50 (q, J=7.2 Hz, 1H), 1.80-1.90 (m, 1H), 1.52-1.59 (m, 1H), 1.39 (d, J=7.1 Hz, 3H), 1.23-1.32 (m, 1H), 1.01 (d, J=6.8 Hz, 3H), 0.96 (t, J=7.5 Hz, 3H); LRMS (ESI) m/e 485.0 [(M+H)$^+$, calcd for C$_{30}$H$_{32}$N$_2$O$_4$ 485.6].

Part F. (2S)-N-((1R)-2-Amino-1-[4-((S)-2-methylbutoxy)phenyl]-ethyl)-2-phenylpropionamide A mixture of (S)-N-((R)-2-(1,3-dioxo-1,3-dihydroisoindol-2-yl)-1-(4-((S)-2-methyl-butoxy)-phenyl)-ethyl)-2-phenyl-propionamide (320 mg, 0.66 mmol) and ethanol (20 mL) was treated dropwise with hydrazine monohydrate (0.32 mL, 6.6 mmol), and the resulting reaction was maintained at 60° C. overnight. The mixture was allowed to cool to room temperature and the solids were removed by filtration. The filtrate was concentrated to dryness, and triturated with ethyl acetate (15 mL), and the mixture was filtered. The collected solids were air dried, then dissolved in diethyl ether (5 mL). The resulting solution was treated with concentrated HCl (0.05 mL), and the precipitate was collected by filtration to afford (2S)-N-((1R)-2-amino-1-[4-((S)-2-methylbutoxy)phenyl]-ethyl)-2-phenylpropionamide (120 mg, 52% yield) as a white solid: $^1$H NMR (400 MHz, MeOD) δ 7.21-7.31 (m, 5H), 7.09 (d, J=8.6 Hz, 2H), 6.84 (d, J=8.8 Hz, 2H), 5.12 (dd, J=8.8, 5.8 Hz, 1H), 3.81 (dd, J=9.3, 6.1 Hz, 1H), 3.70-3.77 (m, 2H), 3.23-3.30 (m, 2H), 1.81 (s, 1H), 1.57 (ddd, J=13.4, 7.6, 5.8 Hz, 1H), 1.47 (d, J=6.8 Hz, 3H), 1.24-1.33 (m, 1H), 1.02 (d, J=6.8 Hz, 3H), 0.96 (t, J=7.5 Hz, 3H); LRMS (ESI) m/e 355.1 [(M+H)$^+$, calcd for C$_{22}$H$_{31}$N$_2$O$_2$ 355.5].

EXAMPLE 38

(S)-N-{(R)-1-[4-((S)-2-Methyl-butoxy)-phenyl]-2-propylamino-ethyl}-2-phenylpropionamide

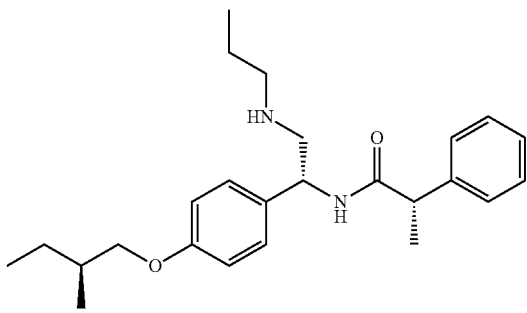

Part A: (S)-N-{(R)-2-Hydroxy-1-[4-((S)-2-methyl-butoxy)-phenyl]-ethyl}-2-phenylpropionamide To a solution of (S)-2-phenyl-propionic acid (180 mg, 1.20 mmol) dissolved in 20 mL THF was added 1,1-carbonyldiimidazole (214 mg, 1.32 mmol). The resulting mixture was stirred at rt for 2 hr. Then the aminoalcohol (311.4 mg, 1.20 mmol) was added followed by triethylamine (0.33 mL, 2.4 mmol). The resulting mixture was stirred at rt for 3 hr. It was diluted with EtOAc, and quenched with water. The organic layer was washed with water and brine, and then dried over MgSO$_4$. It was concentrated and purified on a 40 g column using 10-50% EtOAc/hexane to give 325 mg (76%) of the product. 1H NMR (400 MHz, CDCl$_3$) δ 7.26-7.40 (m, 5H), 6.93-7.01 (m, 2H), 6.77-6.83 (m, 2H), 6.12 (d, J=6.8 Hz, 1H), 4.91-5.04 (m, 1H), 3.74-3.88 (m, 3H), 3.61-3.73 (m, 2H), 1.85 (dq, J=13.0, 6.5 Hz, 1H), 1.56-1.66 (m, 1H), 1.51-1.56 (m, 3H), 1.19-1.33 (m, 1H), 1.01 (d, J=6.6 Hz, 3H), 0.95 (t, J=7.5 Hz, 3H); LCMS (ESI) m/e calcd 356.2 [(M+H)$^+$, for C$_{22}$H$_{30}$NO$_3$ 356.2].

Part B: (S)-N-{(R)-2-(1,3-Dioxo-1,3-dihydro-isoindol-2-yl)-1-[4-((S)-2-methylbutoxy)-phenyl]-ethyl}-2-phenyl-propionamide To a solution of the alcohol (200 mg, 0.56 mmol), phthalimide (90 mg, 0.62 mmol) and PPh$_3$ (162 mg, 0.62 mmol) dissolved in 15 mL THF at 0° C. was added DIAD (125 mg, 0.62 mmol). After 10 min the ice bath was removed and the reaction mixture stirred at rt for 3 hr. It was concentrated and purified by column chromatography on silica gel using 2%→40% EtOAc in hexane to obtain 243 mg (89%) of the product.

Part C: (S)-N-{(R)-2-Amino-1-[4-((S)-2-methyl-butoxy)-phenyl]-ethyl}-2-phenylpropionamide To a solution of (S)-N-{(R)-2-(1,3-dioxo-1,3-dihydro-isoindol-2-yl)-1-[4-((S)-2-methyl-butoxy)-phenyl]-ethyl}-2-phenyl-propionamide dissolved in 10 mL of EtOH, was added anhydrous hydrazine. The resulting mixture was heated to 55° C. 1.5 h. It was cooled to rt, and diluted with EtOAc. The solids were filtered off, and the filtrate concentrated and was purified by column chromatography on silica gel using 0%→10% MeOH/DCM to obtain 109 mg (96%) of the desired product. $^1$H NMR (400 MHz, MeOD) δ 7.19-7.33 (m, 5H), 7.05-7.12 (m, 2H), 6.79-6.88 (m, 2H), 5.12 (dd, J=8.8, 5.8 Hz, 1H), 3.77-3.86 (m, 1H), 3.69-3.77 (m, 2H), 3.21-3.29 (m, 2H), 1.81 (s, 1H), 1.57 (ddd, J=13.4, 7.6, 5.8 Hz, 1H), 1.47 (d, J=6.8 Hz, 3H), 1.22-1.35 (m, 1H), 1.02 (d, J=6.8 Hz, 3H), 0.96 (t, J=7.5 Hz, 3H); LCMS m/e calcd 355.2 [(M+H)$^+$, for C$_{22}$H$_{31}$N$_2$O$_2$ 355.2].

Part D: (S)-N-{(R)-1-[4-((S)-2-Methyl-butoxy)-phenyl]-2-propylamino-ethyl}-2-phenyl-propionamide To a solution of the amine (25 mg, 0.071 mmol) and the aldehyde (4.5 mg, 0.077 mmol) in 5 mL MeOH and 1 mL AcOH was added 0.071 mL of 1.0 M borane-THF at 0° C. After 4 hr stirring at 0° C., it was diluted with EtOAc, and quenched with aq. K$_2$CO$_3$. The organic layer was washed with aq. NaHCO$_3$, and brine, and then dried over MgSO$_4$. It was concentrated and purified on the neutral prep HPLC to obtain 9 mg (32%) of the product. $^1$H NMR (400 MHz, MeOD) δ 8.31 (br. s., 1H), 7.22-7.30 (m, 5H), 7.08 (d, J=5.2 Hz, 2H), 6.83 (d, J=5.0 Hz, 2H), 5.13 (t, J=7.2 Hz 1H), 3.71-3.84 (m, 2H), 3.43 (q, J=4.3 Hz, 1H), 3.21-3.31 (m, 2H), 2.54 (t, J=6.9 Hz, 2H), 2.12-2.24 (m, 1H), 1.51-1.63 (m, 4H), 1.31 (d, J=7.1 Hz, 3 H), 0.84-0.99 (m, 9H); LCMS m/e calcd 397.3 [(M+H)+, for $C_{25}H_{37}N_2O_2$ 397.2]; HPLC retention time=1.61 min.

EXAMPLE 39

(S)-N-{(1R,2R)-2-Hydroxy-1-[4-((S)-2-methyl-butoxy)-phenyl]-propyl}-2-phenylpropionamide

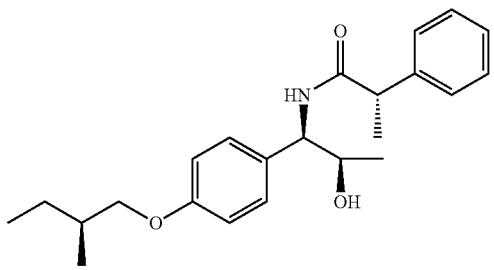

Part A. ((E)-4-Propenyl)-phenol

Trans-anethole (0.5 mL, 3.34 mmol), potassium hydroxide (4 g, 71 mmol) and ethanol (6 mL) were mixed and sealed in a microwave tube. The reaction mixture was heated at 160° C. in microwave oven at very high setting for 3×30 minutes. The reaction was quenched with saturated citric acid. The aqueous phase was extracted by ethyl acetate (3×10 mL). The combined organic layers were dried over $MgSO_4$, filtered and concentrated to give a yellow crude product. The crude product was purified via column chromatography on silica gel with a gradient of 0%→50% of ethyl acetate in hexanes to afford the title product (0.10 g, 22% yield): $^1$H NMR (400 MHz, $CDCl_3$) δ 7.23 (m, 2H), 6.80 (m, 2H), 6.36 (dd, J=15.7, 1.8 Hz, 1H), 6.11 (dq, J=15.7, 6.6 Hz, 1H), 5.12 (s, 1H), 1.89 (m, 3H); LCMS (ESI) m/e 133.1 [(M–H)–, calcd for $C_9H_{11}O$ 133.2].

Part B. 1-((S)-2-Methyl-butoxy)-4-((E)-propenyl)-benzene ((E)-4-Propenyl)-phenol (0.10 g, 0746 mmol), (S)-2-methylbutyl bromide (0.28 mL, 2.23 mmol) and potassium carbonate (0.51 g, 3.68 mmol) were mixed in DMF (7 mL). The reaction mixture was heated at 80° C. for 2 hrs. A saturated solution of ammonium chloride was added to quench the reaction. The aqueous phase was extracted by ethyl acetate (3×7 mL). The combined organic layers were dried over $MgSO_4$, filtered and concentrated to give yellow oil. The crude product was purified via column chromatography on silica gel with a gradient of 0%→50% of ethyl acetate in hexanes to afford the title product (0.10 g, 66% yield).

Part C. {(1R,2R)-2-Hydroxy-1-[4-((S)-2-methyl-butoxy)-phenyl]-propyl}-carbamic acid t-butyl ester To a solution of t-butyl carbamate (0.18 g, 1.50 mmol) in n-propanol (2.0 mL) was added the solution of sodium hydroxide (0.062 g, 1.50 mmol) in water (3.7 mL), then added freshly made t-butyl hypochloride (0.18 mL, 1.50 mmol). The mixture was stirred for 5 minutes at room temperature. This reaction mixture was then placed in an ice-bath, (DHQD)$_2$PHAL (0.023 g, 0.029 mmol) in n-propanol (2.0 mL) and 1-((S)-2-methyl-butoxy)-4-((E)-propenyl)-benzene (0.10 g, 0.49 mmol) in n-propanol (3.4 mL) were added sequentially, stirred for 6 minutes. $K_2OsO_2$ $2H_2O$ (0.007 g, 0.02 mmol) was added directly at 0° C. The final reaction mixture was stirred for 1.5 hrs to generate a light yellow clear solution. A saturated solution of sodium sulfite (10 mL) was added to quench the reaction at 0° C. Excessive n-propanol was removed in a high vacuum. The aqueous phase was extracted by ethyl acetate (3×10 mL). The combined organic layers were washed with brine (2×10 mL), then dried over $MgSO_4$, filtered and concentrated to give a yellow crude solid. The crude product was purified via column chromatography on silica gel with a gradient of 0%→100% of ethyl acetate in hexanes to afford a white solid (0.126 g, 76% yield) of the title compound.

Part D. (1R,2R)-1-Amino-1-[4-((S)-2-methyl-butoxy)-phenyl]-propan-2-ol.HCl

To a solution of {(1R,2R)-2-hydroxy-1-[4-((S)-2-methyl-butoxy)-phenyl]-propyl}-carbamic acid t-butyl ester (0.126 g 0.3 mmol), in dichloromethane (10 mL) in an ice bath was added HCl in 1,4-dioxane (4M, 1 mL). The final mixture was then stirred at room temperature for 1 hr. The excessive solvent was removed in vacuum to give a white solid, which was used as it for next step.

Part E. (S)-N-{(1R,2R)-2-Hydroxy-1-[4-((S)-2-methyl-butoxy)-phenyl]-propyl}-2-phenyl-propionamide To a solution of (S)-(+)-2-phenylpropionic acid (0.067 g, 0.449 mmol) in dichloromethane (5 mL) in an ice-bath was added oxalyl chloride (0.39 mL, 4.49 mmol), then DMF (0.02 mL) under nitrogen. The reaction mixture was stirred for 30 minutes at 0° C. The excessive solvent was removed on ratovapor and dried under high vacuum for 2 hrs to give the corresponding acid chloride. A separate 50 mL round-bottom flask was charged with (1R,2R)-1-amino-1-[4-((S)-2-methyl-butoxy)phenyl]-propan-2-ol.HCl salt (0.37 mmol), dichloromethane (6 mL) and triethylamine (0.3 mL, 1.85 mmol) in an ice cold bath under nitrogen. The acid chloride mentioned above, in dichloromethane (2 mL) was added into the reaction mixture dropwise. The final reaction mixture was stirred for 1.5 hrs at room temperature. The finished reaction was quenched with water. The organic phase was washed with brine (3×10 mL), dried over $MgSO_4$, filtrated, concentrated in vacuum and purified via column chromatography on silica gel with a gradient of 0%→100% of ethyl acetate in hexane to give a white solid (0.013 g, 10% yield). $^1$H NMR (400 MHz, $CDCl_3$) δ 7.33 (m, 5H), 6.93 (d, J=8.8 Hz, 2H), 6.80 (m, 2H), 6.05 (d, J=8.3 Hz, 1H), 4.82 (dd, J=8.2, 3.7 Hz, 1H), 4.00 (br. s., 1H), 3.74 (m, 3H), 1.96 (d, J=3.0 Hz, 1H), 1.85 (d, J=6.6 Hz, 1H), 1.54 (m, 3H), 1.27 (m, 2H), 1.16 (d, J=6.3 Hz, 3H), 1.02 (m, 3H), 0.96 (t, J=7.5 Hz, 3H); LCMS (ESI) m/e 370.4 [(M+H), calcd. for $C_{23}H_{32}NO_3$ 370.5].

EXAMPLE 40

(S)-N-((R)-(4-Isobutoxyphenyl)((R)-pyrrolidin-2-yl)methyl)-2-phenylpropanamide

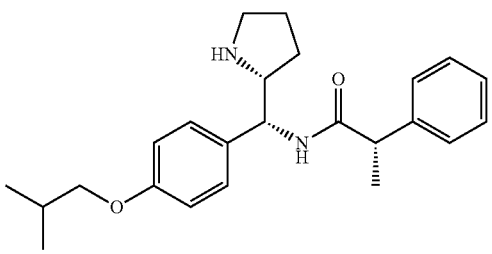

Part A. (R)-tert-Butyl 2-(methoxy(methyl)carbamoyl)pyrrolidine-1-carboxylate N-(tert-Butoxycarbonyl)-D-proline (1.505 g, 6.99 mmol), DCC (1.443 g, 6.99 mmol), HOBt (1.071 g, 6.99 mmol), and Hunig's base (2.78 mL, 15.89 mmol) in DCM (31.8 mL) were stirred at room temperature for 1 h. N,O-Dimethylhydroxylamine hydrochloride (0.62 g, 6.36 mmol) and DMAP (0.078 g, 0.636 mmol) were added and the solution stirred at room temperature for 4 h. The mixture was concentrated in vacuo. The residue was purified by column chromatography on silica gel (10%→100% ethyl acetate in hexanes). Obtained (R)-tert-butyl 2-(methoxy(methyl)carbamoyl)pyrrolidine-1-carboxylate (794 mg, 3.07 mmol, 48.4% yield) as a colorless oil. Rotomers (a and b) seen in NMR: $^1$H NMR (500 MHz, CDCl$_3$) δ 4.52-4.76 (m, 1H), 3.77 (s, 1.5 Ha), 3.71 (s, 1.5 Hb), 3.51-3.64 (m, 1H), 3.33-3.51 (m, 1H), 3.18 (s, 3H), 2.08-2.27 (m, 1H), 1.74-2.04 (m, 3H), 1.45 (s, 4.5 Ha), 1.40 (s, 4.5 Hb); LRMS (ESI) m/e 158.76.

Part B. (R)-tert-Butyl 2-(4-(benzyloxy)benzoyl)pyrrolidine-1-carboxylate

To (R)-tert-butyl 2-(methoxy(methyl)carbamoyl)pyrrolidine-1-carboxylate (716 mg, 2.77 mmol) in THF (27.700 mL) at 0° C. was added (4-(benzyloxy)phenyl)magnesium bromide (8.32 mL, 16.63 mmol) dropwise. After complete addition, the solution was heated to 65° C. for 1 h. The reaction was cooled to 0° C., quench carefully with 1N HCl and extracted with EtOAc (3×). The combined organic layers were washed with brine, dried over MgSO$_4$, filtered and concentrated. The residue was purified by column chromatography on silica gel (5%→60% ethyl acetate in hexanes) to afford (R)-tert-butyl 2-(4-(benzyloxy)benzoyl)pyrrolidine-1-carboxylate (533 mg, 1.397 mmol, 50.4% yield) as an amorphous yellow solid. $^1$H NMR (400 MHz, CDCl$_3$) δ 7.87-8.00 (m, 2H), 7.29-7.47 (m, 5H), 6.95-7.07 (m, 2H), 5.13-5.31 (m, 1H), 5.10-5.13 (m, J=3.78 Hz, 2H), 3.40-3.73 (m, 2H), 2.19-2.35 (m, 1H), 1.82-1.98 (m, 3H), 1.21-1.30 (m, 9H); LRMS (ESI) m/e 282.17 [(M-Boc+H)$^+$, calcd for $C_{18}H_{20}NO_2$ 282.15]; m/e 404.11 [(M+Na)$^+$, calcd for $C_{23}H_{27}NNaO_4$ 404.18].

Part C. (R)-tert-Butyl 2-(amino(4-(benzyloxy)phenyl)methyl)pyrrolidine-1-carboxylate A solution of (R)-tert-butyl 2-(4-(benzyloxy)benzoyl)pyrrolidine-1-carboxylate (247 mg, 0.648 mmol) and dry ammonium acetate (399 mg, 5.18 mmol) in methanol (13.0 mL) was stirred at room temperature for 30 min. To this was added sodium cyanotrihydroborate (81 mg, 1.295 mmol) and the reaction mixture heated to 60° C. for 24 h. An additional portion of sodium cyanotrihydroborate (81 mg, 1.30 mmol) was added and the heating continued at 60° C. for 48 h. The reaction solution was cooled to room temperature, quenched with water and extracted with ethyl acetate (3×). The combined organic layers were washed with brine, dried over MgSO$_4$, filtered and concentrated. The residue was purified by column chromatography on silica gel (5%→60% ethyl acetate in hexanes). Obtained (R)-tert-butyl 2-(amino(4-(benzyloxy)phenyl)methyl)pyrrolidine-1-carboxylate (100 mg, 0.262 mmol, 100% yield) as a slightly yellow oil that was carried on without further purification. $^1$H NMR (400 MHz, CDCl$_3$) δ 7.27-7.46 (m, 5H), 6.90-7.15 (m, 4H), 4.97-5.14 (m, 2H), 4.10-4.53 (m, 1H), 3.27-3.64 (m, 1H), 2.55-2.78 (m, 1H), 2.26-2.45 (m, 1H), 1.54-2.11 (m, 4H), 1.45-1.54 (m, 9H); LRMS (ESI) m/e 383.13, 404.11 [(M+H)$^+$, calcd for $C_{23}H_{31}N_2O_3$ 383.23].

Part D. (R)-tert-Butyl 2-((R)-(4-(benzyloxy)phenyl)((S)-2-phenylpropanamido)methyl)pyrrolidine-1-carboxylate and (R)-tert-Butyl 2-((S)-(4-(benzyloxy)phenyl)((S)-2-phenylpropanamido)methyl)pyrrolidine-1-carboxylate (S)-2-Phenylpropanoic acid (107 mg, 0.713 mmol), EDC (137 mg, 0.713 mmol), HOBt (109 mg, 0.713 mmol), and Hunig's base (249 μL, 1.426 mmol) in DCM (6480 μL) were stirred at room temperature for 10 min. (2R)-tert-Butyl 2-(amino(4-(benzyloxy)phenyl)methyl)pyrrolidine-1-carboxylate (248 mg, 0.648 mmol) was added and the solution stirred at room temperature for 4 h. The reaction was quenched with 10% aqueous citric acid and extracted with DCM (3×). The combined organic layers were washed with 10% aqueous citric acid (2×), saturated aqueous sodium bicarbonate (2×), brine (1×), dried over MgSO$_4$, filtered and concentrated. The residue was purified by column chromatography on silica gel (10%→60% ethyl acetate in hexanes). Two diastereomers were obtained. (R)-tert-Butyl 2-((R)-(4-(benzyloxy)phenyl)((S)-2-phenylpropanamido)methyl)pyrrolidine-1-carboxylate (78 mg, 0.114 mmol, 17.54% yield) was obtained as a colorless oil (peak 1). $^1$H NMR (400 MHz, CDCl$_3$) δ 8.01 (d, J=6.29 Hz, 1H), 7.33-7.43 (m, 6 H), 7.11-7.23 (m, 4H), 7.06 (d, J=8.56 Hz, 2H), 6.82 (d, J=8.56 Hz, 2H), 4.99 (s, 2H), 4.50 (dd, J=10.83, 6.04 Hz, 1H), 4.01-4.11 (m, 1H), 3.28-3.49 (m, 3H), 1.76-2.07 (m, 2H), 1.53-1.68 (m, 2H), 1.50 (s, 9H), 1.40 (d, J=7.05 Hz, 3H); LRMS (ESI) m/e 515.40 [(M+H)$^+$, calcd for $C_{32}H_{39}N_2O_4$ 515.29]; m/e 513.60 [(M-H)$^-$, calcd for $C_{32}H_{37}N_2O_4$ 513.28]. (R)-tert-Butyl 2-((S)-(4-(benzyloxy)phenyl)((S)-2-phenylpropanamido)methyl)pyrrolidine-1-carboxylate (122 mg, 0.183 mmol, 28.2% yield) was obtained as a colorless oil (peak 2). $^1$H NMR (400 MHz, CDCl$_3$) δ 8.95 (d, J=6.30 Hz, 1H), 7.23-7.44 (m, 10H), 7.02 (d, J=8.56 Hz, 2H), 6.84 (d, J=8.56 Hz, 2H), 5.01 (s, 2H), 4.68-4.76 (m, 1H), 4.02-4.09 (m, 1H), 3.54 (q, J=7.13 Hz, 1H), 3.09-3.22 (m, 1H), 2.41-2.54 (m, 1H), 1.94-2.07 (m, 1H), 1.64-1.74 (m, 1H), 1.49 (d, J=7.05 Hz, 3H), 1.47 (s, 9H), 1.30-1.40 (m, 2H); LRMS (ESI) m/e 515.30 [(M+H)$^+$, calcd for $C_{32}H_{39}N_2O_4$ 515.29]; m/e 513.50 [(M-H)$^-$, calcd for $C_{32}H_{37}N_2O_4$ 513.28].

Part E. (S)-N-((R)-(4-(Benzyloxy)phenyl)((R)-pyrrolidin-2-yl)methyl)-2-phenylpropanamide A solution of (S)-tert-butyl 2-((R)-(4-(benzyloxy)phenyl)((S)-2-phenylpropanamido)methyl)pyrrolidine-1-carboxylate (386 mg, 0.750 mmol) in HCl (2M in diethyl ether) (3.750 mL, 7.50 mmol) was stirred at room temperature for 4 h, then concentrated in vacuo. The residue was purified by HPLC (50% methanol/water with 0.1% TFA) to afford (S)-N-((R)-(4-(benzyloxy)phenyl)((R)-pyrrolidin-2-yl)methyl)-2-phenylpropanamide (14.7 mg, 0.034 mmol, 61.9% yield) as a slightly yellow oil. $^1$H NMR (400 MHz, CDCl$_3$) δ 7.23-7.43 (m, 11H), 6.94 (d, J=8.56 Hz, 2H), 6.81 (d, J=8.81 Hz, 2H), 6.64 (d, J=5.79 Hz, 1H), 4.99 (s, 1H), 4.79 (dd, J=8.18, 3.15 Hz, 1H), 3.67 (q, J=7.22 Hz, 1H), 3.31 (td, J=7.68, 3.27 Hz, 1H), 2.72 (td, J=6.67, 2.27 Hz, 1H), 1.72-1.84 (m, 2H), 1.60 (td, J=13.28, 6.17 Hz, 2H), 1.48-1.55 (m, 4H), 1.33-1.45 (m, 1H); LRMS (ESI) m/e 415.40 [(M+H)$^+$, calcd for $C_{27}H_{31}N_2O_2$ 415.24].

Part F. (R)-tert-Butyl 2-((R)-(4-hydroxyphenyl)((S)-2-phenylpropanamido)methyl)pyrrolidine-1-carboxylate (R)-tert-Butyl 2-((R)-(4-(benzyloxy)phenyl)((S)-2-phenylpropanamido)methyl)pyrrolidine-1-carboxylate (78 mg, 0.152 mmol) and palladium on carbon (10% wt) (36 mg, 0.034 mmol) in methanol (3.031 mL) was hydrogenated under 60 psi hydrogen gas for 4 h. The mixture was filtered through diatomaceous earth (Celite®) eluting with EtOAc and the filtrate concentrated in vacuo. Obtained (R)-tert-butyl 2-((R)-(4-hydroxyphenyl)((S)-2-phenylpropanamido)methyl)pyrrolidine-1-carboxylate (29.1 mg, 0.069 mmol, 98% yield) as a colorless oil which was carried forward without further purification. $^1$H NMR (400 MHz, CDCl$_3$) δ 8.17 (d, J=5.79 Hz, 1H), 7.25-7.31 (m, 1H), 7.13-7.23 (m, 4H), 6.91 (d, J=8.31 Hz, 2H), 6.52 (d, J=8.56 Hz, 2H), 4.45 (dd, J=10.83, 6.04 Hz, 1H), 3.99-4.14 (m, 1H), 3.27-3.57 (m, 3H), 1.72-2.07 (m, 2H), 1.59 (t, J=11.46 Hz, 2H), 1.51 (s, 9H), 1.42 (d, J=7.30 Hz, 3H); LRMS (ESI) m/e 447.20 [(M+Na)$^+$, calcd for $C_{25}H_{32}N_2NaO_4$ 447.23].

Part G. (R)-tert-Butyl 2-((R)-(4-isobutoxyphenyl)((S)-2-phenylpropanamido)methyl)pyrrolidine-1-carboxylate A solution of 2-methyl-1-propanol (6.52 μL, 0.071 mmol), DEAD (11.19 μL, 0.071 mmol), and triphenylphosphine (18.53 mg, 0.071 mmol) in THF (520 μL) in a microwave vial was stirred at room temperature for 10 min. (R)-tert-Butyl 2-((R)-(4-hydroxyphenyl)((S)-2-phenylpropanamido)methyl)pyrrolidine-1-carboxylate (30 mg, 0.071 mmol) was added and the solution heated at 140° C. in a microwave (Biotage) for 20 min. The crude mixture was filtered through a plug of silica gel eluting with 50% EtOAc in hexanes. The filtrate was concentrated in vacuo and carried directly into the next reaction. LRMS (ESI) m/e 481.50 [(M+H)$^+$, calcd for $C_{29}H_{41}N_2O_4$ 481.31].

Part H. (S)-N-((R)-(4-Isobutoxyphenyl)((R)-pyrrolidin-2-yl)methyl)-2-phenylpropanamide (R)-tert-Butyl 2-((R)-(4-isobutoxyphenyl)((S)-2-phenylpropanamido)methyl)pyrrolidine-1-carboxylate (34.1 mg, 0.071 mmol) in hydrogen chloride (2M in diethyl ether) (355 mL, 0.710 mmol) was stirred at room temperature for 6 h then the solution was concentrated in vacuo. The residue was purified by HPLC (20%→100% acetonitrile/water with 0.1% TFA) to afford after preparing the free base, (S)-N-((R)-(4-isobutoxyphenyl)((R)-pyrrolidin-2-yl)methyl)-2-phenylpropanamide (4.6 mg, 0.012 mmol, 16.69% yield over two steps). $^1$H NMR (400 MHz, CDCl$_3$) δ 7.40 (br s, 1H), 7.26-7.35 (m, 5H), 6.98 (d, J=8.56 Hz, 2H), 6.74 (d, J=8.81 Hz, 2H), 4.93 (t, J=7.18 Hz, 1H), 3.77 (q, J=7.05 Hz, 1H), 3.64-3.67 (m, 1H), 3.62 (d, J=6.55 Hz, 2H), 2.97-3.06 (m, 2H), 2.87-2.96 (m, 1H), 1.96-2.09 (m, 1H), 1.67-1.83 (m, 3H), 1.53-1.57 (m, 1H), 1.50 (d, J=7.05 Hz, 3H), 0.97 (d, J=6.80 Hz, 6H); LRMS (ESI) m/e 381.30 [(M+H)$^+$, calcd for $C_{24}H_{33}N_2O_2$ 381.25].

BIOLOGICAL ACTIVITY

Materials:

96 well GTPγS assay plates were purchased from Perkin Elmer. Wheat Germ Agglutinin PVT SPA beads and $^{35}$S-GTPγS were purchased from Amersham GDP, GTPγS and all buffer reagents were from Sigma. 384 well white NBS plates were purchased from corning. Pertussis toxin was purchased from Calbiochem. All cell culture reagents were purchased from Invitrogen. Forskolin was purchased from Sigma. The cAMP HTRF kit was purchased fron Cisbio International.

Methods:

GTPγS Assay

The GTPγS assay buffer consisted of 10 mM MgCl$_2$, 180 mM NaCl, 200 uM GDP, 0.167 mg/mL DTT, 1 mM EGTA and 20 mM HEPES pH7.4. This buffer was used for dilution of membranes, beads, and $^{35}$S GTPγS components. To each well of the 96 well assay plate 48 ul assay buffer, 2 ul of 100× compound, 50 ul membrane solution (0.2 ug/ul), 50 ul $^{35}$S GTPγS solution (0.8 nM) and 50 ul of SPA beads (10 mg/mL). Non-specific binding was determined by the addition of cold GTPγS to control wells. The plates were sealed with clear sealing tape and incubated at room temperature for 1 hour. GTPγS activity was detected using a Wallac Micro-Beta Trilux liquid scintillation counter. Non-specific binding was determined using 10 uM cold GTPγS.

cAmp HTRF Assay

The cAMP HTRF assay is modified from the Cisbio International kit procedure 62AM4PEJ. Assay plates were prepared by stamping 0.1 ul of 100× compound stock solutions diluted in DMSO or DMSO alone into 384 well NBS plates. The cAMP HTRF assay was performed using cells in suspension. The cAMP HTRF assay buffer consisted of Hank's Balanced Salt Solution (HBSS), 2 mM CaCl2, 5 mM MgCl2, 20 mM HEPES and 1 mM 3-isobutyl-1-methylxanthine (IBMX) (added fresh at the time of assay). For pertussis toxin treatment pertussis toxin (100 ng/mL) was added to culture medium for 16 hours prior to assay. Confluent cells were disrupted with cell dissociation buffer count cells then centrifuged at 1000×g for 5 minutes. The cell pellet was resuspended in assay buffer alone for basal cAMP measurements or with 0.75 uM forskolin (added immediately prior to addition to wells) for addition to all other wells. Using a Multidrop 384 (Lab systems) 10 ul of cell suspension was added to each well containing compound or DMSO. The plates were incubated at room temperature for 30 minutes covered. During this time the cAMP standard curve was prepared as per manufacturer's instruction. At the end of the incubation 10 ul of anti-cAMP cryptate and 10 ul cAMP-XL, diluted in manufacturer's lysis buffer, were added to each well. The plated were incubated at room temperature for 60 minutes covered then read on an Envision plate reader (Perkin Elmer) and the 665 nm/620 nm fluorescence ratio determined Fluorescence ratio values were converted to molar cAMP concentrations from the standard curve using the GraphPad Prism program.

Table 2 shows EC$_{50}$ values for select compounds of the present disclosure: Ranges are as follows: A=39-99 nM; B=100-200 nM

TABLE 2

| Example Number | Range (EC$_{50}$) |
|---|---|
| 1 | B |
| 2 | B |
| 3 | B |
| 4 | A |
| 5 | 54 nM |
| 6 | A |
| 7 | A |
| 8 | B |
| 9 | B |
| 10 | 110 nM |
| 11 | B |
| 12 | B |
| 13 | B |
| 14 | B |
| 15 | A |
| 16 | 100 nM |
| 17 | B |
| 18 | 154 nM |
| 19 | A |
| 20 | A |
| 21 | 89 nM |
| 22 | A |
| 23 | A |
| 24 | A |
| 25 | A |
| 26 | A |
| 27 | B |
| 28 | B |
| 29 | B |
| 30 | B |
| 31 | B |
| 32 | B |
| 33 | B |
| 34 | B |
| 35 | B |
| 36 | B |
| 37 | A |
| 38 | B |
| 39 | B |
| 40 | 254 nM |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

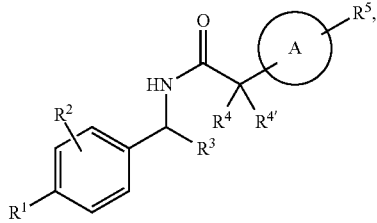

or a pharmaceutically acceptable salt thereof, wherein
A is phenyl;
$R^1$ is $C_4$-$C_6$ alkoxy;
$R^2$ is selected from hydrogen, $C_1$-$C_3$ alkyl; and halo;
$R^3$ is hydroxy-$C_1$-$C_3$ alkyl;
$R^4$ is selected from $C_1$-$C_3$ alkyl and hydroxy-$C_1$-$C_3$ alkyl;
$R^{4'}$ is selected from hydrogen and $C_1$-$C_3$ alkyl; or
$R^4$ and $R^{4'}$, together with the carbon atom to which they are attached, form a $C_3$-$C_6$ cycloalkyl ring; and
$R^5$ is selected from hydrogen, $C_1$-$C_3$ alkyl, and halo.

2. A compound of formula (II)

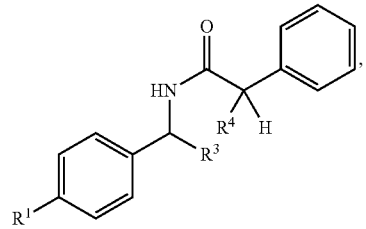

or a pharmaceutically acceptable salt thereof, wherein
$R^1$ is $C_4$-$C_6$ alkoxy;
$R^3$ is selected from
hydroxy-$C_1$-$C_3$ alkyl; and
$(NR^aR^b)$—$C_1$ alkyl; wherein $R^a$ and $R^b$ are each independently selected from hydrogen;
$C_1$-$C_5$ alkyl;
$C_3$-$C_5$ cycloalkyl-$C_1$ alkyl wherein the cycloalkyl is optionally substituted with an amino group;
heterocyclyl-$C_1$ alkyl;
$R^6$—C(O)—; wherein $R^6$ is selected from
amino-$C_1$-$C_5$ alkyl wherein the alkyl is optionally substituted with a $C_1$ alkoxy group;
$C_3$ cycloalkyl-$C_2$ alkyl wherein the alkyl part is substituted with an amino group;
heterocyclyl; and
heterocyclyl-$C_2$ alkyl, wherein the alkyl part is substituted with an amino group;
or, $R^a$ and $R^b$, together with the nitrogen atom to which they are attached, for a morpholinyl or piperazinyl ring wherein the piperazinyl ring is substituted with $C_1$-$C_3$ alkyl; and
$R^4$ is selected from $C_1$-$C_2$ alkyl and hydroxy-$C_1$ alkyl.

3. A compound according to claim 2 selected from

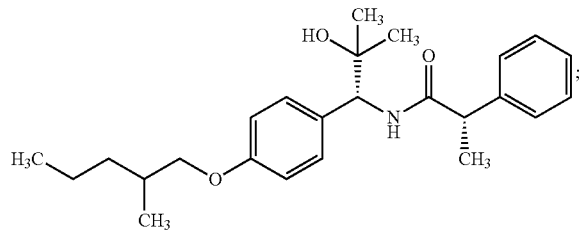

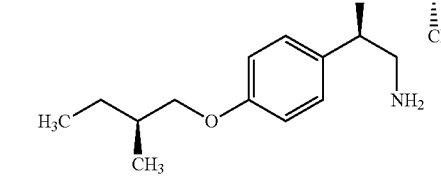

61
-continued
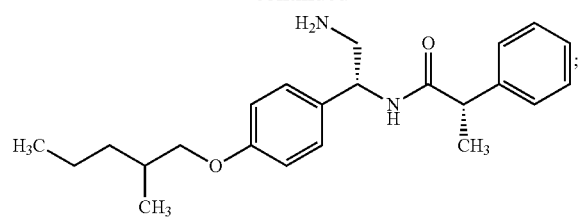
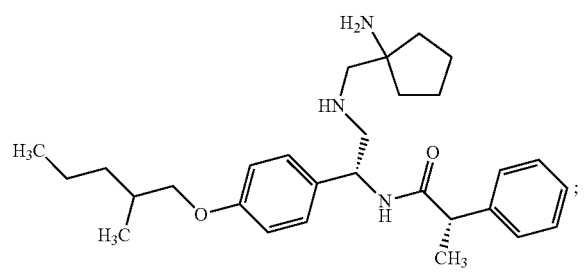
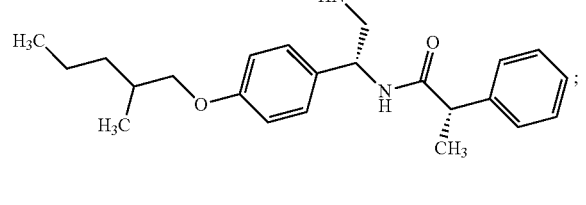
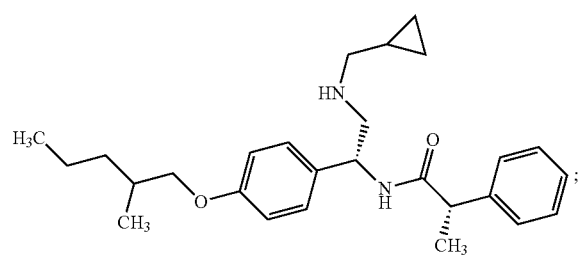
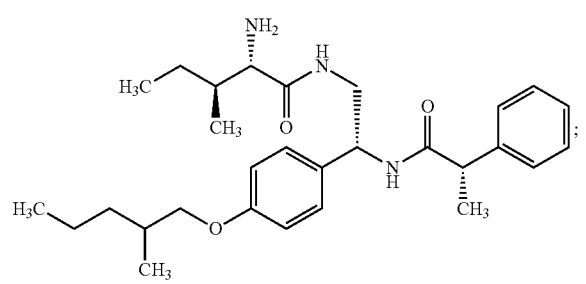
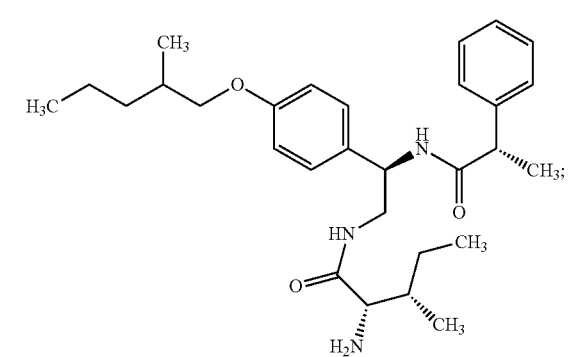
62
-continued
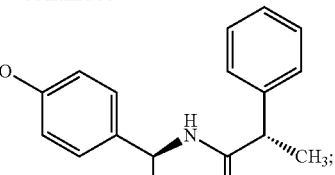
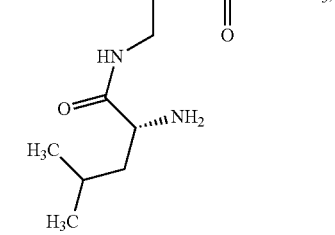
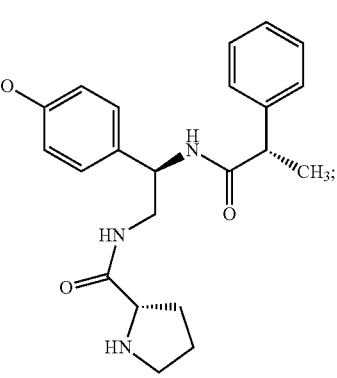
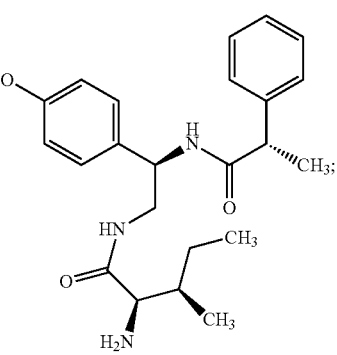
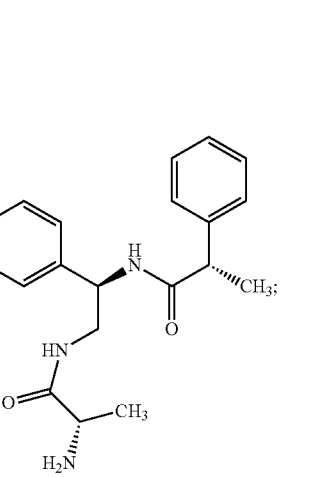

63
-continued
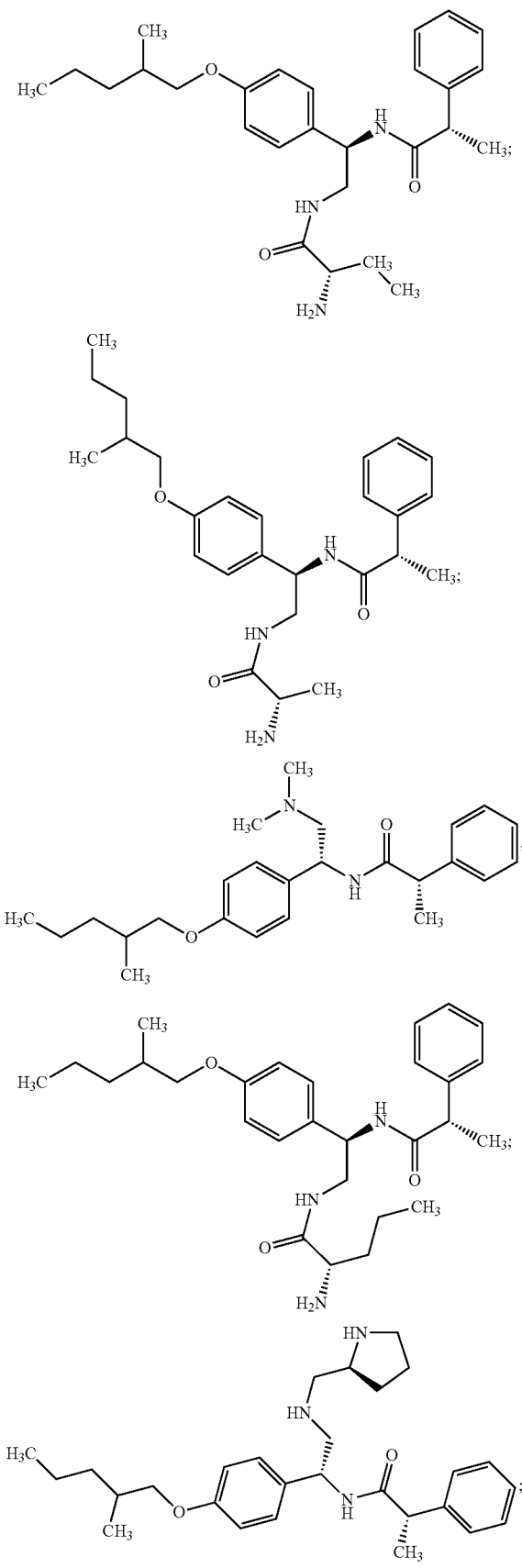
64
-continued
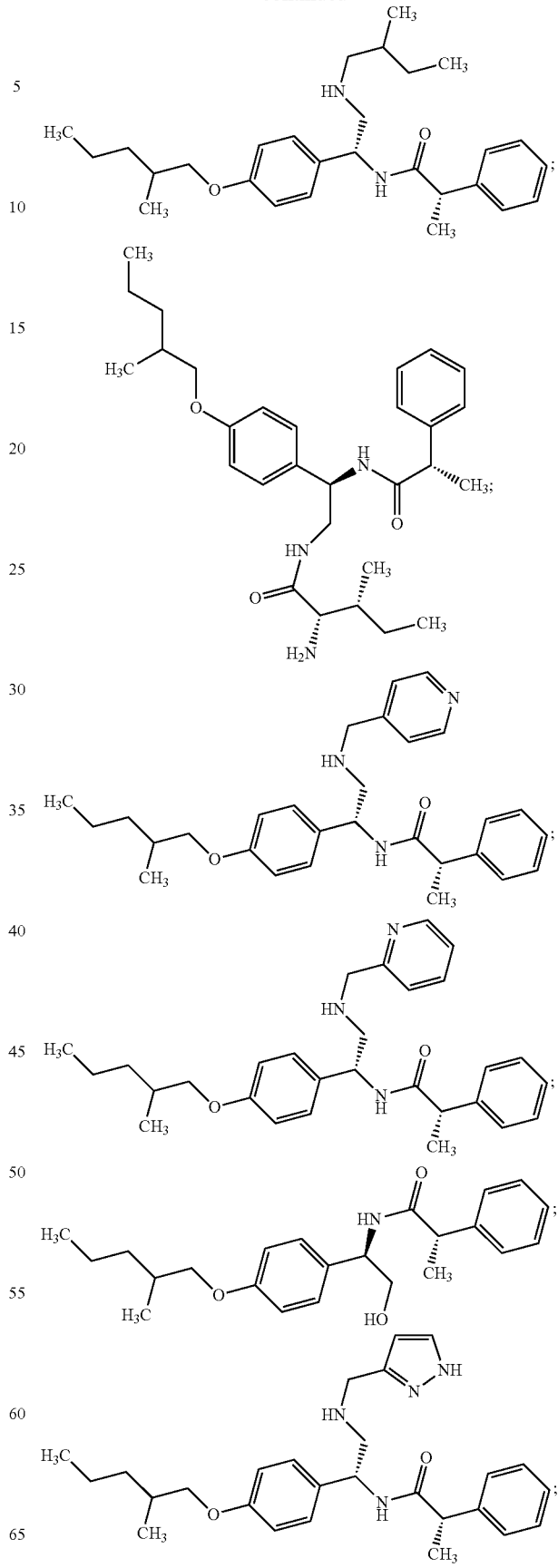

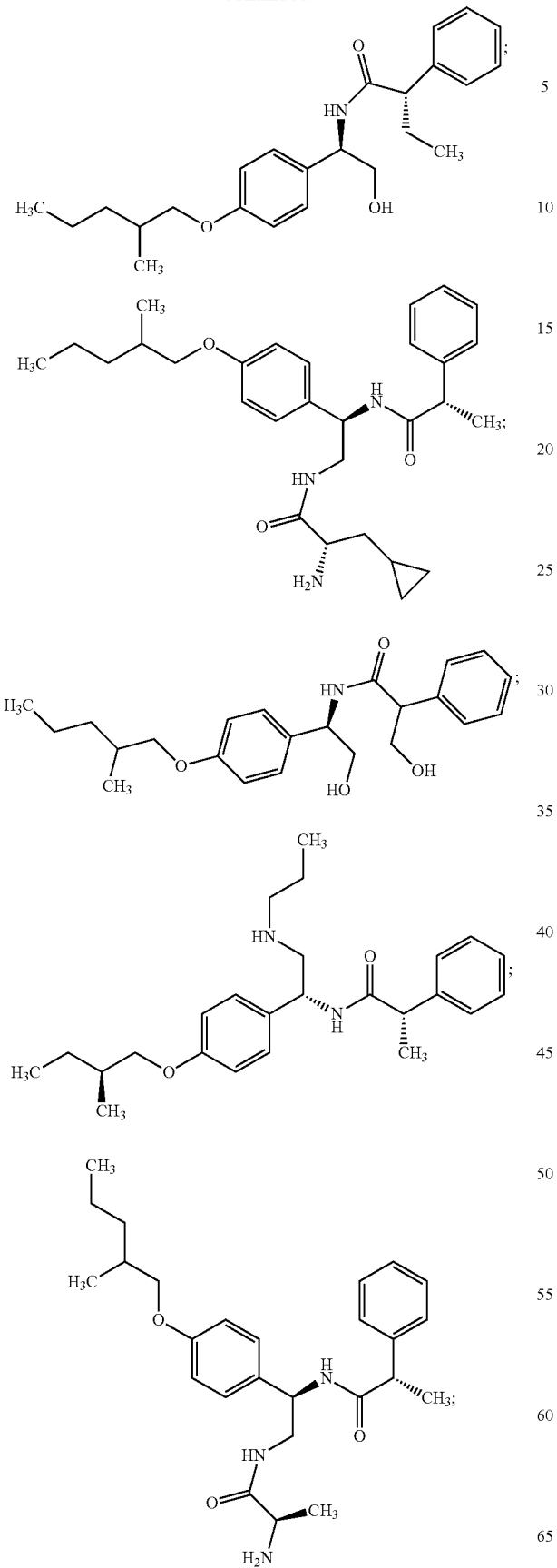
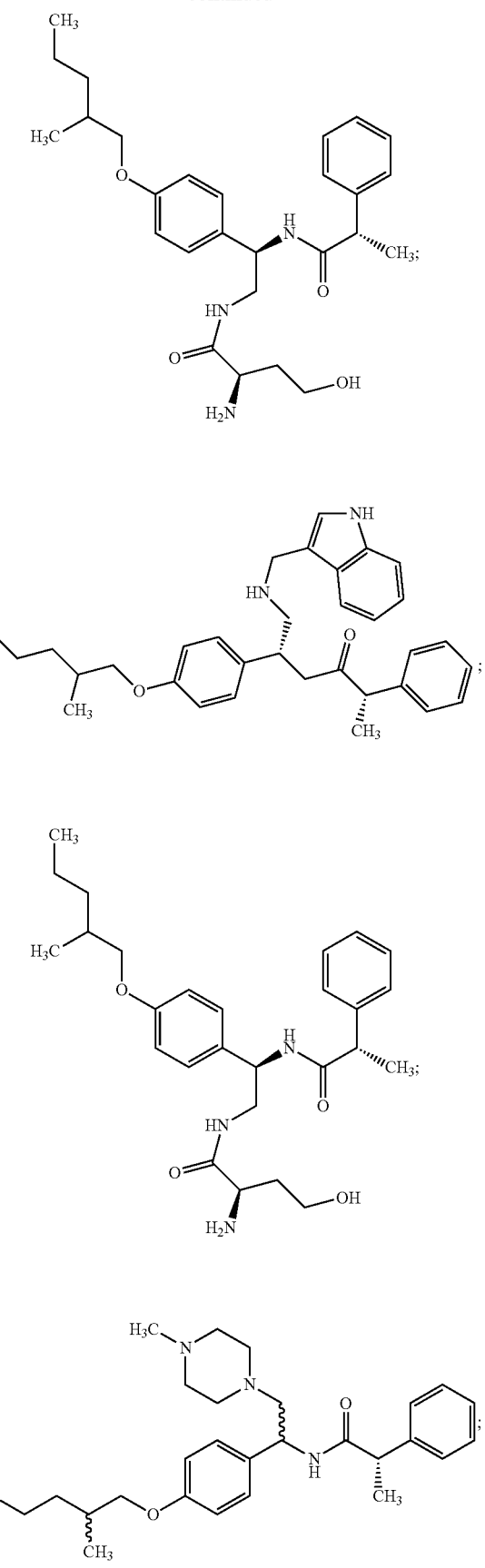

-continued
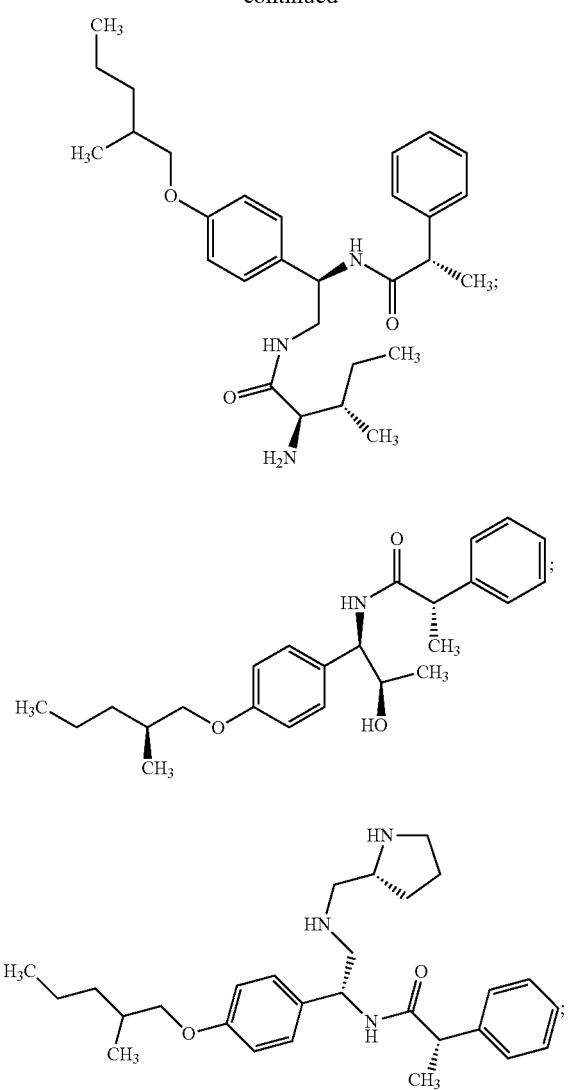
-continued
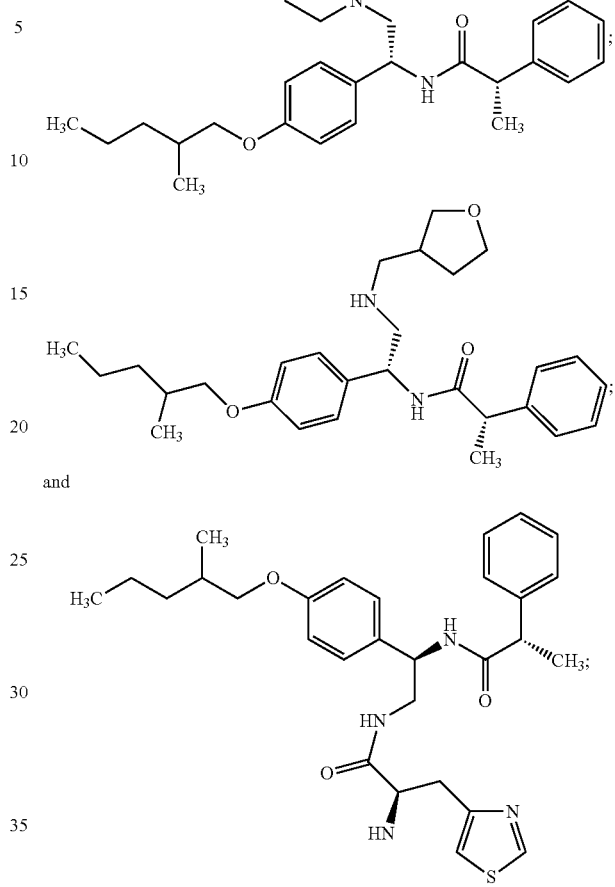
or a pharmaceutically acceptable salt thereof.
4. A composition comprising a compound of claim 1, or a pharmaceutically acceptable salt thereof, and a pharmaceutically acceptable carrier.
* * * * *

UNITED STATES PATENT AND TRADEMARK OFFICE
CERTIFICATE OF CORRECTION

PATENT NO. : 8,304,577 B2
APPLICATION NO. : 12/898016
DATED : November 6, 2012
INVENTOR(S) : Carolyn Dzierba et al.

It is certified that error appears in the above-identified patent and that said Letters Patent is hereby corrected as shown below:

In the Claims:

Claim 3, col. 66, lines 1-19, delete

"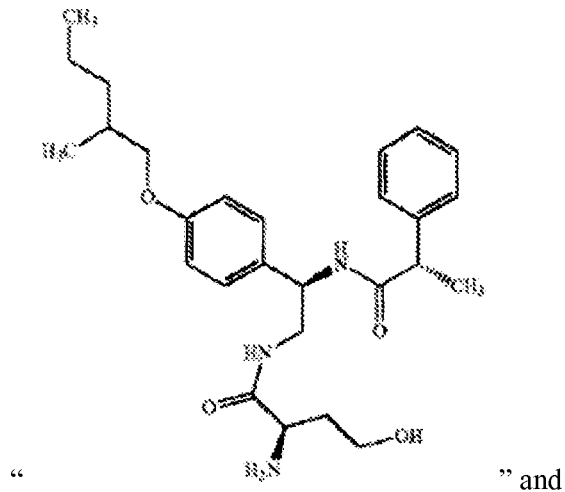" and insert -- 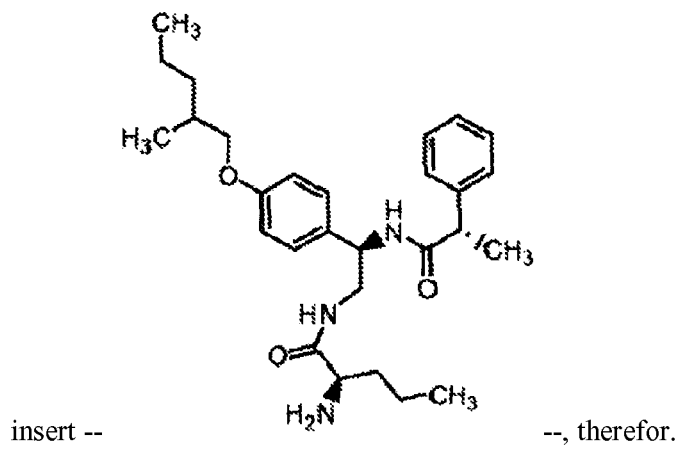 --, therefor.

Signed and Sealed this
Fifth Day of February, 2013

Teresa Stanek Rea
*Acting Director of the United States Patent and Trademark Office*

CERTIFICATE OF CORRECTION (continued)
U.S. Pat. No. 8,304,577 B2

Claim 3, col. 66, lines 22-33, delete

" 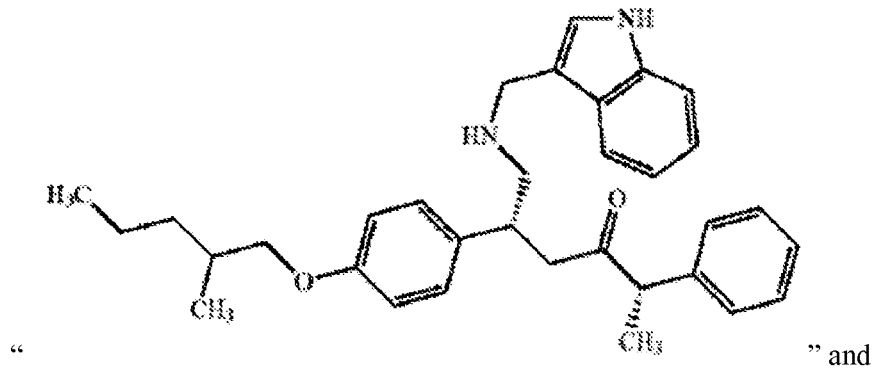 " and insert -- 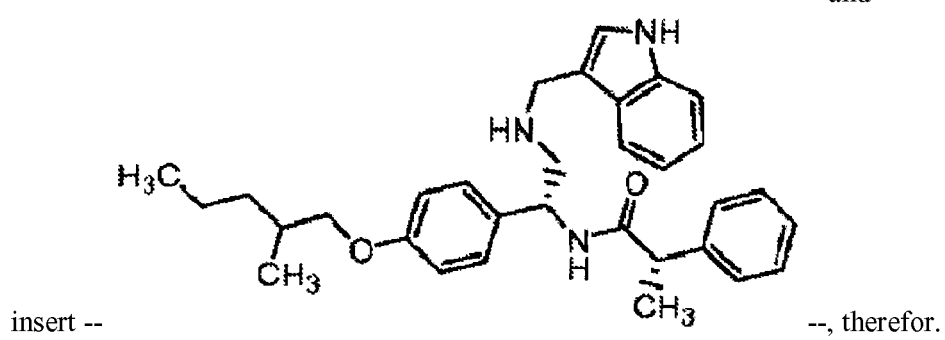 --, therefor.

Claim 3, col. 66, lines 36-54, delete

" 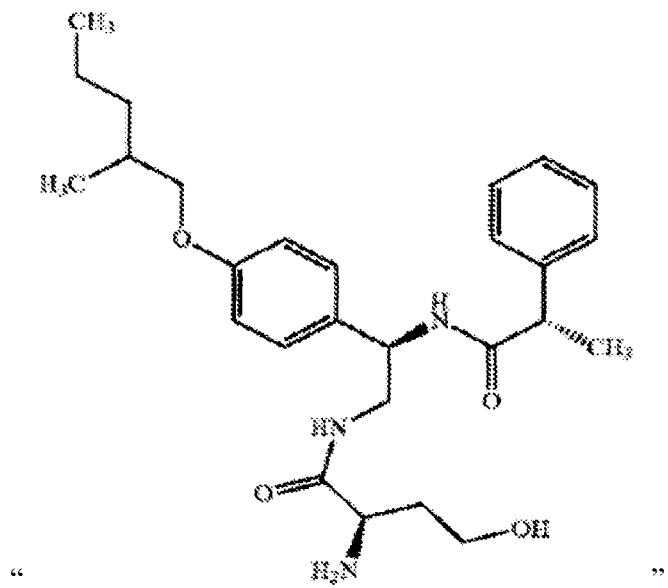 "

and

CERTIFICATE OF CORRECTION (continued)
U.S. Pat. No. 8,304,577 B2 insert -- 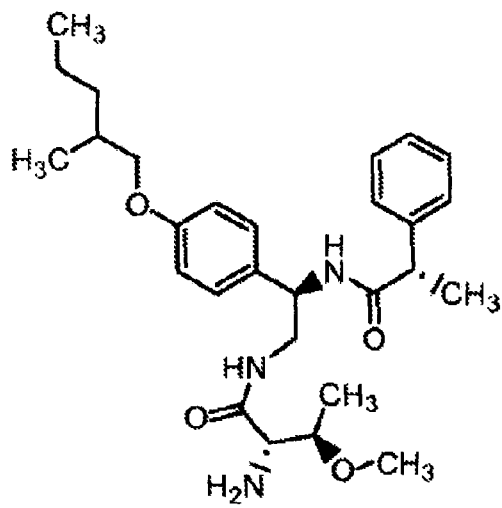 --, therefor.

Claim 3, col. 68, lines 24-37, delete

" 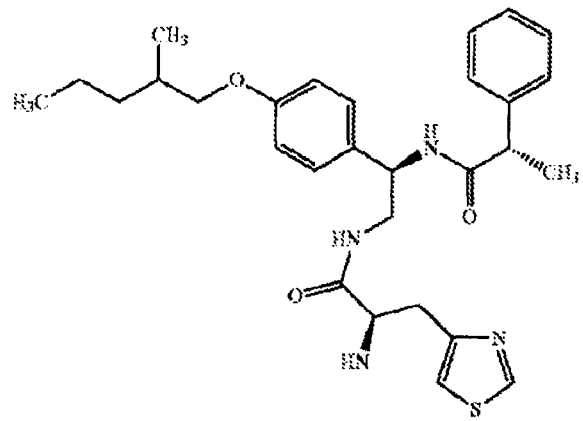 " and insert -- 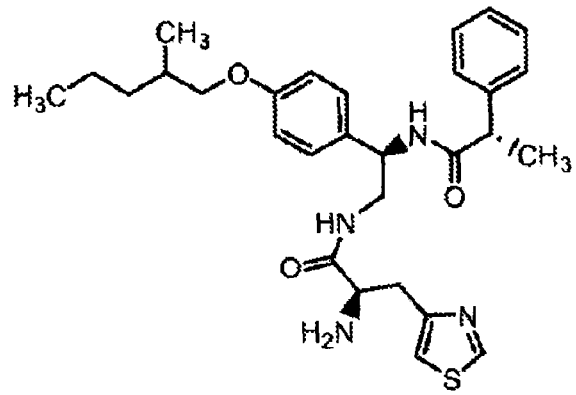 --, therefor.